US011111539B2

(12) United States Patent
Hakonarson et al.

(10) Patent No.: US 11,111,539 B2
(45) Date of Patent: Sep. 7, 2021

(54) IDENTIFICATION OF PEDIATRIC ONSET INFLAMMATORY BOWEL DISEASE LOCI AND METHODS FOR USE THEREOF FOR THE DIAGNOSIS AND TREATMENT OF THE SAME

(71) Applicant: The Children's Hospital of Philadelphia, Philadelphia, PA (US)

(72) Inventors: Hakon Hakonarson, Malvern, PA (US); Jonathan Bradfield, Philadelphia, PA (US); Marcin Imielinski, Cambridge, MA (US); Struan F. A. Grant, Philadelphia, PA (US)

(73) Assignee: THE CHILDREN'S HOSPITAL OF PHILADELPHIA, Philadelphia, PA (US)

( * ) Notice: Subject to any disclaimer, the term of this patent is extended or adjusted under 35 U.S.C. 154(b) by 117 days.

(21) Appl. No.: 15/899,811

(22) Filed: Feb. 20, 2018

(65) Prior Publication Data

US 2019/0218612 A1   Jul. 18, 2019

Related U.S. Application Data

(62) Division of application No. 12/735,843, filed as application No. PCT/US2009/034586 on Feb. 19, 2009, now abandoned.

(60) Provisional application No. 61/029,841, filed on Feb. 19, 2008, provisional application No. 61/059,486, filed on Jun. 6, 2008.

(51) Int. Cl.
*C12Q 1/68* (2018.01)
*C12P 19/34* (2006.01)
*C12Q 1/6883* (2018.01)

(52) U.S. Cl.
CPC ..... *C12Q 1/6883* (2013.01); *C12Q 2600/136* (2013.01); *C12Q 2600/156* (2013.01); *C12Q 2600/158* (2013.01); *C12Q 2600/172* (2013.01)

(58) Field of Classification Search
CPC ............ C12Q 1/6883; C12Q 2600/156; C12Q 2600/158; C12Q 2600/136; C12Q 2600/172; C12Q 2600/106
See application file for complete search history.

(56) References Cited

FOREIGN PATENT DOCUMENTS

WO    2007/073478    6/2007

OTHER PUBLICATIONS

Duerr, R.H. et al. "A Genome-Wide Association Study Identifies IL23R as an Inflammatory Bowel Disease Gene" Science Dec. 1, 2006: vol. 314, Issue 5804, pp. 1461-1463, including 13 pages of supporting material (Year: 2006).*
Peiffer, D. A. et al. "High-resolution genomic profiling of chromosomal aberrations using Infinium whole-genome genotyping" Genome Research 16:1136-1148. (Year: 2006).*
Hanauer S. B. et al. "Maintenance infliximab for Crohn's disease: the ACCENT I randomised trial" Lancet 2002; 359: 1541-49 (Year: 2002).*
Submitted SNP (ss) Report in Submission Format for ss41366837 (rs2315008), Jul. 17, 2005, 1 page printed from www.ncbi.nlm.nih.gov. (Year: 2005).*
Bai, C., et al. "Overexpression of M68/DcR3 in human gastrointestinal tract tumors independent of gene amplification and its location in a four-gene cluster." Proc Natl Acad Sci U S A. Feb. 1, 2000;97(3):1230-5.
Fayad, R., et al. "Apoptosis resistance in ulcerative colitis: high expression of decoy receptors by lamina propria T cells." Eur J Immunol. Aug. 2006;36(8):2215-22.
Kim, S., et al. "Increased expression of soluble decoy receptor 3 in acutely inflamed intestinal epithelia." Clin Immunol. Jun. 2005;115(3):286-94.
Kugathasan, S., et al. "Loci on 20q13 and 21q22 are associated with pediatric-onset inflammatory bowel disease." Nat Genet. Oct. 2008;40(10):1211-5. Epub Aug. 31, 2008.
NCBI Database dbSNP [online]. Reference SNP (refSNP) Cluster Report: rs4809330. Feb. 12, 2003 [Retrieved Jul. 24, 2012]. Retrieved from the Internet: <URL: http://www.ncbi.nlm.nih.gov/projects/SNP/snp_ref.cgi?rs=4809330>; Abstract.
NCBI Signle Nucleotide Polymorphism [online]. Reference SNP (refSNP) Cluster Report: rs2315008. May 25, 2006 [Retrieved on Jul. 18, 2009]. Retrieved from the Internet: <URL: http://www.ncbi.nlm.nih.gov/projects/SNP/snp_ref.cgi?rs=2315008 >; p. 1 and 3.
Online Medelian Inheritance in Man (OMIM) (online). Inflammatory Bowel Disease 24; IBD24 Jan. 30, 2009 [online] (Retrieved on Jul. 17, 2009). Retrieved from the internet <URL: http://www.ncbi.nlm.nih.gov/entrez/dispomim.cgi?id=612566> p. 1.
Pitti, R.M., et al. "Genomic amplification of a decoy receptor for Fas ligand in lung and colon cancer." Nature. Dec. 17, 1998;396(6712):699-703.
The Wellcome Trust Case Control Consortium. Genome-wide association study of 14,000 cases of seven common diseases and 3,000 shared controls. Nature. Jun. 7, 2007;447(7145):661-78.
Yamazaki, K., et al. "Single nucleotide polymorphisms in TNFSFI5 confer susceptibility to Crohn's disease." um Mol Genet. Nov. 15, 2005;14(22):3499-506. Epub Oct. 12, 2005.
Paul, Fundamental Immunology, 3rd edition, 1993, pp. 292-205.

(Continued)

*Primary Examiner* — Stephen T Kapushoc
(74) *Attorney, Agent, or Firm* — Kathleen D. Rigaut; Howson & Howson LLP

(57) ABSTRACT

Compositions and methods for the detection and treatment of inflammatory bowel disease are provided.

12 Claims, 9 Drawing Sheets

Specification includes a Sequence Listing.

(56) References Cited

OTHER PUBLICATIONS

Bendig, Mary Humanization of Rodent Monoclonal Antibodies by CDR Grafting: Methods: a companion methods in encymology 8: 83-93 (1995).
MacCallum, et al. Antibody-Antigen Interactions: Contact Analysis an Binding Site Topography. J. Mol. Biol. 262: 732-745 (1996).
Casset, et al. A petpide mimetic of ananti-CD4 monoclonal antibody by rational design, BBRC 307: 198-205 (2003).
Wu, et al. "Humanization of a Murine Monoclonal Antibody by Simultaneous Optimization of Framework and CDR Residues" J. Mol. Biol. 294: 151-162 (1999).
Skolnick, et al. From genes to protien structure and function: novel applications of computational approaches in the genomic era, Tibtech 18: 34-39, Jan. 2000.
Vajdos, et al. Comprehensive Functional Maps of the Antigen-binding Site of an Anti-ErbB2 Antibody Obtained with Shotgun Scanning Mutagenesis, J. Mol. Biol. 320: 415-428 (2002).

\* cited by examiner

A)

B)

A)

B)

a) CD b) UC c) IBD

IDENTIFICATION OF PEDIATRIC ONSET INFLAMMATORY BOWEL DISEASE LOCI AND METHODS FOR USE THEREOF FOR THE DIAGNOSIS AND TREATMENT OF THE SAME

CROSS-REFERENCE TO RELATED APPLICATIONS

This application is a Divisional application of U.S. application Ser. No. 12/735,843 filed Apr. 1, 2011 which is a § 371 filing of PCT/US09/34586 filed Feb. 19, 2009 which in turn claims priority to U.S. Provisional Applications 61/029,841 and 61/059,486 filed Feb. 19, 2008 and Jun. 6, 2008 respectively, the entire disclosures of each being incorporated herein by reference.

INCORPORATION-BY-REFERENCE OF MATERIAL SUBMITTED IN ELECTRONIC FORM

Incorporated herein by reference in its entirety is the Sequence Listing submitted via EFS-Web as a text file named SequenceListing.txt., created May 26, 2020 and having a size of 1,356 bytes.

FIELD OF THE INVENTION

This invention relates to the fields of inflammatory disorders and genetic testing. More specifically, the invention provides compositions and methods for the diagnosis and treatment inflammatory bowel disease (IBD) in pediatric and adult patients.

BACKGROUND OF THE INVENTION

Several publications and patent documents are cited throughout the specification in order to describe the state of the art to which this invention pertains. Each of these citations is incorporated by reference herein as though set forth in full.

Inflammatory bowel disease (IBD) is a common inflammatory disorder with complex etiology that involves both genetic and environmental triggers, including but not limited to defects in bacterial clearance, a defective mucosal barrier and persistent dysregulation of the immune response to commensal intestinal bacteria[1-3]. IBD is characterized by two distinct phenotypes: Crohn's disease (CD) and ulcerative colitis (UC). Among children, CD is twice as common as UC. CD can affect any part of the gut with discontinuous penetrating lesions and is characterized by full thickness (transmural), discrete inflammation which leads to stricturing and fistulization, and can occur in the large and small bowel, whereas in UC, the impact is as a confluent inflammation of the colon, nearly always involving the rectum, ranging from proctitis to a pancolitis and is characterized by mucosal inflammation[4]; CD impacts 100-250/100,000 and UC impacts 80-100/100,000 in the UK and the USA. Recurrence of both CD and UC among families[5-7,8], twin studies[9], phenotype concordance among families[10-12], identification of specific genetic risk factors, and environmental components all demonstrate that both disorders are complex genetic diseases.

Linkage studies facilitated the 'positional cloning' of the first two genes involved in the pathogenesis of the disease[13], including CARD15 (caspase recruitment domain family, member 15; also known as NOD2), which is now considered the first and most widely replicated CD susceptibility gene[14-16]. The IBD5 locus, a site on chromosome 5q31, and its association with CD[17-19] has not been further resolved due to extensive linkage disequilibrium (LD) in the region[20].

With the more recent introduction of the GWA technology, several genes involved in the pathogenesis of IBD have been uncovered. Duerr et al were the first to report a highly significant association between CD and sequence variants in the interleukin 23 receptor (IL23R) gene on chromosome 1p31 in non-Jewish, ileal CD cases of European ancestry using the HumanHap 317K gene chip from Illumina[20]. A coding variant, rs11209026 (Arg381Gln), was shown to confer a strong protective effect against the disease and was then replicated in the same study in separate cohorts of patients with CD or UC. Others have replicated this finding, including our own laboratory in a cohort with pediatric onset CD[21], lending further support for the protective role of the IL23R gene in IBD[21]. Around the same time, Hampe et al[22] reported an independent association of a nsSNP in the autophagy-related 16-like 1 gene (ATG16L1) on chromosome 2q37.1[22] (a threonine-to-alanine substitution at amino acid position 300 of the protein—T300A) and confirmed the previously reported variants in the SLC22A4 and CARD15 genes.

Rioux et al[23] presented a follow-up GWA study to their IL23R finding in ileal CD and two independent replication studies, identifying several new regions of association to CD. Specifically, in addition to the previously established CARD15 and IL23R associations, they also reported strong association with independent replication to variation within an intergenic region on 10q21.1, in the genomic regions encoding PHOX2B, NCF4 and FAM92B. They also independently identified strong and significantly replicated association with the coding variant in ATG16L1.

The Wellcome Trust Case Control Consortium[24] described a joint GWA study (using the Affymetrix GeneChip 500K platform) carried out in the British population, which examined 2,000 individuals for each of seven major diseases, including CD, against a shared set of approximately 3,000 controls; they identified in the case-control comparison nine independent association signals at $P<5\times10^{-7}$ thereby corroborating the ATG16L1, 5q31, IL23R, 10q21 and 5p13.1 loci[25]. Their study also identified four further new strong association signals, located on chromosomes 3p21, 5q33, 10q24 and 18p11. Parkes et al also reported replication for the signals in the ATG16L1 and IRGM genes[27]. We have also successfully demonstrated the association of ATG16L1 variation in our cohort of pediatric onset CD[28].

Given that genetic variants associated with CD do not account for the entire genetic risk, further studies are necessary to further identify and characterize novel IBD genes. GWA studies have confirmed that genetic variants associated with IBD are indeed common and contribute only modestly to overall disease risk. As such, a barrier to performing further studies is the need for large sample sizes necessary to identify additional variants with smaller effect size; however, an alternative strategy is to ascertain individuals with a younger age of disease onset, as has been carried out with Alzheimer's disease, type 2 diabetes and breast cancer. Such a tactic is attractive for IBD for several reasons. First, CD-affected children are more likely to have colonic CD than adults. Second, UC-affected children are more likely to have extensive colitis than adults and a young age of IBD onset is associated with a greater family history of IBD. Taken together, childhood onset IBD demonstrates unique characteristics in phenotype, severity and family history; all of which justify ascertaining children with IBD for GWA studies to potentially identify new IBD genes.

SUMMARY OF THE INVENTION

In accordance with the present invention, compositions and methods are provided for diagnosis and treatment of pediatric IBD. An exemplary method entails detecting the presence of a single nucleotide polymorphism set forth in the Tables provided in the Examples below in a target polynucleotide wherein if the single nucleotide polymorphism is present, the patient has an increased risk for developing IBD. Exemplary single nucleotide polymorphisms associated with the development of IBD reside on chromosome 20q13 or chromosome 21q22 include, without limitation, a T at rs2315008, or an A at RS4809330 in the TNFRSF6B gene on chromosome 20 and an A at rs2836878 in the PSMG1 gene on chromosome 21. Notably, several other loci have been identified herein which comprise alterations associated with the IBD phenotype. The methods of the invention can include alternative means for detecting the disclosed polymorphisms. For example, such methods of detection can further comprises processes such as specific hybridization, measurement of allele size, restriction fragment length polymorphism analysis, allele-specific hybridization analysis, single base primer extension reaction, and sequencing of an amplified polynucleotide.

In yet another aspect, nucleic acid molecules useful for amplifying the nucleic acids encoding the single nucleotide polymorphisms disclosed herein are provided. Also provided are solid supports comprising suitable nucleic acid targets to facilitate detection of such SNPS in patient samples. A suitable solid support for this process includes a microarray.

Finally, the invention also encompasses screening methods to identify agents which modulate the aberrant physiological process associated with IBD observed in the SNP containing cells described herein. An exemplary method entails providing colonic biopsy samples comprising at least one of a T at rs2315008, an A at RS4809330 in the TNFRSF6B gene and/or an A at rs2836878 in the PSMG1 gene; providing cells which express these gene(s) which lack the cognate polymorphisms (step b); contacting each cell type with a test agent and analyzing whether said agent alters aberrant physiological process associated with IBD in the samples of step a) relative to those of step b), thereby identifying agents which modulate IBD. Aberrant physiological processes associated with the IBD phenotype, include, without limitation, defects in the colonic mucosal barrier, defects in bacterial clearance and dysregulation of immune responses to commensal intestinal bacteria. Each of the SNPs described herein can be assessed in this manner, alone or in combination.

Also provided are transgenic mice comprising the SNP containing nucleic acid molecules described herein. Such mice provide a superior in vivo screening tool to identify agents which modulate the progression and development of IBD.

BRIEF DESCRIPTION OF THE DRAWING

FIG. 1.

DETAILED DESCRIPTION OF THE INVENTION

Figure 1A:
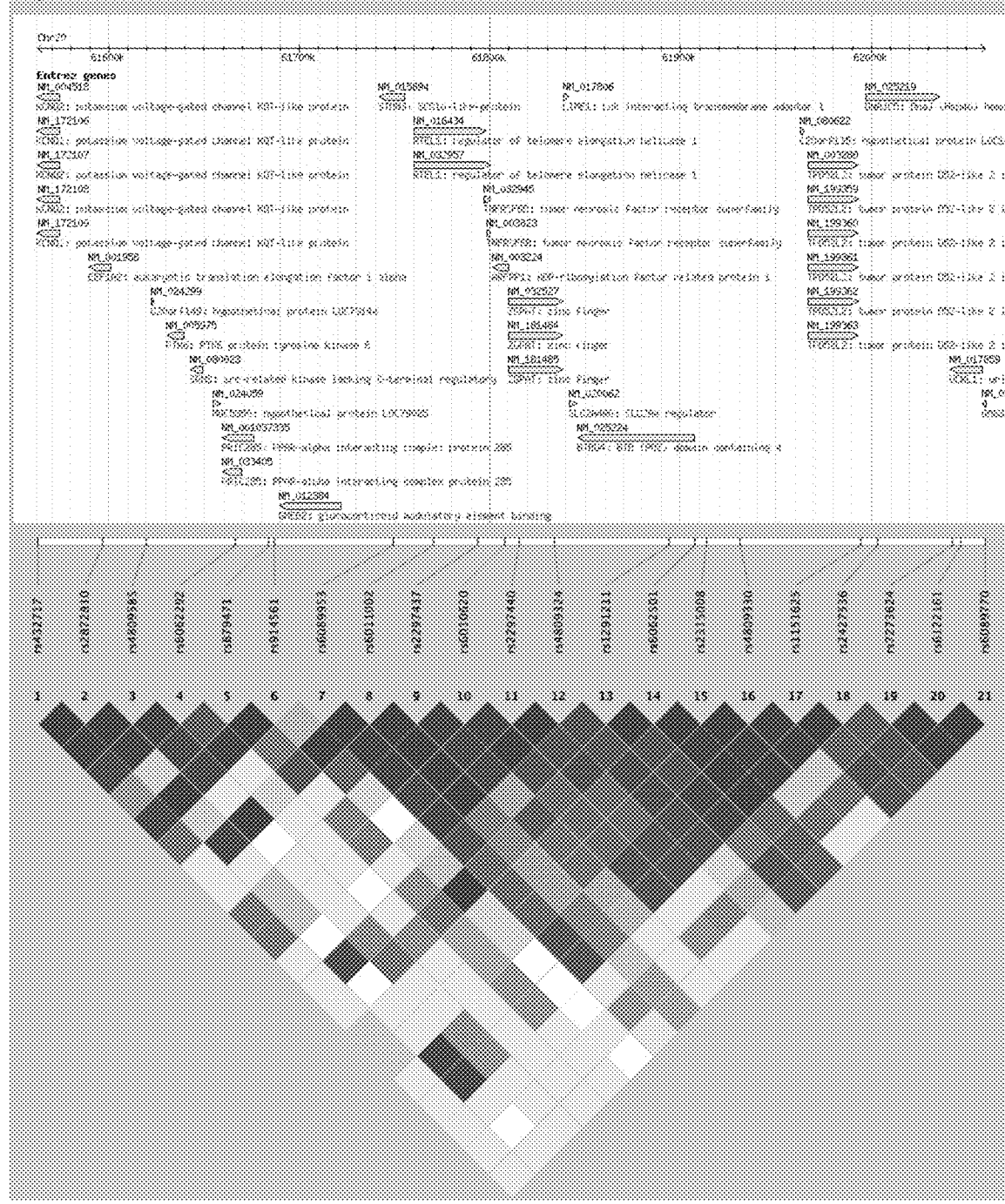
FIG. 1A: Linkage disequilibrium (D') between SNPs at the 20q13 locus in the control cohort together with the corresponding Haploview gene track. The association signal resides in a region of LD that harbors the genes RTEL1, TNFRSF6B, ARFRP1, ZGPAT and LIME1.

Inflammatory bowel disease (IBD) constitutes two related clinical entities, Crohn's disease (CD) and ulcerative colitis (UC), both of which cause abdominal pain, diarrhea and growth disturbances. Family and twin studies have indicated that genetic factors play a large role in an individual's risk of developing IBD and recently, genome-wide association (GWA) studies have associated several variants in the caspase recruitment domain 15 (CARD15), interleukin 23 receptor (IL23R) and autophagy related 16-like 1 (ATG16L1) genes with IBD, notably to the CD subphenotype. However, these genetic variations account for only a small portion of the overall genetic susceptibility of CD and their contribution to UC pathogenesis is even less. We hypothesized that an alternative strategy such as stratifying cases by age of onset may be needed to identify new IBD genes. We have performed a GWA analysis in a cohort of 1,011 pediatric onset IBD cases, and 4,250 age matched controls. We observed and replicated significantly associated novel loci on several chromosomes. Example 1 describes loci residing on chromosome 20q13 and 21q22 which are close to the tumor necrosis factor receptor superfamily member 6B (TNFRSF6B) and Down syndrome critical region protein 2 isoform (PSMG1) genes, respectively. Colonic biopsies also demonstrate expression differences in TNFRSF6B mRNA message between IBD patients and disease-free controls, driven most obviously by local mucosal inflammation. When addressing the individual subcomponents of IBD, we identified an additional novel locus on 21q21 associated specifically with the colonic form of CD. In addition, when analyzing UC separately, we detected strong association with four single nucleotide polymorphisms (SNPs) within the major histocompatibility complex (MHC) on chromosome 6q21. Finally, we show that CARD15 is only associated with CD in patients with ileal disease and that the signal is absent in CD patients with colon-only disease. In conclusion, we have discovered novel susceptibility loci in pediatric onset IBD on 20q13 and 21q22, and identified TNFRSF6B and PSMG1 respectively as IBD susceptibility genes. Example II provides additional loci that provide new targets for the development of agents useful for the treatment of IBD.

In Example III, additional novel IBD associated loci are provided: IL27 on 16p11 and LNPEP-LRAP on 5q15 as CD loci, SMAD3 on 15q22 and HORMAD2 on 21q22. The fifth locus is a Toll-like receptor gene cluster on 4p14 for UC with onset prior to 8 years of age ($P=1.81\times10^{-8}$); we had a limited sized replication cohort and detected evidence of association. Our results also revealed that 21 of 32 previously implicated adult-onset CD loci and 8 of 15 previously implicated adult-onset UC loci contribute to the pathogenesis of the childhood-onset form of the disease. Using these data, we modeled the cumulative effect of the most significant risk alleles detected, demonstrating, for instance, that children carrying 34 or more of the common CD risk alleles have ~13-fold increased risk of developing CD, while children carrying 20 or more of the common UC risk alleles have ~7-fold increased risk of developing UC.

The results presented herein advance the current understanding of pediatric-onset IBD by highlighting key pathogenetic mechanisms, most notably Th17 signaling and innate immunity based on the discovery of the IL27 and TLR loci in CD and UC, respectively. These observations clarify the relationship with adult-onset disease and quantify the cumulative IBD risk conferred by multiple risk alleles in pediatric-onset disease, an important contribution to the future development of a molecular diagnostic for IBD.

Definitions

For purposes of the present invention, "a" or "an" entity refers to one or more of that entity; for example, "a cDNA" refers to one or more cDNA or at least one cDNA. As such, the terms "a" or "an," "one or more" and "at least one" can be used interchangeably herein. It is also noted that the terms "comprising," "including," and "having" can be used interchangeably. Furthermore, a compound "selected from the group consisting of" refers to one or more of the compounds in the list that follows, including mixtures (i.e. combinations) of two or more of the compounds. According to the present invention, an isolated, or biologically pure molecule is a compound that has been removed from its natural milieu. As such, "isolated" and "biologically pure" do not necessarily reflect the extent to which the compound has been purified. An isolated compound of the present invention can be obtained from its natural source, can be produced using laboratory synthetic techniques or can be produced by any such chemical synthetic route.

"IBD-associated SNP or specific marker" is a SNP or marker which is associated with an increased or decreased risk of developing IBD not found normal patients who do not have this disease. Such markers may include but are not limited to nucleic acids, proteins encoded thereby, or other small molecules.

A "single nucleotide polymorphism (SNP)" refers to a change in which a single base in the DNA differs from the usual base at that position. These single base changes are called SNPs or "snips." Millions of SNP's have been cataloged in the human genome. Some SNPs such as that which causes sickle cell are responsible for disease. Other SNPs are normal variations in the genome. These are to be distinguished from those associated with the disease phenotype.

The term "genetic alteration" as used herein refers to a change from the wild-type or reference sequence of one or more nucleic acid molecules. Genetic alterations include without limitation, base pair substitutions, additions and deletions of at least one nucleotide from a nucleic acid molecule of known sequence.

The term "solid matrix" as used herein refers to any format, such as beads, microparticles, a microarray, the surface of a microtitration well or a test tube, a biacore chip, a dipstick or a filter. The material of the matrix may be polystyrene, cellulose, latex, nitrocellulose, nylon, polyacrylamide, dextran or agarose.

The phrase "consisting essentially of" when referring to a particular nucleotide or amino acid means a sequence having the properties of a given SEQ ID NO. For example, when used in reference to an amino acid sequence, the phrase includes the sequence per se and molecular modifications that would not affect the functional and novel characteristics of the sequence.

"Target nucleic acid" as used herein refers to a previously defined region of a nucleic acid present in a complex nucleic acid mixture wherein the defined wild-type region contains at least one known nucleotide variation which may or may not be associated with IBD. The nucleic acid molecule may be isolated from a natural source by cDNA cloning or subtractive hybridization or synthesized manually. The nucleic acid molecule may be synthesized manually by the triester synthetic method or by using an automated DNA synthesizer.

With regard to nucleic acids used in the invention, the term "isolated nucleic acid" is sometimes employed. This term, when applied to DNA, refers to a DNA molecule that is separated from sequences with which it is immediately contiguous (in the 5' and 3' directions) in the naturally occurring genome of the organism from which it was derived. For example, the "isolated nucleic acid" may comprise a DNA molecule inserted into a vector, such as a plasmid or virus vector, or integrated into the genomic DNA of a prokaryote or eukaryote. An "isolated nucleic acid molecule" may also comprise a cDNA molecule. An isolated nucleic acid molecule inserted into a vector is also sometimes referred to herein as a recombinant nucleic acid molecule.

With respect to RNA molecules, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form.

By the use of the term "enriched" in reference to nucleic acid it is meant that the specific DNA or RNA sequence constitutes a significantly higher fraction (2-5 fold) of the total DNA or RNA present in the cells or solution of interest than in normal cells or in the cells from which the sequence was taken. This could be caused by a person by preferential reduction in the amount of other DNA or RNA present, or by a preferential increase in the amount of the specific DNA or RNA sequence, or by a combination of the two. However, it should be noted that "enriched" does not imply that there are no other DNA or RNA sequences present, just that the relative amount of the sequence of interest has been significantly increased.

It is also advantageous for some purposes that a nucleotide sequence be in purified form. The term "purified" in reference to nucleic acid does not require absolute purity (such as a homogeneous preparation); instead, it represents an indication that the sequence is relatively purer than in the natural environment (compared to the natural level, this level should be at least 2-5 fold greater, e.g., in terms of mg/ml). Individual clones isolated from a cDNA library may be purified to electrophoretic homogeneity. The claimed DNA molecules obtained from these clones can be obtained directly from total DNA or from total RNA. The cDNA clones are not naturally occurring, but rather are preferably obtained via manipulation of a partially purified naturally occurring substance (messenger RNA). The construction of a cDNA library from mRNA involves the creation of a synthetic substance (cDNA) and pure individual cDNA clones can be isolated from the synthetic library by clonal selection of the cells carrying the cDNA library. Thus, the process which includes the construction of a cDNA library from mRNA and isolation of distinct cDNA clones yields an approximately $10^{-6}$-fold purification of the native message. Thus, purification of at least one order of magnitude, preferably two or three orders, and more preferably four or five orders of magnitude is expressly contemplated. Thus the term "substantially pure" refers to a preparation comprising at least 50-60% by weight the compound of interest (e.g., nucleic acid, oligonucleotide, etc.). More preferably, the preparation comprises at least 75% by weight, and most preferably 90-99% by weight, the compound of interest. Purity is measured by methods appropriate for the compound of interest.

The term "complementary" describes two nucleotides that can form multiple favorable interactions with one another. For example, adenine is complementary to thymine as they can form two hydrogen bonds. Similarly, guanine and cytosine are complementary since they can form three hydrogen bonds. Thus if a nucleic acid sequence contains the following sequence of bases, thymine, adenine, guanine and cytosine, a "complement" of this nucleic acid molecule would be a molecule containing adenine in the place of thymine, thymine in the place of adenine, cytosine in the place of guanine, and guanine in the place of cytosine. Because the complement can contain a nucleic acid sequence that forms optimal interactions with the parent nucleic acid molecule, such a complement can bind with high affinity to its parent molecule.

With respect to single stranded nucleic acids, particularly oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence. For example, specific hybridization can refer to a sequence which hybridizes to any IBD specific marker gene or nucleic acid, but does not hybridize to other nucleotides. Appropriate conditions enabling specific hybridization of single stranded nucleic acid molecules of varying complementarity are well known in the art.

For instance, one common formula for calculating the stringency conditions required to achieve hybridization between nucleic acid molecules of a specified sequence homology is set forth below (Sambrook et al., *Molecular Cloning*, Cold Spring Harbor Laboratory (1989):

$$T_m = 81.5° C. + 16.6 \text{ Log } [Na+] + 0.41(\% \text{ G+C}) - 0.63(\% \text{ formamide}) - 600/\#bp \text{ in duplex}$$

As an illustration of the above formula, using [Na+]= [0.368] and 50% formamide, with GC content of 42% and an average probe size of 200 bases, the $T_m$ is 57"C. The $T_m$ of a DNA duplex decreases by 1-1.5"C with every 1% decrease in homology. Thus, targets with greater than about 75% sequence identity would be observed using a hybridization temperature of 42"C.

The stringency of the hybridization and wash depend primarily on the salt concentration and temperature of the solutions. In general, to maximize the rate of annealing of the probe with its target, the hybridization is usually carried out at salt and temperature conditions that are 20-25° C. below the calculated $T_m$ of the hybrid. Wash conditions should be as stringent as possible for the degree of identity of the probe for the target. In general, wash conditions are selected to be approximately 12-20° C. below the $T_m$ of the hybrid. In regards to the nucleic acids of the current invention, a moderate stringency hybridization is defined as hybridization in 6×SSC, 5×Denhardt's solution, 0.5% SDS and 100 µg/ml denatured salmon sperm DNA at 42° C., and washed in 2×SSC and 0.5% SDS at 55° C. for 15 minutes. A high stringency hybridization is defined as hybridization in 6×SSC, 5×Denhardt's solution, 0.5% SDS and 100 µg/ml denatured salmon sperm DNA at 42° C., and washed in 1×SSC and 0.5% SDS at 65° C. for 15 minutes. A very high stringency hybridization is defined as hybridization in 6×SSC, 5×Denhardt's solution, 0.5% SDS and 100 µg/ml denatured salmon sperm DNA at 42° C., and washed in 0.1×SSC and 0.5% SDS at 65° C. for 15 minutes.

The term "oligonucleotide," as used herein is defined as a nucleic acid molecule comprised of two or more ribo- or deoxyribonucleotides, preferably more than three. The exact size of the oligonucleotide will depend on various factors and on the particular application and use of the oligonucleotide. Oligonucleotides, which include probes and primers, can be any length from 3 nucleotides to the full length of the nucleic acid molecule, and explicitly include every possible number of contiguous nucleic acids from 3 through the full length of the polynucleotide. Preferably, oligonucleotides are at least about 10 nucleotides in length, more preferably at least 15 nucleotides in length, more preferably at least about 20 nucleotides in length.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains 15-25 or more nucleotides, although it may contain fewer nucleotides. The probes herein are selected to be complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Polymerase chain reaction (PCR) has been described in U.S. Pat. Nos. 4,683,195, 4,800,195, and 4,965,188, the entire disclosures of which are incorporated by reference herein.

The term "vector" relates to a single or double stranded circular nucleic acid molecule that can be infected, transfected or transformed into cells and replicate independently or within the host cell genome. A circular double stranded nucleic acid molecule can be cut and thereby linearized upon treatment with restriction enzymes. An assortment of vectors, restriction enzymes, and the knowledge of the nucleotide sequences that are targeted by restriction enzymes are readily available to those skilled in the art, and include any replicon, such as a plasmid, cosmid, bacmid, phage or virus, to which another genetic sequence or element (either DNA or RNA) may be attached so as to bring about the replication of the attached sequence or element. A nucleic acid molecule of the invention can be inserted into a vector by cutting the vector with restriction enzymes and ligating the two pieces together.

Many techniques are available to those skilled in the art to facilitate transformation, transfection, or transduction of the expression construct into a prokaryotic or eukaryotic organism. The terms "transformation", "transfection", and "transduction" refer to methods of inserting a nucleic acid and/or expression construct into a cell or host organism. These methods involve a variety of techniques, such as treating the cells with high concentrations of salt, an electric field, or detergent, to render the host cell outer membrane or wall permeable to nucleic acid molecules of interest, microinjection, PEG-fusion, and the like.

The term "promoter element" describes a nucleotide sequence that is incorporated into a vector that, once inside an appropriate cell, can facilitate transcription factor and/or polymerase binding and subsequent transcription of portions of the vector DNA into mRNA. In one embodiment, the promoter element of the present invention precedes the 5' end of the IBD specific marker nucleic acid molecule such that the latter is transcribed into mRNA. Host cell machinery then translates mRNA into a polypeptide.

Those skilled in the art will recognize that a nucleic acid vector can contain nucleic acid elements other than the promoter element and the IBD specific marker gene nucleic acid molecule. These other nucleic acid elements include, but are not limited to, origins of replication, ribosomal binding sites, nucleic acid sequences encoding drug resistance enzymes or amino acid metabolic enzymes, and nucleic acid sequences encoding secretion signals, localization signals, or signals useful for polypeptide purification.

A "replicon" is any genetic element, for example, a plasmid, cosmid, bacmid, plastid, phage or virus, which is capable of replication largely under its own control. A replicon may be either RNA or DNA and may be single or double stranded.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

As used herein, the terms "reporter," "reporter system", "reporter gene," or "reporter gene product" shall mean an operative genetic system in which a nucleic acid comprises a gene that encodes a product that when expressed produces a reporter signal that is a readily measurable, e.g., by biological assay, immunoassay, radio immunoassay, or by colorimetric, fluorogenic, chemiluminescent or other methods. The nucleic acid may be either RNA or DNA, linear or circular, single or double stranded, antisense or sense polarity, and is operatively linked to the necessary control elements for the expression of the reporter gene product. The required control elements will vary according to the nature of the reporter system and whether the reporter gene is in the form of DNA or RNA, but may include, but not be limited to, such elements as promoters, enhancers, translational control sequences, poly A addition signals, transcriptional termination signals and the like.

The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. Finally, the introduced nucleic acid may exist in the recipient cell or host organism only transiently.

The term "selectable marker gene" refers to a gene that when expressed confers a selectable phenotype, such as antibiotic resistance, on a transformed cell.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of transcription units and other transcription control elements (e.g. enhancers) in an expression vector.

The terms "recombinant organism," or "transgenic organism" refer to organisms which have a new combination of genes or nucleic acid molecules. A new combination of genes or nucleic acid molecules can be introduced into an organism using a wide array of nucleic acid manipulation techniques available to those skilled in the art. The term "organism" relates to any living being comprised of a least one cell. An organism can be as simple as one eukaryotic cell or as complex as a mammal. Therefore, the phrase "a recombinant organism" encompasses a recombinant cell, as well as eukaryotic and prokaryotic organism.

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, addition of stabilizers, or compounding into, for example, immunogenic preparations or pharmaceutically acceptable preparations.

A "specific binding pair" comprises a specific binding member (sbm) and a binding partner (bp) which have a particular specificity for each other and which in normal conditions bind to each other in preference to other molecules. Examples of specific binding pairs are antigens and antibodies, ligands and receptors and complementary nucleotide sequences. The skilled person is aware of many other examples. Further, the term "specific binding pair" is also applicable where either or both of the specific binding member and the binding partner comprise a part of a large molecule. In embodiments in which the specific binding pair comprises nucleic acid sequences, they will be of a length to hybridize to each other under conditions of the assay, preferably greater than 10 nucleotides long, more preferably greater than 15 or 20 nucleotides long.

"Sample" or "patient sample" or "biological sample" generally refers to a sample which may be tested for a particular molecule, preferably an IBD specific marker molecule, such as a marker shown in the tables provided below. Samples may include but are not limited to cells, body fluids, including blood, serum, plasma, urine, saliva, tears, pleural fluid and the like.

The terms "agent" and "test compound" are used interchangeably herein and denote a chemical compound, a mixture of chemical compounds, a biological macromolecule, or an extract made from biological materials such as bacteria, plants, fungi, or animal (particularly mammalian) cells or tissues. Biological macromolecules include siRNA, shRNA, antisense oligonucleotides, peptides, peptide/DNA complexes, and any nucleic acid based molecule which exhibits the capacity to modulate the activity of the SNP containing nucleic acids described herein or their encoded proteins. Agents are evaluated for potential biological activity by inclusion in screening assays described hereinbelow.

Methods of Using Pediatric IBD-Associated SNPS for Diagnosing a Propensity for the Development of Pediatric IBD IBD-related-SNP containing nucleic acids, including but not limited to those listed in the Tables provided below may be used for a variety of purposes in accordance with the present invention. IBD-associated SNP containing DNA, RNA, or fragments thereof may be used as probes to detect the presence of and/or expression of IBD specific markers. Methods in which IBD specific marker nucleic acids may be utilized as probes for such assays include, but are not limited to: (1) in situ hybridization; (2) Southern hybridization (3) northern hybridization; and (4) assorted amplification reactions such as polymerase chain reactions (PCR).

Further, assays for detecting IBD-associated SNPs may be conducted on any type of biological sample, including but not limited to body fluids (including blood, urine, serum, gastric lavage), any type of cell (such as brain cells, white blood cells, mononuclear cells) or body tissue.

From the foregoing discussion, it can be seen that IBD-associated SNP containing nucleic acids, vectors expressing the same, IBD SNP containing marker proteins and anti-IBD specific marker antibodies of the invention can be used to detect IBD associated SNPs in body tissue, cells, or fluid, and alter IBD SNP containing marker protein expression for purposes of assessing the genetic and protein interactions involved in the development of IBD.

In most embodiments for screening for IBD-associated SNPs, the IBD-associated SNP containing nucleic acid in the sample will initially be amplified, e.g. using PCR, to increase the amount of the templates as compared to other sequences present in the sample. This allows the target sequences to be detected with a high degree of sensitivity if they are present in the sample. This initial step may be avoided by using highly sensitive array techniques that are becoming increasingly important in the art.

Alternatively, new detection technologies can overcome this limitation and enable analysis of small samples containing as little as 1 μg of total RNA. Using Resonance Light Scattering (RLS) technology, as opposed to traditional fluorescence techniques, multiple reads can detect low quantities of mRNAs using biotin labeled hybridized targets and anti-biotin antibodies. Another alternative to PCR amplification involves planar wave guide technology (PWG) to increase signal-to-noise ratios and reduce background interference. Both techniques are commercially available from Qiagen Inc. (USA).

Thus any of the aforementioned techniques may be used to detect or quantify IBD-associated SNP marker expression and accordingly, diagnose IBD.

Kits and Articles of Manufacture

Any of the aforementioned products can be incorporated into a kit which may contain an IBD-associated SNP specific marker polynucleotide or one or more such markers immobilized on a Gene Chip, an oligonucleotide, a polypeptide, a peptide, an antibody, a label, marker, or reporter, a pharmaceutically acceptable carrier, a physiologically acceptable carrier, instructions for use, a container, a vessel for administration, an assay substrate, or any combination thereof.

Methods of Using IBD-Associated SNPS for Development of Therapeutic Agents

Since the SNPs identified herein have been associated with the etiology of IBD, methods for identifying agents that modulate the activity of the genes and their encoded products containing such SNPs should result in the generation of efficacious therapeutic agents for the treatment of a variety of disorders associated with this condition.

Chromosomes 20 and 21 contain regions which provide suitable targets for the rational design of therapeutic agents which modulate their activity. Small peptide molecules corresponding to these regions may be used to advantage in the design of therapeutic agents which effectively modulate the activity of the encoded proteins.

Molecular modeling should facilitate the identification of specific organic molecules with capacity to bind to the active site of the proteins encoded by the SNP containing nucleic acids based on conformation or key amino acid residues required for function. A combinatorial chemistry approach will be used to identify molecules with greatest activity and then iterations of these molecules will be developed for further cycles of screening. In certain embodiments, candidate agents can be screening from large libraries of synthetic or natural compounds. Such compound libraries are commercially available from a number of companies including but not limited to Maybridge Chemical Co., (Trevillet, Cornwall, UK), Comgenex (Princeton, N.J.), Microsour (New Milford, Conn.) Aldrich (Milwaukee, Wis.) Akos Consulting and Solutions GmbH (Basel, Switzerland), Ambinter (Paris, France), Asinex (Moscow, Russia) Aurora (Graz, Austria), BioFocus DPI (Switzerland), Bionet (Camelford, UK), Chembridge (San Diego, Calif.), Chem Div (San Diego, Calif.). The skilled person is aware of other sources and can readily purchase the same. Once therapeutically efficacious compounds are identified in the screening assays described herein, the can be formulated in to pharmaceutical compositions and utilized for the treatment of inflammatory bowel disease.

The polypeptides or fragments employed in drug screening assays may either be free in solution, affixed to a solid support or within a cell. One method of drug screening utilizes eukaryotic or prokaryotic host cells which are stably transformed with recombinant polynucleotides expressing the polypeptide or fragment, preferably in competitive binding assays. Such cells, either in viable or fixed form, can be used for standard binding assays. One may determine, for example, formation of complexes between the polypeptide or fragment and the agent being tested, or examine the degree to which the formation of a complex between the polypeptide or fragment and a known substrate is interfered with by the agent being tested.

Another technique for drug screening provides high throughput screening for compounds having suitable binding affinity for the encoded polypeptides and is described in detail in Geysen, PCT published application WO 84/03564, published on Sep. 13, 1984. Briefly stated, large numbers of different, small peptide test compounds, such as those described above, are synthesized on a solid substrate, such as plastic pins or some other surface. The peptide test compounds are reacted with the target polypeptide and washed. Bound polypeptide is then detected by methods well known in the art.

A further technique for drug screening involves the use of host eukaryotic cell lines or cells (such as described above) which have a nonfunctional or altered IBD associated gene. These host cell lines or cells are defective at the polypeptide level. The host cell lines or cells are grown in the presence of drug compound. The rate of cellular metabolism of the host cells is measured to determine if the compound is capable of regulating the cellular metabolism in the defective cells. Host cells contemplated for use in the present invention include but are not limited to bacterial cells, fungal cells, insect cells, mammalian cells, and plant cells. The IBD-associated SNP encoding DNA molecules may be introduced singly into such host cells or in combination to assess the phenotype of cells conferred by such expression. Methods for introducing DNA molecules are also well known to those of ordinary skill in the art. Such methods are set forth in Ausubel et al. eds., Current Protocols in Molecular Biology, John Wiley & Sons, NY, N.Y. 1995, the disclosure of which is incorporated by reference herein.

A wide variety of expression vectors are available that can be modified to express the novel DNA sequences of this invention. The specific vectors exemplified herein are merely illustrative, and are not intended to limit the scope of the invention. Expression methods are described by Sambrook et al. Molecular Cloning: A Laboratory Manual or Current Protocols in Molecular Biology 16.3-17.44 (1989). Expression methods in *Saccharomyces* are also described in Current Protocols in Molecular Biology (1989).

Suitable vectors for use in practicing the invention include prokaryotic vectors such as the pNH vectors (Stratagene Inc., 11099 N. Torrey Pines Rd., La Jolla, Calif. 92037), pET vectors (Novogen Inc., 565 Science Dr., Madison, Wis. 53711) and the pGEX vectors (Pharmacia LKB Biotechnology Inc., Piscataway, N.J. 08854). Examples of eukaryotic vectors useful in practicing the present invention include the vectors pRc/CMV, pRc/RSV, and pREP (Invitrogen, 11588 Sorrento Valley Rd., San Diego, Calif. 92121); pcDNA3.1/ V5&His (Invitrogen); baculovirus vectors such as pVL1392, pVL1393, or pAC360 (Invitrogen); and yeast vectors such as YRP17, YIPS, and YEP24 (New England Biolabs, Beverly, Mass.), as well as pRS403 and pRS413 Stratagene Inc.); Picchia vectors such as pHIL-D1 (Phillips Petroleum Co., Bartlesville, Okla. 74004); retroviral vectors such as PLNCX and pLPCX (Clontech); and adenoviral and adeno-associated viral vectors.

Promoters for use in expression vectors of this invention include promoters that are operable in prokaryotic or eukaryotic cells. Promoters that are operable in prokaryotic cells include lactose (lac) control elements, bacteriophage lambda (pL) control elements, arabinose control elements, tryptophan (trp) control elements, bacteriophage T7 control elements, and hybrids thereof. Promoters that are operable in eukaryotic cells include Epstein Barr virus promoters, adenovirus promoters, SV40 promoters, Rous Sarcoma Virus promoters, cytomegalovirus (CMV) promoters, baculovirus promoters such as AcMNPV polyhedrin promoter, Picchia promoters such as the alcohol oxidase promoter, and *Saccharomyces* promoters such as the gal4 inducible promoter and the PGK constitutive promoter, as well as neuronal-specific platelet-derived growth factor promoter (PDGF), and the Thy-1 promoter.

In addition, a vector of this invention may contain any one of a number of various markers facilitating the selection of a transformed host cell. Such markers include genes associated with temperature sensitivity, drug resistance, or enzymes associated with phenotypic characteristics of the host organisms.

Host cells expressing the IBD-associated SNPs of the present invention or functional fragments thereof provide a system in which to screen potential compounds or agents for the ability to modulate the development of IBD. Thus, in one embodiment, the nucleic acid molecules of the invention may be used to create recombinant cell lines for use in assays to identify agents which modulate aspects of metabolism associated with IBD, including without limitation, aberrant bacterial clearance, altered mucosal barriers and persistent dysregulation of the immune response to commensal intestinal bacteria. Also provided herein are methods to screen for compounds capable of modulating the function of proteins encoded by SNP containing nucleic acids.

Another approach entails the use of phage display libraries engineered to express fragment of the polypeptides encoded by the SNP containing nucleic acids on the phage surface. Such libraries are then contacted with a combinatorial chemical library under conditions wherein binding affinity between the expressed peptide and the components of the chemical library may be detected. U.S. Pat. Nos. 6,057,098 and 5,965,456 provide methods and apparatus for performing such assays.

The goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. See, e.g., Hodgson, (1991) Bio/Technology 9:19-21. In one approach, discussed above, the three-dimensional structure of a protein of interest or, for example, of the protein-substrate complex, is solved by x-ray crystallography, by nuclear magnetic resonance, by computer modeling or most typically, by a combination of approaches. Less often, useful information regarding the structure of a polypeptide may be gained by modeling based on the structure of homologous proteins. An example of rational drug design is the development of HIV protease inhibitors (Erickson et al., (1990) Science 249:527-533). In addition, peptides may be analyzed by an alanine scan (Wells, (1991) Meth. Enzym. 202:390-411). In this technique, an amino acid residue is replaced by Ala, and its effect on the peptide's activity is determined. Each of the amino acid residues of the peptide is analyzed in this manner to determine the important regions of the peptide.

It is also possible to isolate a target-specific antibody, selected by a functional assay, and then to solve its crystal structure. In principle, this approach yields a pharmacore upon which subsequent drug design can be based.

One can bypass protein crystallography altogether by generating anti-idiotypic antibodies (anti-ids) to a functional, pharmacologically active antibody. As a mirror image of a mirror image, the binding site of the anti-ids would be expected to be an analog of the original molecule. The anti-id could then be used to identify and isolate peptides from banks of chemically or biologically produced banks of peptides. Selected peptides would then act as the pharmacore.

Thus, one may design drugs which have, e.g., improved polypeptide activity or stability or which act as inhibitors, agonists, antagonists, etc. of polypeptide activity. By virtue of the availability of SNP containing nucleic acid sequences described herein, sufficient amounts of the encoded polypeptide may be made available to perform such analytical studies as x-ray crystallography. In addition, the knowledge of the protein sequence provided herein will guide those employing computer modeling techniques in place of, or in addition to x-ray crystallography.

In another embodiment, the availability of IBD-associated SNP containing nucleic acids enables the production of strains of laboratory mice carrying the IBD-associated SNPs of the invention. Transgenic mice expressing the IBD-associated SNP of the invention provide a model system in which to examine the role of the protein encoded by the SNP containing nucleic acid in the development and progression towards IBD. Methods of introducing transgenes in laboratory mice are known to those of skill in the art. Three common methods include: 1. integration of retroviral vectors encoding the foreign gene of interest into an early embryo; 2. injection of DNA into the pronucleus of a newly fertilized egg; and 3. the incorporation of genetically manipulated embryonic stem cells into an early embryo. Production of the transgenic mice described above will facilitate the molecular elucidation of the role that a target protein plays in various cellular metabolic processes, including: aberrant bacterial clearance, altered mucosal barriers and persistent dysregulation of the immune response to commensal intestinal bacteria. Such mice provide an in vivo screening tool to study putative therapeutic drugs in a whole animal model and are encompassed by the present invention.

The term "animal" is used herein to include all vertebrate animals, except humans. It also includes an individual animal in all stages of development, including embryonic and fetal stages. A "transgenic animal" is any animal containing one or more cells bearing genetic information altered or received, directly or indirectly, by deliberate genetic manipulation at the subcellular level, such as by targeted recombination or microinjection or infection with recombinant virus. The term "transgenic animal" is not meant to encompass classical cross-breeding or in vitro fertilization, but rather is meant to encompass animals in which one or more cells are altered by or receive a recombinant DNA molecule. This molecule may be specifically targeted to a defined genetic locus, be randomly integrated within a chromosome, or it may be extrachromosomally replicating DNA. The term "germ cell line transgenic animal" refers to a transgenic animal in which the genetic alteration or genetic information was introduced into a germ line cell, thereby conferring the ability to transfer the genetic information to offspring. If such offspring, in fact, possess some or all of that alteration or genetic information, then they, too, are transgenic animals.

The alteration of genetic information may be foreign to the species of animal to which the recipient belongs, or foreign only to the particular individual recipient, or may be genetic information already possessed by the recipient. In the last case, the altered or introduced gene may be expressed differently than the native gene. Such altered or foreign genetic information would encompass the introduction of IBD-associated SNP containing nucleotide sequences.

The DNA used for altering a target gene may be obtained by a wide variety of techniques that include, but are not limited to, isolation from genomic sources, preparation of cDNAs from isolated mRNA templates, direct synthesis, or a combination thereof.

A preferred type of target cell for transgene introduction is the embryonal stem cell (ES). ES cells may be obtained from pre-implantation embryos cultured in vitro (Evans et al., (1981) Nature 292:154-156; Bradley et al., (1984) Nature 309:255-258; Gossler et al., (1986) Proc. Natl. Acad. Sci. 83:9065-9069). Transgenes can be efficiently introduced into the ES cells by standard techniques such as DNA transfection or by retrovirus-mediated transduction. The resultant transformed ES cells can thereafter be combined with blastocysts from a non-human animal. The introduced ES cells thereafter colonize the embryo and contribute to the germ line of the resulting chimeric animal.

One approach to the problem of determining the contributions of individual genes and their expression products is to use isolated IBD-associated SNP genes as insertional cassettes to selectively inactivate a wild-type gene in totipotent ES cells (such as those described above) and then generate transgenic mice. The use of gene-targeted ES cells in the generation of gene-targeted transgenic mice was described, and is reviewed elsewhere (Frohman et al., (1989) Cell 56:145-147; Bradley et al., (1992) Bio/Technology 10:534-539).

Techniques are available to inactivate or alter any genetic region to a mutation desired by using targeted homologous recombination to insert specific changes into chromosomal alleles. However, in comparison with homologous extra-chromosomal recombination, which occurs at a frequency approaching 100%, homologous plasmid-chromosome recombination was originally reported to only be detected at frequencies between $10^{-6}$ and $10^{-3}$. Nonhomologous plasmid-chromosome interactions are more frequent occurring at levels $10^5$-fold to $10^2$ fold greater than comparable homologous insertion.

To overcome this low proportion of targeted recombination in murine ES cells, various strategies have been developed to detect or select rare homologous recombinants. One approach for detecting homologous alteration events uses the polymerase chain reaction (PCR) to screen pools of transformant cells for homologous insertion, followed by screening of individual clones. Alternatively, a positive genetic selection approach has been developed in which a marker gene is constructed which will only be active if homologous insertion occurs, allowing these recombinants to be selected directly. One of the most powerful approaches developed for selecting homologous recombinants is the positive-negative selection (PNS) method developed for genes for which no direct selection of the alteration exists. The PNS method is more efficient for targeting genes which are not expressed at high levels because the marker gene has its own promoter. Non-homologous recombinants are selected against by using the Herpes Simplex virus thymidine kinase (HSV-TK) gene and selecting against its non-homologous insertion with effective herpes drugs such as gancyclovir (GANC) or (1-(2-deoxy-2-fluoro-B-D arabino-fluranosyl)-5-iodou-racil, (FIAU). By this counter selection, the number of homologous recombinants in the surviving transformants can be increased. Utilizing IBD-associated SNP containing nucleic acid as a targeted insertional cassette provides means to detect a successful insertion as visualized, for example, by acquisition of immunoreactivity to an antibody immunologically specific for the polypeptide encoded by IBD-associated SNP nucleic acid and, therefore, facilitates screening/selection of ES cells with the desired genotype.

As used herein, a knock-in animal is one in which the endogenous murine gene, for example, has been replaced with human IBD-associated SNP containing gene of the invention. Such knock-in animals provide an ideal model system for studying the development of IBD.

As used herein, the expression of a IBD-associated SNP containing nucleic acid, fragment thereof, or an IBD-associated SNP fusion protein can be targeted in a "tissue specific manner" or "cell type specific manner" using a vector in which nucleic acid sequences encoding all or a portion of IBD-associated SNP are operably linked to regulatory sequences (e.g., promoters and/or enhancers) that direct expression of the encoded protein in a particular tissue or cell type. Such regulatory elements may be used to advantage for both in vitro and in vivo applications. Promoters for directing tissue specific proteins are well known in the art and described herein.

The nucleic acid sequence encoding the IBD-associated SNP of the invention may be operably linked to a variety of different promoter sequences for expression in transgenic animals. Such promoters include, but are not limited to a prion gene promoter such as hamster and mouse Prion promoter (MoPrP), described in U.S. Pat. No. 5,877,399 and in Borchelt et al., Genet. Anal. 13(6) (1996) pages 159-163; a rat neuronal specific enolase promoter, described in U.S. Pat. Nos. 5,612,486, and 5,387,742; a platelet-derived growth factor B gene promoter, described in U.S. Pat. No. 5,811,633; a brain specific dystrophin promoter, described in U.S. Pat. No. 5,849,999; a Thy-1 promoter; a PGK promoter; a CMV promoter; a neuronal-specific platelet-derived growth factor B gene promoter; and Glial fibrillar acidic protein (GFAP) promoter for the expression of transgenes in glial cells.

Methods of use for the transgenic mice of the invention are also provided herein. Transgenic mice into which a nucleic acid containing the IBD-associated SNP or its encoded protein have been introduced are useful, for example, to develop screening methods to screen therapeutic agents to identify those capable of modulating the development of IBD.

Pharmaceuticals and Peptide Therapies

The elucidation of the role played by the IBD associated SNPs described herein facilitates the development of pharmaceutical compositions useful for treatment and diagnosis of IBD. These compositions may comprise, in addition to one of the above substances, a pharmaceutically acceptable excipient, carrier, buffer, stabilizer or other materials well known to those skilled in the art. Such materials should be non-toxic and should not interfere with the efficacy of the active ingredient. The precise nature of the carrier or other material may depend on the route of administration, e.g. oral, intravenous, cutaneous or subcutaneous, nasal, intramuscular, intraperitoneal routes.

Whether it is a polypeptide, antibody, peptide, nucleic acid molecule, small molecule or other pharmaceutically useful compound according to the present invention that is to be given to an individual, administration is preferably in a "prophylactically effective amount" or a "therapeutically effective amount" (as the case may be, although prophylaxis may be considered therapy), this being sufficient to show benefit to the individual.

The following examples are provided to illustrate certain embodiments of the invention. They are not intended to limit the invention in any way.

Example I

We report herein results of an on-going GWA study where we genotyped 550,000 single nucleotide polymorphisms (SNPs) with the Illumina Human Hap550 Genotyping BeadChip[29] in our study population of 1,011 IBD cases (including 647 CD and 317 UC, with the remainder being indeterminate colitis) of European ancestry and 4,250 controls with matching ancestry (based on self report). Self-reported Caucasian ethnicity proved to be accurate, as the resulting genomic inflation factor for the IBD run was less than 1.1.

The following materials and methods are provided to facilitate the practice of the present invention.

Research Subjects

1. IBD Cohort

Subject Ascertainment and Diagnostic Classification.

Affected individuals with pediatric onset IBD (both CD and UC) were ascertained through the Children's Hospital of Wisconsin and Medical College of Wisconsin, Children's Hospital of Philadelphia, and Cincinnati Children's Hospital Medical Center. Additional UC cases were recruited from Primary Children's Medical Center and from the University of Utah and the Pediatric Gastroenterology & Liver Unit at the Sapienza University of Rome, Italy. In addition, colonic mucosal biopsies from affected IBD patients were obtained from Cincinnati Children's Medical center and from Children's Hospital of Wisconsin during the diagnostic endoscopic procedures. Only subjects of European ancestry were used in the final analysis which consisted of 1,011 individuals with IBD (including 647 CD and 317 UC, with the remainder being indeterminate colitis) where the age of onset for IBD was before their 19th birthday. All subjects had genotypes with call rates above 95%. Informed consent was obtained from all participants, and protocols were approved by the local institutional review board in all participating institutions. The diagnosis of IBD was made after fulfilling standard criteria (ref) across the participating centers that requires (i) one or more of the following symptoms: diarrhea, rectal bleeding, abdominal pain, fever or complicated perianal disease; (ii) occurrence of symptoms on two or more occasions separated by at least 8 weeks or ongoing symptoms of at least 6 weeks' duration and (iii) objective evidence of inflammation from radiologic, endoscopic, video capsule endoscopy. Histological evidence of IBD[33] was considered mandatory for the diagnosis of CD or UC and inclusion in the study.

Phenotypic classification was based on the Montreal classification[37]. For CD we defined disease location based on each subject's all available endoscopic and radiographic evaluation. Based on macroscopic evidence of disease location, we classified each subject by the following: Ileum only: disease of the small bowel proximal to the cecum and distal 4th portion of duodenum; Colon only: any colonic location between cecum and rectum with no small bowel disease; Ileocolonic: disease of the small bowel and any location between cecum and rectum. In addition, any of the above categories may have upper GI tract involvement: disease involving esophagus, stomach, duodenum and perianal disease including: perianal fistulae, perianal and anal lesions including more than single skin tags and anal ulcers. For example, subjects with ileal only, colonic only or ileocolonic disease may also have concomitant upper tract and/or perianal disease.

2. Control Subjects from Philadelphia

The control group included 4250 children with self reported Caucasian status, mean age 9.5 years; 53.0% male and 47.0% female, who did not have IBD (CD or UC). These individual were recruited by CHOP clinicians and nursing staff within the CHOP Health Care Network, including four primary care clinics and several group practices and outpatient practices that included well child visits. The Research Ethics Board of CHOP approved the study, and written informed consent was obtained from all subjects.

Genotyping

Illumina Infinium™ Assay:

We performed high throughput genome-wide SNP genotyping, using the Illumina Infinium™ II HumanHap550 BeadChip technology[29,35] (Illumina, San Diego), at the Center for Applied Genomics at CHOP. We used 750 ng of genomic DNA to genotype each sample, according to the manufacturer's guidelines. On day one, genomic DNA was amplified 1000-1500-fold. Day two, amplified DNA was fragmented ~300-600 bp, then precipitated and resuspended followed by hybridization on to a BeadChip. Single base extension utilizes a single probe sequence ~50 bp long designed to hybridize immediately adjacent to the SNP query site. Following targeted hybridization to the bead array, the arrayed SNP locus-specific primers (attached to beads) were extended with a single hapten-labeled dideoxynucleotide in the SBE reaction. The haptens were subsequently detected by a multi-layer immunohistochemical sandwich assay, as recently described. The Illumina BeadArray Reader scanned each BeadChip at two wavelengths and created an image file. As BeadChip images were collected, intensity values were determined for all instances of each bead type, and data files were created that summarized intensity values for each bead type. These files consisted of intensity data that was loaded directly into Illumina's genotype analysis software, BeadStudio. A bead pool manifest created from the LIMS database containing all the BeadChip data was loaded into BeadStudio along with the intensity data for the samples. BeadStudio used a normalization algorithm to minimize BeadChip to BeadChip variability. Once the normalization was complete, the clustering algorithm was run to evaluate cluster positions for each locus and assign individual genotypes. Each locus was given an overall score based on the quality of the clustering and each individual genotype call was given a GenCall score. GenCall scores provided a quality metric that ranges from 0 to 1 assigned to every genotype called. GenCall scores were then calculated using information from the clustering of the samples. The location of each genotype relative to its assigned cluster determined its GenCall score.

Gene Array Analysis.

Figure 1B:
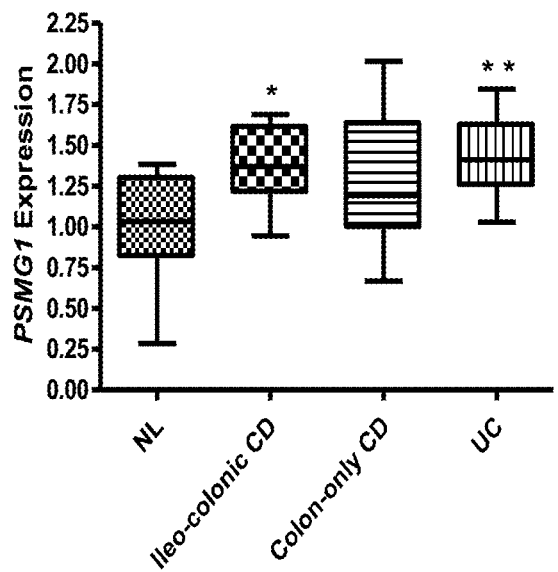
FIG. 1B: Colonic PSMG1 and DSCAM Expression. Colon biopsies were obtained from healthy controls (n=11), and affected segments for CD patients with ileo-colonic (n=18) or colon-only (n=14) location and UC patients (n=10). RNA was prepared and the global pattern of gene expression was determined using the Affymetrix GeneChip Human Genome HG-U133 Plus 2.0 array. Results for A) PSMG1, and B) DSCAM are shown. *p=0.004, **p=0.003 vs. control.
Figure 1B:
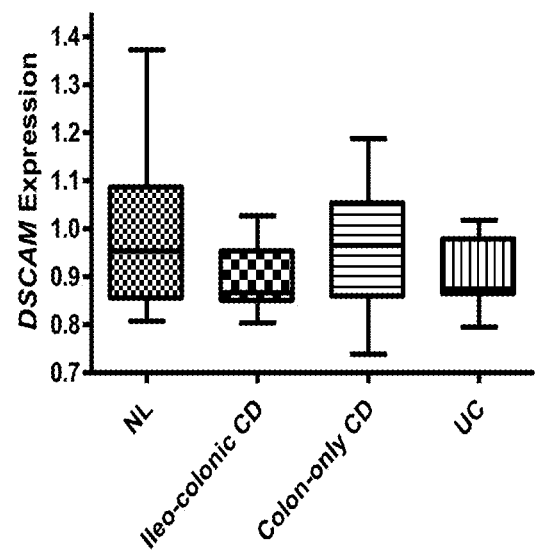
Figure 2:
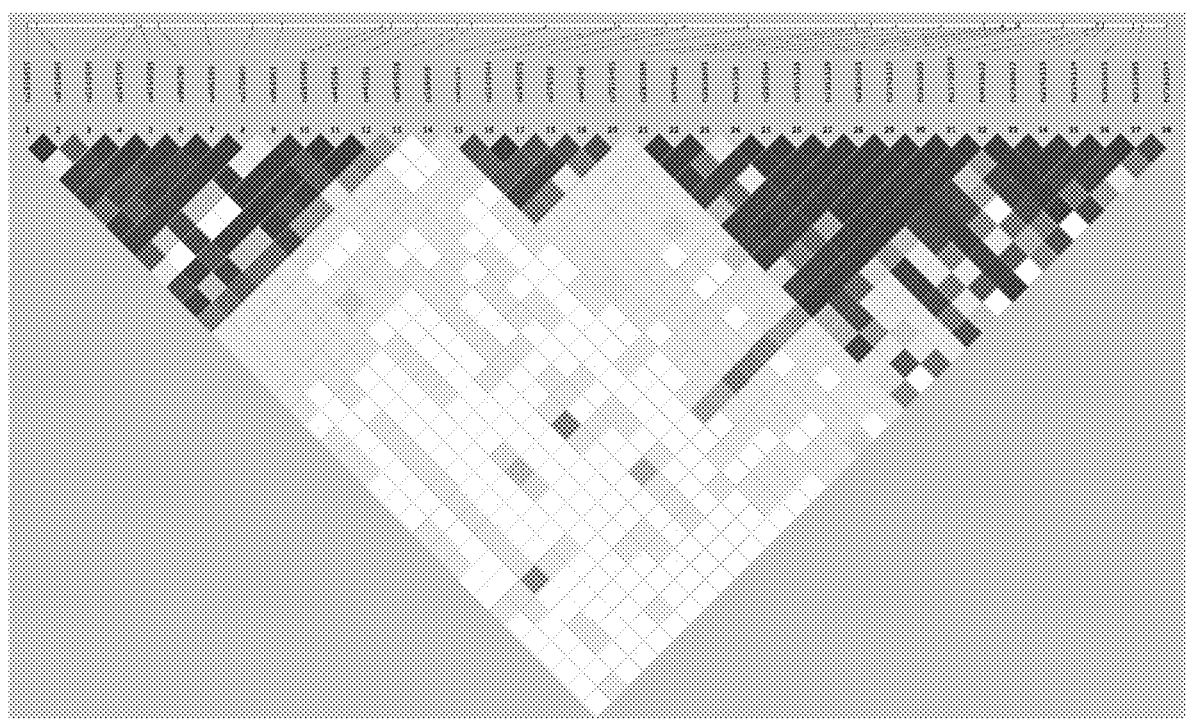
FIG. 2. Linkage disequilibrium (D') between SNPs at the 21q22 locus in the control cohort together. The association signal resides in a region of LD that harbors no genes; however, PSMG1 represents the nearest gene geographically.

The global pattern of gene expression in colon was determined in the Microarray Core of the CCHMC Digestive Health Center REF: PMID: 18069684. Following informed consent, colonic biopsies were obtained from pediatric patients with CD and UC and healthy controls. For CD and UC patients, biopsies were obtained from an area of active disease in the ascending colon or the most proximal area of active disease if the ascending colon was endoscopically normal. Colon biopsies were immediately placed in RNAlater stabilization reagent (Qiagen, Germany) at 4° C. Total RNA was isolated using the RNeasy Plus Mini Kit (Qiagen) and stored at −80° C. Samples where then submitted to the CCHMC Digestive Health Center Microarray Core where the quality and concentration of RNA was measured by the Agilent Bioanalyser 2100 (Hewlett Packard) using the RNA 6000 Nano Assay to confirm a 28S/18S ratio of 1.6-2.0. 100 ng of total RNA was amplified using Target 1-round Aminoallyl-aRNA Amplification Kit 101 (Epicentre, WI). The biotinylated cRNA was hybridized to Affymetrix GeneChip Human Genome HG-U133 Plus 2.0 arrays, containing probes for approximately 22,634 genes. The images were captured using Affymetrix Genechip Scanner 3000. The complete dataset is available at the NCBI Gene Expression Omnibus on the world wide web at .ncbi.nlm.nih.gov/geo accession number. GeneSpring™ software was used in the CCHMC Digestive Health Center Bioinformatics core to analyze fold changes in gene expression between patient groups and healthy controls. Data were normalized to allow for array to array comparisons, and differences between groups were detected in GeneSpring™ with significance at the 0.05 level relative to healthy control samples. In order to allow for comparison between the IBD sub-groups, mucosal inflammation was quantified in colon biopsies using the Crohn's Disease Histological Index of Severity Results In the IBD case-control analysis, single-marker allele frequencies were compared using $\chi^2$ statistics for all markers. Twelve markers were above the threshold for Bonferroni correction (Table 1), the majority of which were previously reported or in the MHC (driven by UC); however, two markers on chromosome 20q13, rs2315008 and rs4809330, and one marker on chromosome 21q22, rs39387404, were novel. Thus, we have identified two non-coding variants in strong linkage disequilibrium (LD) on 20q13 (rs2315008 allele T and rs4809330 allele A) yielding P-values=6.30× $10^{-8}$ (corrected P=0.032) and P-value=6.95×$10^{-8}$ (corrected P=0.036) respectively and protective odds ratios (OR)=0.74 for both (Table 1). In addition, we have identified one non-coding variant on 21q22 (rs2836878 allele A) yielding P-values=6.01×$10^{-8}$ (corrected P=0.031) and a protective OR=0.73. Since all previously discovered IBD genes are primarily associated with CD, it is important to note that the contribution to these novel signals comes from both UC and CD (Table 2). In addition, these signals replicate in the Wellcome Trust Case Control Consortium (WTCCC)[24] CD dataset as also shown in Table 2. The LD structure for the 20q13 and 21q22 loci pinpointing the associated SNPs and genes within these regions are shown in FIGS. 1 and 2, respectively.

Figure 3:
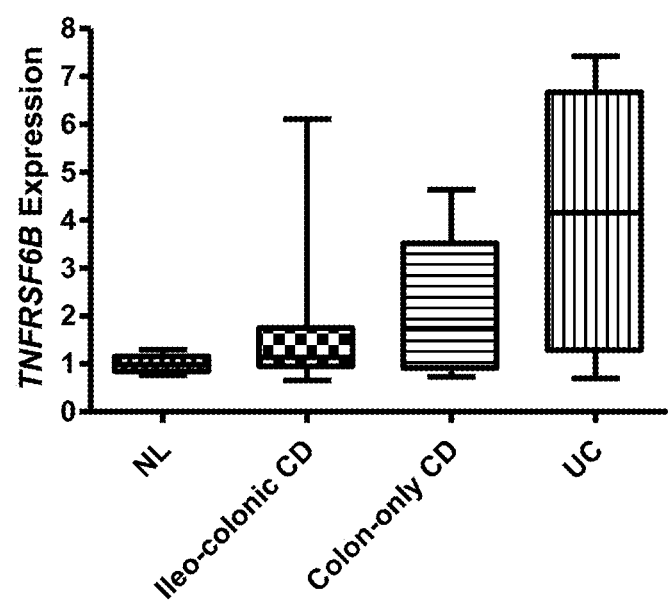
FIG. 3. Colonic TNFRSF6B Expression. Colon biopsies were obtained from healthy controls (n=11, CDHIS: 0), and affected segments for CD patients with ileo-colonic (n=18, mean(SEM) CDHIS: 4.1±0.7) or colon-only (n=14, mean (SEM) CDHIS: 4.9±1) location and UC patients (n=10, mean(SEM) CDHIS: 7.2±0.6, p<0.05 vs. CD groups). RNA was prepared and the global pattern of gene expression was determined using the Affymetrix GeneChip Human Genome HG-U133 Plus 2.0 array. Results for the genes within the telomeric region of LD on 20q13 including A) TNFRSF6B, and B) ARFRP1, LIME1, RTEL1, and ZGPAT are shown. *p=0.01, **p=0.005 vs. control.
Figure 3:
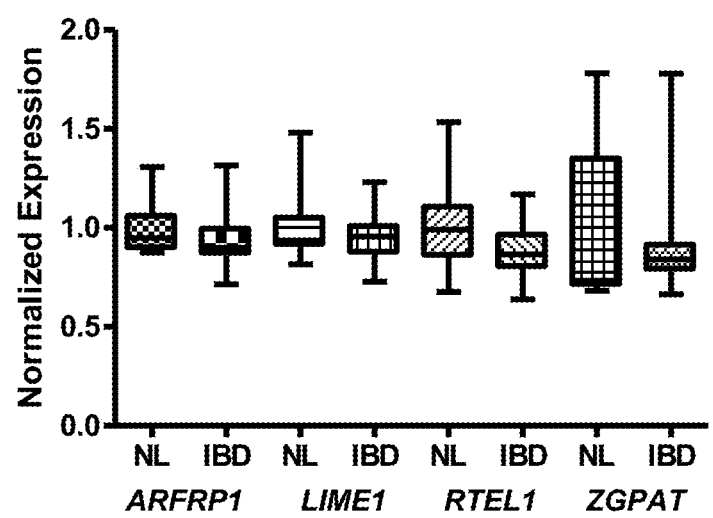

As such, these significant SNPs confer protection from IBD. As shown in FIG. 1, the 20q13 signal resides in a complex telomeric region of LD that harbors the genes for regulator of telomere elongation helicase 1 (RTEL1), tumor necrosis factor receptor superfamily member 6B (TNFRSF6B), ADP-ribosylation factor related protein 1 (ARFRP1), zinc finger CCCH-type with G patch domain (ZGPAT) and Lck interacting transmembrane adaptor 1 (LIME1). The TNFRSF6B gene provides the most compelling candidate based on what is already known about the TNF-pathway in IBD. Indeed, the mRNA expression of TNFRSF6B is markedly different in colonic biopsies obtained from IBD patients compared to disease-free controls; this appears to be associated in part with colon location and with the degree of mucosal inflammation (FIG. 3A, $r^2$=0.24, p=0.001 for linear regression for the Crohn's Disease Histological Index of Severity (CDHIS) and TNFRSF6B expression). While no allelic difference was observed in mRNA expression of TNFRSF6B between IBD subjects with the two identified SNPs, this may have been confounded by a greater degree of mucosal inflammation in the colon biopsies for the subjects who did not carry the associated alleles (mean(SEM) CDHIS for SNP+:3.7±1 vs. SNP−:7±1.2, p=0.05). By comparison, we observed no difference in the expression of RTEL1, ARFRP1, ZGPAT, or LIME1 between IBD cases and controls (FIG. 3B). The gene product for TNFRSF6B acts as a decoy receptor in preventing FasL induced cell death, and a resistance to FasL dependent apoptosis has previously been shown for T lymphocytes in CD[30].

The 21q22 signal resides in a small region of LD that harbors no genes but the nearest gene is the Down syndrome critical region protein 2 isoform (PSMG1). We observed a modest increase in the colonic expression of PSMG1 between IBD cases and controls (supplemental FIG. 1A). However, this did not vary with either the degree of mucosal inflammation, or carriage of the PSMG1 SNP.

In the case-control analysis of CD alone, single-marker allele frequencies were also compared using $\chi^2$ statistics for all markers. Nine markers were above the threshold for Bonferroni correction. As shown in Table 3, all of these loci have been previously reported in GWA studies[21]. However, when investigating the site specificity of CD in patients [colon only (29%), ileum only (17%) or ileocolonic (54%)], a genome wide significant signal was observed for colon-only CD (Table 4), also on chromosome 21 but approximately 1.4 Mb away from the signal we detected on chromosome 21 for the common form of IBD (Table 1). This new signal resides in DSCAM, a gene that has not previously been linked with CD. DSCAM colonic expression did not differ between IBD cases and controls, within the IBD sub-groups, or as a function of mucosal inflammation (supplemental FIG. 1B).

Thus, we have identified two non-coding variants on 21q22 (rs2837643 allele A and rs16999939 allele T) that are associated with the colonic form of CD, yielding a P-value range=5.69×$10^{-8}$-2.40×$10^{-8}$ and an at-risk OR range=3.29-3.57 (Table 4).

Previous work addressing disease location suggests that both ATG16L1 and CARD15 are involved specifically in inflammation of the ileum[31]. Our results are in keeping with these reports demonstrating that the previously described CARD15 variants (and to a lesser extent, ATG16L1) do not appear to impact on colon-only disease in CD patients and the effects of these variants in CD therefore appear to be limited to the ileal/small intestine form of the disease (Table 5).

In the case-control analysis of UC alone, single-marker allele frequencies were also compared using $\chi^2$ statistics for all markers. Seventeen markers were above the threshold for Bonferroni correction (Table 5). However, the resulting genomic inflation factor for the UC run was not as close to 1 i.e. 1.3; therefore we controlled for cryptic population structure using principle components analysis as implemented in Eigenstrat. As a consequence, four markers remained genome-wide significant, all of which resided in the major histocompatibility complex (MHC) on chromosome 6q21. This reinforces previously suggested MHC associations based on linkage studies' and is the first GWA study to associate UC with specific MHC alleles.

Taken together, we have identified novel susceptibility loci in pediatric onset IBD at 20q13 and 21q22. We also show for the first time a strong association of UC with the MHC on 6q21 and we have refined the association of CARD15 with CD to those subjects only who have ileal involvement.

TABLE 1

IBD case-control association study results for GWA significant markers. Novel signals are indicated in bold

| CHR | SNP | Position (B36) | Minor Allele | MAF Aff | MAF Ctrl | P-value | Bonferonni P | OR | Relevant Gene |
|---|---|---|---|---|---|---|---|---|---|
| 1 | rs11209026 | 67478546 | A | 0.024 | 0.061 | $7.47 \times 10^{-11}$ | $3.84 \times 10^{-5}$ | 0.385 | IL23R |
| 16 | rs5743289 | 49314275 | T | 0.232 | 0.172 | $3.77 \times 10^{-10}$ | 0.00019 | 1.455 | CARD15 |
| 1 | rs11465804 | 67475114 | G | 0.030 | 0.065 | $1.46 \times 10^{-9}$ | 0.00075 | 0.442 | IL23R |
| 6 | rs477515 | 32677669 | T | 0.248 | 0.313 | $1.02 \times 10^{-8}$ | 0.0052 | 0.724 | MHC |
| 6 | rs2516049 | 32678378 | G | 0.248 | 0.313 | $1.06 \times 10^{-8}$ | 0.0054 | 0.724 | MHC |
| 6 | rs9271568 | 32698441 | G | 0.238 | 0.301 | $2.95 \times 10^{-8}$ | 0.015 | 0.724 | MHC |
| 9 | rs6478109 | 116608587 | A | 0.251 | 0.314 | $3.20 \times 10^{-8}$ | 0.016 | 0.733 | TNFSF15 |
| 21 | rs2836878 | 39387404 | A | 0.214 | 0.273 | $6.01 \times 10^{-8}$ | 0.031 | 0.725 | *PSMG1* |
| 20 | rs2315008 | 61814400 | T | 0.250 | 0.311 | $6.30 \times 10^{-8}$ | 0.032 | 0.737 | *TNFRSF6B* |
| 20 | rs4809330 | 61820030 | A | 0.249 | 0.310 | $6.95 \times 10^{-8}$ | 0.036 | 0.738 | *TNFRSF6B* |
| 9 | rs6478108 | 116598524 | C | 0.262 | 0.324 | $8.36 \times 10^{-8}$ | 0.043 | 0.743 | TNFSF15 |
| 16 | rs2076756 | 49314382 | G | 0.317 | 0.258 | $9.65 \times 10^{-8}$ | 0.050 | 1.332 | CARD15 |

TABLE 2

Key signals in CD and UC separately and in the WTCCC CD cohort

| CHR | SNP | Minor Allele | MAF Aff | MAF Ctrl | P-value | OR |
|---|---|---|---|---|---|---|
| | | | CD | | | |
| 20 | rs2315008 | T | 0.252 | 0.311 | $1.84 \times 10^{-5}$ | 0.747 |
| 20 | rs4809330 | A | 0.252 | 0.309 | $2.71 \times 10^{-5}$ | 0.752 |
| 21 | rs2836878 | A | 0.224 | 0.272 | 0.00026 | 0.772 |
| | | | UC | | | |
| 20 | rs2315008 | T | 0.238 | 0.311 | 0.00013 | 0.694 |
| 20 | rs4809330 | A | 0.235 | 0.309 | $8.58 \times 10^{-5}$ | 0.686 |
| 21 | rs2836878 | A | 0.194 | 0.272 | $1.71 \times 10^{-5}$ | 0.643 |

| CHR | SNP | Minor Allele | Location (B36) | P | $r^2$ with signal |
|---|---|---|---|---|---|
| | | | WTCC CD | | |
| 20 | rs6011040 | A | 61807850 | $6.52 \times 10^{-5}$ | 0.96 |
| 21 | rs378108 | G | 39391390 | 0.032 | 0.34 |

TABLE 3

CD case-control association study results for GWA significant markers

| CHR | SNP | Position (B36) | Minor Allele | MAF Aff | MAF Ctrl | P-value | Bonferonni P | OR | Relevant Gene |
|---|---|---|---|---|---|---|---|---|---|
| 16 | rs5743289 | 49314275 | T | 0.257 | 0.172 | $1.21 \times 10^{-13}$ | $6.22 \times 10^{-8}$ | 1.671 | CARD15 |
| 1 | rs11209026 | 67478546 | A | 0.018 | 0.061 | $3.35 \times 10^{-10}$ | 0.00017 | 0.281 | IL23R |
| 2 | rs2241880 | 233848107 | T | 0.396 | 0.488 | $7.63 \times 10^{-10}$ | 0.00039 | 0.687 | ATG16L1 |
| 2 | rs2289472 | 233846979 | A | 0.398 | 0.489 | $1.10 \times 10^{-9}$ | 0.00056 | 0.691 | ATG16L1 |
| 2 | rs13391356 | 233835108 | T | 0.399 | 0.489 | $1.31 \times 10^{-9}$ | 0.00067 | 0.693 | ATG16L1 |
| 16 | rs2076756 | 49314382 | G | 0.338 | 0.258 | $1.88 \times 10^{-9}$ | 0.00097 | 1.465 | CARD15 |
| 2 | rs3792109 | 233849156 | T | 0.399 | 0.488 | $3.41 \times 10^{-9}$ | 0.0018 | 0.699 | ATG16L1 |
| 16 | rs2066843 | 49302700 | T | 0.351 | 0.272 | $3.61 \times 10^{-9}$ | 0.0019 | 1.449 | CARD15 |
| 1 | rs11465804 | 67475114 | G | 0.024 | 0.065 | $7.64 \times 10^{-9}$ | 0.0039 | 0.355 | IL23R |

TABLE 4

SNPs of interest with respect to site-specific CD

| CHR | SNP | Position (B36) | Minor Allele | MAF Aff | MAF Ctrl | P-value | OR | Relevant Gene |
|---|---|---|---|---|---|---|---|---|
| | | | | Colon | | | | |
| 1 | rs11465804 | 67475114 | G | 0.038 | 0.063 | 0.094 | 0.598 | IL23R |
| 1 | rs11209026 | 67478546 | A | 0.025 | 0.059 | 0.015 | 0.405 | IL23R |
| 2 | rs13391356 | 233835108 | T | 0.423 | 0.489 | 0.028 | 0.766 | ATG16L1 |
| 2 | rs2289472 | 233846979 | G | 0.420 | 0.489 | 0.021 | 0.757 | ATG16L1 |
| 2 | rs2241880 | 233848107 | T | 0.419 | 0.488 | 0.022 | 0.757 | ATG16L1 |
| 2 | rs3792109 | 233849156 | C | 0.426 | 0.488 | 0.041 | 0.780 | ATG16L1 |
| 3 | rs2245556 | 102098240 | T | 0.141 | 0.139 | 0.94 | 1.013 | ABI3BP |
| 9 | rs6478108 | 116598524 | C | 0.234 | 0.320 | 0.0022 | 0.651 | TNFSF15 |
| 9 | rs6478109 | 116608587 | A | 0.238 | 0.310 | 0.0091 | 0.694 | TNFSF15 |

TABLE 4-continued

SNPs of interest with respect to site-specific CD

| CHR | SNP | Position (B36) | Minor Allele | MAF Aff | MAF Ctrl | P-value | OR | Relevant Gene |
|---|---|---|---|---|---|---|---|---|
| 16 | rs2066843 | 49302700 | T | 0.325 | 0.273 | 0.052 | 1.283 | CARD15 |
| 16 | rs5743289 | 49314275 | T | 0.185 | 0.173 | 0.59 | 1.088 | CARD15 |
| 16 | rs2076756 | 49314382 | G | 0.294 | 0.260 | 0.20 | 1.186 | CARD15 |
| 20 | rs2315008 | 61814400 | T | 0.280 | 0.306 | 0.35 | 0.882 | TNFRSF6B |
| 20 | rs4809330 | 61820030 | A | 0.280 | 0.304 | 0.37 | 0.888 | TNFRSF6B |
| 21 | rs2836878 | 39387404 | A | 0.231 | 0.266 | 0.18 | 0.828 | PSMG1 |
| 21 | rs2837643 | 40761352 | A | 0.070 | 0.021 | $2.40 \times 10^{-8}$ | 3.567 | DSCAM |
| 21 | rs16999939 | 40828471 | T | 0.077 | 0.025 | $5.69 \times 10^{-8}$ | 3.285 | DSCAM |
| | | | Ileum | | | | | |
| 1 | rs11465804 | 67475114 | G | 0.012 | 0.063 | 0.0083 | 0.187 | IL23R |
| 1 | rs11209026 | 67478546 | A | 0.006 | 0.059 | 0.0045 | 0.099 | IL23R |
| 2 | rs13391356 | 233835108 | T | 0.377 | 0.489 | 0.0045 | 0.631 | ATG16L1 |
| 2 | rs2289472 | 233846979 | G | 0.377 | 0.489 | 0.0047 | 0.632 | ATG16L1 |
| 2 | rs2241880 | 233848107 | T | 0.375 | 0.488 | 0.0046 | 0.630 | ATG16L1 |
| 2 | rs3792109 | 233849156 | C | 0.377 | 0.488 | 0.0050 | 0.635 | ATG16L1 |
| 3 | rs2245556 | 102098240 | T | 0.173 | 0.139 | 0.22 | 1.291 | ABI3BP |
| 9 | rs6478108 | 116598524 | C | 0.303 | 0.320 | 0.64 | 0.923 | TNFSF15 |
| 9 | rs6478109 | 116608587 | A | 0.296 | 0.310 | 0.71 | 0.937 | TNFSF15 |
| 16 | rs2066843 | 49302700 | T | 0.364 | 0.273 | 0.010 | 1.525 | CARD15 |
| 16 | rs5743289 | 49314275 | T | 0.315 | 0.173 | $2.50 \times 10^{-6}$ | 2.198 | CARD15 |
| 16 | rs2076756 | 49314382 | G | 0.364 | 0.260 | 0.0027 | 1.634 | CARD15 |
| 20 | rs2315008 | 61814400 | T | 0.191 | 0.306 | 0.0017 | 0.538 | TNFRSF6B |
| 20 | rs4809330 | 61820030 | A | 0.191 | 0.304 | 0.0019 | 0.541 | TNFRSF6B |
| 21 | rs2836878 | 39387404 | A | 0.228 | 0.266 | 0.28 | 0.817 | PSMG1 |
| 21 | rs2837643 | 40761352 | A | 0.051 | 0.021 | 0.0094 | 2.530 | DSCAM |
| 21 | rs16999939 | 40828471 | T | 0.062 | 0.025 | 0.0030 | 2.593 | DSCAM |
| | | | Ileocolonic | | | | | |
| 1 | rs11465804 | 67475114 | G | 0.023 | 0.063 | 0.00029 | 0.345 | IL23R |
| 1 | rs11209026 | 67478546 | A | 0.020 | 0.059 | 0.00037 | 0.335 | IL23R |
| 2 | rs13391356 | 233835108 | T | 0.406 | 0.489 | 0.00033 | 0.713 | ATG16L1 |
| 2 | rs2289472 | 233846979 | G | 0.406 | 0.489 | 0.00036 | 0.715 | ATG16L1 |
| 2 | rs2241880 | 233848107 | T | 0.402 | 0.488 | 0.00025 | 0.706 | ATG16L1 |
| 2 | rs3792109 | 233849156 | C | 0.406 | 0.488 | 0.00042 | 0.717 | ATG16L1 |
| 3 | rs2245556 | 102098240 | T | 0.180 | 0.139 | 0.011 | 1.359 | ABI3BP |
| 9 | rs6478108 | 116598524 | C | 0.254 | 0.320 | 0.0024 | 0.725 | TNFSF15 |
| 9 | rs6478109 | 116608587 | A | 0.238 | 0.310 | 0.00073 | 0.694 | TNFSF15 |
| 16 | rs2066843 | 49302700 | T | 0.355 | 0.273 | $9.01 \times 10^{-5}$ | 1.462 | CARD15 |
| 16 | rs5743289 | 49314275 | T | 0.271 | 0.173 | $3.93 \times 10^{-8}$ | 1.774 | CARD15 |
| 16 | rs2076756 | 49314382 | G | 0.344 | 0.260 | $3.53 \times 10^{-5}$ | 1.497 | CARD15 |
| 20 | rs2315008 | 61814400 | T | 0.258 | 0.306 | 0.026 | 0.791 | TNFRSF6B |
| 20 | rs4809330 | 61820030 | A | 0.258 | 0.304 | 0.031 | 0.796 | TNFRSF6B |
| 21 | rs2836878 | 39387404 | A | 0.236 | 0.266 | 0.14 | 0.851 | PSMG1 |
| 21 | rs2837643 | 40761352 | A | 0.016 | 0.021 | 0.53 | 0.794 | DSCAM |
| 21 | rs16999939 | 40828471 | T | 0.027 | 0.025 | 0.79 | 1.079 | DSCAM |

TABLE 5

UC case-control association study results for GWA significant markers

| CHR | SNP | Position (B36) | Minor Allele | MAF Aff | MAF Ctrl | P-value | Bonferonni P | OR | Relevant Gene | Eigenstrat P |
|---|---|---|---|---|---|---|---|---|---|---|
| 6 | rs9271568 | 32698441 | A | 0.148 | 0.301 | $8.22 \times 10^{-16}$ | $4.22 \times 10^{-10}$ | 0.402 | MHC | $5.21 \times 10^{-10}$ |
| 6 | rs2516049 | 32678378 | G | 0.167 | 0.313 | $1.17 \times 10^{-14}$ | $6.02 \times 10^{-9}$ | 0.440 | MHC | $4.20 \times 10^{-10}$ |
| 6 | rs477515 | 32677669 | T | 0.167 | 0.313 | $1.24 \times 10^{-14}$ | $6.36 \times 10^{-9}$ | 0.440 | MHC | $4.45 \times 10^{-10}$ |
| 6 | rs2395185 | 32541145 | T | 0.177 | 0.325 | $1.97 \times 10^{-14}$ | $1.01 \times 10^{-8}$ | 0.447 | MHC | $1.06 \times 10^{-9}$ |
| 6 | rs3104404 | 32790152 | A | 0.353 | 0.230 | $3.10 \times 10^{-12}$ | $1.59 \times 10^{-6}$ | 1.823 | MHC | |
| 6 | rs3129882 | 32517508 | G | 0.579 | 0.452 | $5.76 \times 10^{-10}$ | 0.00030 | 1.670 | MHC | |
| 6 | rs6903608 | 32536263 | C | 0.445 | 0.328 | $1.71 \times 10^{-9}$ | 0.00088 | 1.644 | MHC | |
| 6 | rs3129763 | 32698903 | A | 0.374 | 0.264 | $1.80 \times 10^{-9}$ | 0.00093 | 1.667 | MHC | |
| 6 | rs602875 | 32681607 | G | 0.377 | 0.268 | $3.75 \times 10^{-9}$ | 0.0019 | 1.650 | MHC | |
| 6 | rs382259 | 32317005 | G | 0.429 | 0.317 | $6.93 \times 10^{-9}$ | 0.0036 | 1.617 | MHC | |
| 3 | rs2245556 | 102098240 | T | 0.063 | 0.145 | $8.34 \times 10^{-9}$ | 0.0043 | 0.396 | ABI3BP | |
| 6 | rs660895 | 32685358 | G | 0.101 | 0.188 | $4.39 \times 10^{-8}$ | 0.023 | 0.485 | MHC | |
| 3 | rs2595893 | 102160532 | C | 0.066 | 0.144 | $4.44 \times 10^{-8}$ | 0.023 | 0.421 | ABI3BP | |
| 6 | rs1035798 | 32259200 | T | 0.375 | 0.274 | $4.57 \times 10^{-8}$ | 0.023 | 1.591 | MHC | |
| 3 | rs2245473 | 102098826 | G | 0.064 | 0.142 | $4.64 \times 10^{-8}$ | 0.024 | 0.414 | ABI3BP | |
| 4 | rs7663239 | 38462245 | G | 0.125 | 0.068 | $7.50 \times 10^{-8}$ | 0.039 | 1.965 | TLR1 | |
| 6 | rs3135363 | 32497626 | C | 0.391 | 0.290 | $8.32 \times 10^{-8}$ | 0.043 | 1.571 | MHC | |

Example 2

We report herein results of an on-going GWA study where we genotyped 550,000 single nucleotide polymorphisms (SNPs) with the Illumina Human Hap550 Genotyping BeadChip[29] in our study population of 2,161 IBD cases of European ancestry and 6,483 controls with matching ancestry (based on self report). Self-reported Caucasian ethnicity proved to be accurate, as the resulting genomic inflation factor for the IBD run was less than 1.07.

The following materials and methods are provided to facilitate the practice of the present example.

Research Subjects

1. IBD Cohort

Subject Ascertainment and Diagnostic Classification.

Affected individuals with pediatric onset IBD (both CD and UC) were ascertained through the Children's Hospital of Wisconsin and Medical College of Wisconsin, Children's Hospital of Philadelphia, Cincinnati Children's Hospital Medical Center, University of Edinburgh; Sapienza University of Rome, Italy; Casa Sollievo della Sofferenza" Hospital San Giovanni Rotondo, Italy; Mount Sinai Hospital Toronto; Hospital for Sick Children, Toronto; Cedars-Sinai Medical Ctr in Los Angeles. In addition, colonic mucosal biopsies from affected IBD patients were obtained from Cincinnati Children's Medical center and from Children's Hospital of Wisconsin during the diagnostic endoscopic procedures. Only subjects of European ancestry were used in the final analysis which consisted of 2,161 individuals with IBD where the age of onset for IBD was before their $19^{th}$ birthday. All subjects had genotypes with call rates above 95%. Informed consent was obtained from all participants, and protocols were approved by the local institutional review board in all participating institutions. The diagnosis of IBD was made after fulfilling standard criteria (ref) across the participating centers that requires (i) one or more of the following symptoms: diarrhea, rectal bleeding, abdominal pain, fever or complicated perianal disease; (ii) occurrence of symptoms on two or more occasions separated by at least 8 weeks or ongoing symptoms of at least 6 weeks' duration and (iii) objective evidence of inflammation from radiologic, endoscopic, video capsule endoscopy. Histological evidence of IBD[33] was considered mandatory for the diagnosis of CD or UC and inclusion in the study.

Phenotypic classification was based on the Montreal classification[37]. For CD we defined disease location based on each subject's all available endoscopic and radiographic evaluation. Based on macroscopic evidence of disease location, we classified each subject by the following: Ileum only: disease of the small bowel proximal to the cecum and distal $4^{th}$ portion of duodenum; Colon only: any colonic location between cecum and rectum with no small bowel disease; Ileocolonic: disease of the small bowel and any location between cecum and rectum. In addition, any of the above categories may have upper GI tract involvement: disease involving esophagus, stomach, duodenum and perianal disease including: perianal fistulae, perianal and anal lesions including more than single skin tags and anal ulcers. For example, subjects with ileal only, colonic only or ileocolonic disease may also have concomitant upper tract and/or perianal disease.

2. Control Subjects from Philadelphia

The control group included 6,483 children with self reported Caucasian status, mean age 9.5 years; 53.0% male and 47.0% female, who did not have IBD (CD or UC). These individual were recruited by CHOP clinicians and nursing staff within the CHOP Health Care Network, including four primary care clinics and several group practices and outpatient practices that included well child visits. The Research Ethics Board of CHOP approved the study, and written informed consent was obtained from all subjects.

Genotyping

Illumina Infinium™ Assay:

We performed high throughput genome-wide SNP genotyping, using the Illumina Infinium™ II HumanHap550 BeadChip technology[29,35] (Illumina, San Diego), at the Center for Applied Genomics at CHOP. We used 750 ng of genomic DNA to genotype each sample, according to the manufacturer's guidelines. On day one, genomic DNA was amplified 1000-1500-fold. Day two, amplified DNA was fragmented ~300-600 bp, then precipitated and resuspended followed by hybridization on to a BeadChip. Single base extension utilizes a single probe sequence ~50 bp long designed to hybridize immediately adjacent to the SNP query site. Following targeted hybridization to the bead array, the arrayed SNP locus-specific primers (attached to beads) were extended with a single hapten-labeled dideoxynucleotide in the SBE reaction. The haptens were subsequently detected by a multi-layer immunohistochemical sandwich assay, as recently described. The Illumina BeadArray Reader scanned each BeadChip at two wavelengths and created an image file. As BeadChip images were collected, intensity values were determined for all instances of each bead type, and data files were created that summarized intensity values for each bead type. These files consisted of intensity data that was loaded directly into Illumina's genotype analysis software, BeadStudio. A bead pool manifest created from the LIMS database containing all the BeadChip data was loaded into BeadStudio along with the intensity data for the samples. BeadStudio used a normalization algorithm to minimize BeadChip to BeadChip variability. Once the normalization was complete, the clustering algorithm was run to evaluate cluster positions for each locus and assign individual genotypes. Each locus was given an overall score based on the quality of the clustering and each individual genotype call was given a GenCall score. GenCall scores provided a quality metric that ranges from 0 to 1 assigned to every genotype called. GenCall scores were then calculated using information from the clustering of the samples. The location of each genotype relative to its assigned cluster determined its GenCall score.

Gene Array Analysis.

The global pattern of gene expression in colon was determined in the Microarray Core of the CCHMC Digestive Health Center REF: PMID: 18069684. Following informed consent, colonic biopsies were obtained from pediatric patients with CD and UC and healthy controls. For CD and UC patients, biopsies were obtained from an area of active disease in the ascending colon or the most proximal area of active disease if the ascending colon was endoscopically normal. Colon biopsies were immediately placed in RNAlater stabilization reagent (Qiagen, Germany) at 4° C. Total RNA was isolated using the RNeasy Plus Mini Kit (Qiagen) and stored at −80° C. Samples where then submitted to the CCHMC Digestive Health Center Microarray Core where the quality and concentration of RNA was measured by the Agilent Bioanalyser 2100 (Hewlett Packard) using the RNA 6000 Nano Assay to confirm a 28S/18S ratio of 1.6-2.0. 100 ng of total RNA was amplified using Target 1-round Aminoallyl-aRNA Amplification Kit 101 (Epicentre, WI). The biotinylated cRNA was hybridized to Affymetrix GeneChip Human Genome HG-U133 Plus 2.0 arrays, containing probes for approximately 22,634 genes. The images were captured using Affymetrix Genechip Scanner 3000. The complete dataset is available at the NCBI Gene Expression Omnibus on the world wide web at ncbi.nlm.nih.gov/geo accession number. GeneSpring™ software was used in the CCHMC Digestive Health Center Bioinformatics core to analyze fold changes in gene expression between patient groups and healthy controls. Data were normalized to allow for array to array comparisons, and differences between groups were detected in GeneSpring™ with significance at the 0.05 level relative to healthy control samples. In order to allow for comparison between the IBD sub-groups, mucosal inflammation was quantified in colon biopsies using the Crohn's Disease Histological Index of Severity.

Results

Following a genome wide association analysis in an IBD cohort, we observe a constellation of novel significant loci associating with IBD (Table 6), CD (Table 7), and UC (Table 8). This invention consists of the genetic factors listed in the tables below. Regions highlighted in gray color in Tables 6-8 are genes/loci that are genome-wide significant ($P<10^{-8}$). Other regions include genes/loci that are suggestive of causality of IBD ($P<10^{-5}$).

TABLE 6

A. Genetic Factors involved in IBD (all)

| REGION | COORDS | SNP | P | F_A | F_U | OR | Genes |
|---|---|---|---|---|---|---|---|
| 1 | chr3: 49151994-50224828 | rs4625 | 1.70E-11 | 0.3669 | 0.3111 | 1.283 | BSN, DAG1 |
| 2 | chr10: 101262355-101314545 | rs11190140 | 6.04E-10 | 0.4527 | 0.5075 | 0.8027 | NKX2-3 |
| 3 | chr4: 114760869-114783182 | rs10488959 | 1.45E-09 | 0.02758 | 0.05024 | 0.5363 | CAMK2D |
| 4 | chr22: 45052867-45109522 | rs1108458 | 5.18E-09 | 0.00223 | 0.01292 | 0.1708 | FLJ20699, GTSE1, PKDREJ, PPARA |
| 5 | chr21: 39385048-39430485 | rs2836878 | 6.81E-09 | 0.2227 | 0.2675 | 0.7845 | |
| 6 | chr5: 40353763-40660706 | rs7720838 | 7.43E-09 | 0.3777 | 0.4282 | 0.8106 | |
| 7 | chr22: 31440214-31524544 | rs16991082 | 1.18E-08 | 0.03439 | 0.05721 | 0.5869 | SYN3 |
| 8 | chr19: 1853612-2056962 | rs11671391 | 1.57E-08 | 0.1175 | 0.1541 | 0.7308 | AP3D1, C19orf36, MOBKL2A |
| 9 | chr21: 44434378-44442169 | rs762421 | 4.15E-07 | 0.4243 | 0.3801 | 1.202 | C21orf33, ICOSLG |
| 10 | chr20: 61738386-61822030 | rs2315008 | 4.26E-07 | 0.2735 | 0.3147 | 0.8198 | ARFRP1, LIME1, RTEL1, SLC2A4RG, TNFRSF6B, ZBTB46, ZGPAT |
| 11 | chr10: 35338629-35596060 | rs12261843 | 5.08E-07 | 0.3276 | 0.2869 | 1.211 | CCNY |
| 12 | chr16: 28445349-28541086 | rs1968752 | 5.78E-07 | 0.3873 | 0.3449 | 1.201 | CCDC101, LOC440350, SULT1A1, SULT1A2 |
| 13 | chr17: 29551272-29718300 | rs17809115 | 8.02E-07 | 0.1282 | 0.1595 | 0.7746 | CCL11, CCL2, CCL7, CCL8 |
| 14 | chr1: 210803532-210815740 | rs2137424 | 1.26E-06 | 0.3076 | 0.3483 | 0.8314 | ATF3 |
| 15 | chr14: 68568805-68774911 | rs2056153 | 1.28E-06 | 0.2916 | 0.3317 | 0.8294 | WDR22 |
| 16 | chr9: 138384317-138526716 | rs4077515 | 1.37E-06 | 0.4512 | 0.4088 | 1.189 | CARD9, GPSM1, LOC728489, PMPCA, SDCCAG3, SNAPC4 |
| 17 | chr9: 4969602-4992811 | rs10758669 | 1.42E-06 | 0.3868 | 0.3458 | 1.193 | JAK2 |
| 18 | chr3: 48729516-48810619 | rs11713694 | 1.55E-06 | 0.1286 | 0.1021 | 1.298 | PRKAR2A |
| 19 | chr22: 28751460-28861631 | rs2412973 | 2.61E-06 | 0.4979 | 0.4564 | 1.181 | HORMAD2 |
| 20 | chr14: 87543757-87549635 | rs3742704 | 3.61E-06 | 0.1097 | 0.08599 | 1.31 | GALC, GPR65 |
| 21 | chr2: 167961916-168008207 | rs1159502 | 4.02E-06 | 0.06468 | 0.08777 | 0.7187 | |
| 22 | chr8: 126597712-126614204 | rs1551398 | 4.49E-06 | 0.3454 | 0.3847 | 0.8438 | |
| 23 | chr12: 85716641-85786744 | rs17370612 | 4.57E-06 | 0.346 | 0.3082 | 1.187 | MGAT4C |
| 24 | chr17: 8805976-8813253 | rs511973 | 5.45E-06 | 0.1281 | 0.1568 | 0.7899 | PIK3R5 |
| 25 | chr16: 28743016-28808294 | rs8049439 | 5.64E-06 | 0.4129 | 0.3738 | 1.178 | ATXN2L, SH2B1, TUFM |
| 26 | chr1: 153459604-153529007 | rs1052176 | 6.36E-06 | 0.2748 | 0.2401 | 1.199 | ASH1L, C1orf104, C1orf2, CLK2, FDPS, GBA, HCN3, PKLR, RUSC1, SCAMP3 |
| 27 | chr5: 131441960-131849820 | rs2548993 | 6.44E-06 | 0.222 | 0.2565 | 0.8272 | IRF1, LOC441108 |
| 28 | chr17: 35173785-35317722 | rs2872507 | 7.06E-06 | 0.4955 | 0.4558 | 1.173 | GSDML, IKZF3, ORMDL3, ZPBP2 |
| 29 | chr20: 48328611-48416077 | rs4811050 | 7.26E-06 | 0.1393 | 0.1687 | 0.7976 | |

B. Genetic Factors involved in IBD (subset)

| REGION | COORDS | NumSNP | TopSNP | TopP | F_A | F_U | OR | Genes |
|---|---|---|---|---|---|---|---|---|
| 1 | chr6: 90682173-90715742 | 2 | rs13219796 | 7.71E-24 | 0.01823 | 0.07632 | 0.2247 | BACH2, CASP8AP2, CX62, MDN1 |
| 2 | chr1: 60475371-60663807 | 2 | rs4529739 | 2.25E-22 | 0.0291 | 0.09168 | 0.2969 | C1orf87 |
| 3 | chr7: 36949937-37046283 | 2 | rs17170842 | 4.71E-18 | 0.03079 | 0.08376 | 0.3475 | ELMO1 |
| 4 | chr7: 55627351-55634120 | 2 | rs13232099 | 4.64E-16 | 0.02811 | 0.07495 | 0.357 | ECOP, FKBP9L, LANCL2, SEPT14 |
| 5 | chr2: 167961916-168008207 | 2 | rs1159502 | 2.82E-14 | 0.0376 | 0.08476 | 0.4218 | XIRP2 |
| 7 | chr1: 243688674-243819452 | 2 | rs11585347 | 5.16E-09 | 0.04142 | 0.07594 | 0.5258 | KIF26B |
| 8 | chr2: 227770223-227901446 | 2 | rs6722598 | 1.17E-08 | 0.01548 | 0.03929 | 0.3846 | C2orf33, COL4A3, COL4A4, HRB, TM4SF20 |
| 9 | chr9: 116561013-116610587 | 4 | rs10759736 | 1.63E-08 | 0.0753 | 0.1155 | 0.6239 | ATP6V1G1, C9orf91, TNFSF15, TNFSF8 |

TABLE 6-continued

| | | | | | | | |
|---|---|---|---|---|---|---|---|
| 10 | chr20: 865094-876945 | 2 | rs474816 | 2.76E−08 | 0.09732 | 0.1419 | 0.6521 ANGPT4, C20orf54, FAM110A, PSMF1, RSPO4 |
| 11 | chr18: 22546376-22715449 | 3 | rs1597317 | 4.12E−08 | 0.1893 | 0.247 | 0.7116 AQP4, CHST9, KCTD1 |
| 12 | chr4: 22776952-22855172 | 2 | rs7676830 | 9.86E−08 | 0.2053 | 0.2599 | 0.7355 |
| 15 | chr3: 125487920-125642496 | 2 | rs13098182 | 3.90E−07 | 0.04705 | 0.07668 | 0.5945 KALRN |
| 16 | chr8: 81852567-81966154 | 2 | rs17475446 | 8.47E−07 | 0.108 | 0.1476 | 0.6994 PAG1, ZNF704 |
| 17 | chr7: 45911451-46082359 | 2 | rs12671457 | 9.27E−07 | 0.1147 | 0.1546 | 0.7084 ADCY1, IGFBP1, IGFBP3 |

TABLE 7

Genetic Factors involved in Crohn's Disease

| REGION | COORDS | SNP | P | F_A | F_U | OR | Genes |
|---|---|---|---|---|---|---|---|
| 1 | chr5: 40353763-40660810 | rs13163402 | 3.43E−12 | 0.2461 | 0.3091 | 0.7297 | |
| 2 | chr3: 49151994-50179235 | rs4625 | 4.90E−09 | 0.3686 | 0.3139 | 1.276 | BSN, DAG1 |
| 3 | chr5: 131441960-131894051 | rs2548993 | 5.55E−09 | 0.2036 | 0.2531 | 0.7542 | IRF1, LOC441108 |
| 4 | chr4: 114760869-114783182 | rs10488959 | 1.38E−08 | 0.02694 | 0.05069 | 0.5185 | CAMK2D |
| 6 | chr1: 171079478-171132571 | rs12037853 | 1.11E−07 | 0.2887 | 0.2426 | 1.267 | |
| 7 | chr16: 28445349-28541086 | rs1968752 | 6.42E−07 | 0.3889 | 0.3414 | 1.228 | CCDC101, LOC440350, SULT1A1, SULT1A2 |
| 8 | chr7: 25342013-25370962 | rs11764103 | 1.01E−06 | 0.299 | 0.2558 | 1.241 | |
| 9 | chr10: 64048342-64138808 | rs10995239 | 1.18E−06 | 0.424 | 0.3768 | 1.218 | ZNF365 |
| 10 | chr14: 87543757-87549635 | rs3742704 | 2.18E−06 | 0.1094 | 0.08241 | 1.368 | GALC, GPR65 |
| 11 | chr22: 45052867-45109522 | rs1108458 | 2.26E−06 | 0.002405 | 0.0115 | 0.2073 | FLJ20699, GTSE1, PKDREJ, PPARA |
| 12 | chr9: 4969602-5140278 | rs10758669 | 2.26E−06 | 0.3913 | 0.3461 | 1.214 | JAK2 |
| 13 | chr10: 80705235-80732323 | rs1250552 | 2.65E−06 | 0.4118 | 0.4585 | 0.827 | PPIF, ZMIZ1 |
| 14 | chr10: 101262355-101312110 | rs11190140 | 4.06E−06 | 0.452 | 0.4978 | 0.8319 | NKX2-3 |
| 15 | chr9: 138384317-138411646 | rs10781500 | 4.16E−06 | 0.4493 | 0.4033 | 1.207 | CARD9, GPSM1, LOC728489, PMPCA, SDCCAG3, SNAPC4 |
| 16 | chr9: 72306484-72313143 | rs10868841 | 6.98E−06 | 0.3065 | 0.3488 | 0.8251 | TRPM3 |
| 17 | chr17: 16861037-17023300 | rs16961396 | 7.31E−06 | 0.03594 | 0.02181 | 1.672 | FLCN, LOC201164, M-RIP |
| 18 | chr8: 128239868-128282411 | rs2456449 | 8.46E−06 | 0.298 | 0.3397 | 0.8253 | |
| 19 | chr21: 44434378-44441989 | rs762421 | 8.79E−06 | 0.4254 | 0.3816 | 1.199 | C21orf33, ICOSLG |

TABLE 8

Genetic Factors involved in Ulcerative Colitis

| REGION | COORDS | SNP | P | F_A | F_U | OR | Genes |
|---|---|---|---|---|---|---|---|
| 1 | chr18: 32218133-32251233 | rs7228236 | 1.17E−06 | 0.1697 | 0.2284 | 0.6904 | FHOD3 |
| 2 | chr21: 39385048-39389404 | rs2836878 | 3.89E−06 | 0.2042 | 0.2631 | 0.7188 | |

IBD is a major health problem in children and an immense economic burden on the health care systems both in the US and the rest of the world. The GWA approach serves the critical need for a more comprehensive and unbiased strategy to identify causal genes related to IBD. The human genome and International HapMap projects have enabled the development of unprecedented technology and tools to investigate the genetic basis of complex disease. The HapMap project, a large-scale effort aimed at understanding human sequence variation, has yielded new insights into human genetic diversity that is essential for the rigorous study design needed to maximize the likelihood that a genetic association study will be successful. Genome-wide genotyping of over 500,000 SNPs can now be readily achieved in an efficient and highly accurate manner. Since much of human diversity is due to single base pair variations together with variations in copy number throughout the genome, current advances in single-base extension (SBE) biochemistry and hybridization/detection to synthetic oligonucleotides now make it possible to accurately genotype and quantitate allelic copy number. Accordingly, this project has applied the latest in high density SNP-based genotyping technology in GWA studies aimed at identifying genes and genetic variants that contribute to IBD in well-defined pediatric study populations. Our invention is a discovery that impacts on millions of children in the US and the rest of the world with IBD.

REFERENCES FOR EXAMPLES I AND II

1. Schreiber, S., Rosenstiel, P., Albrecht, M., Hampe, J. & Krawczak, M. Genetics of Crohn disease, an archetypal inflammatory barrier disease. *Nat Rev Genet* 6, 376-88 (2005).
2. Bouma, G. & Strober, W. The immunological and genetic basis of inflammatory bowel disease. *Nat Rev Immunol* 3, 521-33 (2003).
3. Sartor, R. B. Mechanisms of disease: pathogenesis of Crohn's disease and ulcerative colitis. *Nat Clin Pract Gastroenterol Hepatol* 3, 390-407 (2006).
4. Podolsky, D. K. Inflammatory bowel disease. *N Engl J Med* 347, 417-29 (2002).

5. Halme, L. et al. Family and twin studies in inflammatory bowel disease. *World J Gastroenterol* 12, 3668-72 (2006).
6. Orholm, M. et al. Familial occurrence of inflammatory bowel disease. *N Engl J Med* 324, 84-8 (1991).
7. Peeters, M. et al. Familial aggregation in Crohn's disease: increased age-adjusted risk and concordance in clinical characteristics. *Gastroenterology* 111, 597-603 (1996).
8. Yang, H. et al. Familial empirical risks for inflammatory bowel disease: differences between Jews and non-Jews. *Gut* 34, 517-24 (1993).
9. Orholm, M., Binder, V., Sorensen, T. I., Rasmussen, L. P. & Kyvik, K. O. Concordance of inflammatory bowel disease among Danish twins. Results of a nationwide study. *Scand J Gastroenterol* 35, 1075-81 (2000).
10. Annese, V. et al. Familial expression of anti-*Saccharomyces cerevisiae* Mannan antibodies in Crohn's disease and ulcerative colitis: a GISC study. *Am J Gastroenterol* 96, 2407-12 (2001).
11. Bayless, T. M. Maintenance therapy for Crohn's disease. *Gastroenterology* 110, 299-302 (1996).
12. Peeters, M., Cortot, A., Vermeire, S. & Colombel, J. F. Familial and sporadic inflammatory bowel disease: different entities? *Inflamm Bowel Dis* 6, 314-20 (2000).
13. Mathew, C. G. & Lewis, C. M. Genetics of inflammatory bowel disease: progress and prospects. *Hum Mol Genet* 13 Spec No 1, R161-8 (2004).
14. Hugot, J. P. et al. Association of NOD2 leucine-rich repeat variants with susceptibility to Crohn's disease. *Nature* 411, 599-603 (2001).
15. Ogura, Y. et al. A frameshift mutation in NOD2 associated with susceptibility to Crohn's disease. *Nature* 411, 603-6 (2001).
16. Hampe, J. et al. Association between insertion mutation in NOD2 gene and Crohn's disease in German and British populations. *Lancet* 357, 1925-8 (2001).
17. Rioux, J. D. et al. Genetic variation in the 5q31 cytokine gene cluster confers susceptibility to Crohn disease. *Nat Genet* 29, 223-8 (2001).
18. Mirza, M. M. et al. Genetic evidence for interaction of the 5q31 cytokine locus and the CARD15 gene in Crohn disease. *Am J Hum Genet* 72, 1018-22 (2003).
19. Peltekova, V. D. et al. Functional variants of OCTN cation transporter genes are associated with Crohn disease. *Nat Genet* 36, 471-5 (2004).
20. Duerr, R. H. et al. A genome-wide association study identifies IL23R as an inflammatory bowel disease gene. *Science* 314, 1461-3 (2006).
21. Baldassano, R. N. et al. Association of Variants of the Interleukin-23 Receptor Gene With Susceptibility to Pediatric Crohn's Disease. *Clin Gastroenterol Hepatol* 5, 972-976 (2007).
22. Hampe, J. et al. A genome-wide association scan of nonsynonymous SNPs identifies a susceptibility variant for Crohn disease in ATG16L1. *Nat Genet* 39, 207-211 (2007).
23. Rioux, J. D. et al. Genome-wide association study identifies new susceptibility loci for Crohn disease and implicates autophagy in disease pathogenesis. *Nat Genet* 39, 596-604 (2007).
24. Wellcome Trust Case Control Consortium. Genome-wide association study of 14,000 cases of seven common diseases and 3,000 shared controls. *Nature* 447, 661-78 (2007).
25. Libioulle, C. et al. Novel Crohn disease locus identified by genome-wide association maps to a gene desert on 5p13.1 and modulates expression of PTGER4. *PLoS Genet* 3, e58 (2007).
26. Singh, S. B., Davis, A. S., Taylor, G. A. & Deretic, V. Human IRGM induces autophagy to eliminate intracellular mycobacteria. *Science* 313, 1438-41 (2006).
27. Parkes, M. et al. Sequence variants in the autophagy gene IRGM and multiple other replicating loci contribute to Crohn's disease susceptibility. *Nat Genet* 39, 830-2 (2007).
28. Baldassano, R. N. et al. Association of the T300A non-synonymous variant of the ATG16L1 gene with susceptibility to paediatric Crohn's disease. *Gut* 56, 1171-3 (2007).
29. Gunderson, K. L., Steemers, F. J., Lee, G., Mendoza, L. G. & Chee, M. S. A genome-wide scalable SNP genotyping assay using microarray technology. *Nat Genet* 37, 549-54 (2005).
30. Ina, K. et al. Resistance of Crohn's disease T cells to multiple apoptotic signals is associated with a Bcl-2/Bax mucosal imbalance. *J Immunol* 163, 1081-90 (1999).
31. Prescott, N. J. et al. A nonsynonymous SNP in ATG16L1 predisposes to ileal Crohn's disease and is independent of CARD15 and IBD5. *Gastroenterology* 132, 1665-71 (2007).
32. Satsangi, J. et al. Contribution of genes of the major histocompatibility complex to susceptibility and disease phenotype in inflammatory bowel disease. *Lancet* 347, 1212-7 (1996).
33. Bousvaros, A. et al. Differentiating ulcerative colitis from Crohn disease in children and young adults: report of a working group of the North American Society for Pediatric Gastroenterology, Hepatology, and Nutrition and the Crohn's and Colitis Foundation of America. *J Pediatr Gastroenterol Nutr* 44, 653-74 (2007).
34. Silverberg, M. S. et al. Toward an integrated clinical, molecular and serological classification of inflammatory bowel disease: Report of a Working Party of the 2005 Montreal World Congress of Gastroenterology. *Can J Gastroenterol* 19 Suppl A, 5-36 (2005).
35. Steemers, F. J. et al. Whole-genome genotyping with the single-base extension assay. *Nat Methods* 3, 31-3 (2006).
36. Hakonarson, H. et al. A genome-wide association study identifies KIAA0350 as a type 1 diabetes gene. *Nature* 448, 591-594 (2007).
37. Satsangi, J., Silverberg, M. S., Vermeire, S. & Colombel, J. F. The Montreal classification of inflammatory bowel disease: controversies, consensus, and implications. *Gut* 55, 749-53 (2006).

Example III

In the present example, we report results from a GWA study conducted on a large cohort of pediatric onset IBD subjects ascertained through international collaboration, which has lead to the identification of several additional novel IBD loci and to the replication of previously reported loci, thereby allowing us to develop a genetic risk model for pediatric-onset IBD aimed at future prediction of disease susceptibility.

The following materials and methods are provided to facilitate the practice of the present example.

Participants

The pediatric IBD discovery case cohort (Table 9) consisted of 2413 Caucasian patients (1637 with CD, 723 with UC and 53 with IBD-U) recruited from multiple centers from 4 geographically discrete countries (Table 10) that met the study's quality control criteria and were successfully matched with disease-free control subjects from the United States (see details below). All patients were diagnosed prior to their 19th birthday and fulfilled standard IBD diagnostic criteria. Family history of IBD was obtained with focus on first degree relatives. A patient was considered to be of Jewish heritage when at least 2 grandparents were known to be Jewish. Phenotypic characterization was based on a modification of the Montreal classification such that the definitions of L1 & L3 were both extended to include disease within the small bowel proximal to the terminal ileum and distal to the ligament of Treitz. Disease above the ligament of Treitz was recorded separately; perianal disease included only those patients with perianal abscess and/or fistula. "Isolated Colonic IBD" included all patients with disease limited to the colon (723 with UC, 53 with IBD-U, and 402 with Colonic CD). The term 'very early onset disease' was applied to cases where the diagnosis was made at or prior to 8 years of age (Table 11). The Research Ethics Board of the respective Hospitals and other participating centers approved the study, and written informed consent was obtained from all subjects. A sub-group of IBD patients employed in this study (1101 patients, including 647 CD and 317 UC and 47 inflammatory bowel disease type unclassified (IBDU)), were utilized in a previous IBD GWA analysis reporting on two novel IBD loci on chromosome 20q13 and 21q22(11); however, only novel and non-overlapping loci are being described in this manuscript (Table 12).

The control group was recruited by CHOP clinicians, nursing and medical assistant staff within the CHOP Health Care Network, which includes primary care clinics and outpatient practices. The control subjects did not have IBD or evidence of chronic disease based on self-reported intake questionnaire or clinician-based assessment. The Research Ethics Board of CHOP approved the study, and written informed consent was obtained from all subjects.

Genotyping

We performed high throughput genome-wide SNP genotyping, using the Illumina Infinium™ II HumanHap550 BeadChip technology (Illumina, San Diego), at the Center for Applied Genomics at CHOP, as previously described in Examples I and II. Following genotyping, we excluded 251 IBD samples with greater than 2% missing genotypes. We used the program STRUCTURE to exclude a further 316 patients with less than 95% European ancestry based on ancestry informative markers (14).

TABLE 9

Study recruitment, subsequent inclusion, and ultimate demographic and phenotypic characteristics of caucasian subjects with matched controls who were included in the association study (n = 2413)

|  | IBD [n] | CD [n] | UC [n] | IBD-U [n] | Isolated Colonic IBD [n] |
|---|---|---|---|---|---|
| Recruited for Study | | | | | |
| Total number of Subjects | 3370 | 2304 | 993 | 73 | n/a |
| Subjects meeting Quality Control Criteria (inc Caucasian Ethnicity) | | | | | |
| Total number of Subjects | 2784 | 1887 | 835 | 62 | n/a |
| Subjects Ultimately Matched and included in Association Analysis | | | | | |
| Total number of Subjects | 2413 | 1637 | 723 | 53 | 1178 |
| Male | 1273 (52.7%) | 927 (56.6%) | 321 (44.3%) | 25 (47.2%) | 567 (48.1%) |
| Median Age at Diagnosis (IQR) | 12 yrs (9-14.2) | 12 yrs (10-14) | 12 yrs (8-15) | 10.25 yrs (7-13.5) | 12 yrs (8-14) |

TABLE 9-continued

Study recruitment, subsequent inclusion, and ultimate demographic and phenotypic characteristics of caucasian subjects with matched controls who were included in the association study (n = 2413)

| Patient Subgroups | | | | | |
|---|---|---|---|---|---|
| Age at Dx </= 8 yrs | 489 | 265 | 205 | 19 | 321 |
| 1° Familial Hx (Valid %)[1] | 289 (14%) | 215 (15.5%) | 63 (10.2%) | 11 (21%) | 130 (12.4%) |
| Known Jewish Heritage (Valid %)[2] | 223 (9.6%) | 161 (10.3%) | 57 (8.1%) | 5 (9.8%) | 98 (8.5%) |

| CD Anatomic Location[3] | | UC Disease Extent[4] | |
|---|---|---|---|
| Isolated Small Bowel Disease (Valid %) | 297 (20%) | Extensive Disease (Valid %) | 394 (70%) |
| Isolated Colonic Disease (Valid %) | 402 (27.2%) | Left-Sided Disease (Valid %) | 168 (30%) |
| Small Bowel Colon Disease (Valid %) | 769 (52%) | | |
| Any Perianal Disease[5] (Valid %) | 312 (21.4%) | | |

| CD Disease Behaviour[6] | | | |
|---|---|---|---|
| Fibrostenotic | 187 (15.7%) | Internally Penetrating | 190 (15.9%) |

[1]Family Hx details not available in 14% of cases

[2]Jewish Heritage unknown in 4% of cases

[3]7 cases had disease isolated to the upper tract, one case had disease isolated to the perianal region. Complete disease location data unavailable in 10% of CD cases

[4]Details of disease extent unavailable in 22% of UC cases

[5]Details of perianal disease unavailable in 11% of CD cases

[6]Details of disease behaviour at latest review unavailable in 27% of CD cases

TABLE 10

Geographic Distribution of Caucasian Subjects with Matched Controls who were included in the Association Study (n = 2413)

| | Able to be Matched to Controls |
|---|---|
| Italy | 322 |
| Scotland | 374 |
| Canada | 528 |
| United States | 1189 |
| TOTAL | 2413 |

TABLE 11

Demographic and Phenotypic Characteristics of the sub-group of matched Caucasian Subjects included in the Association Study who were diagnosed with IBD at or before 8 years of age (n = 489)

|  | IBD | CD | UC | IBD-U | Isolated Colonic IBD |
|---|---|---|---|---|---|
| Total number of Subjects | 489 | 265 | 205 | 19 | 321 |
| Male | 266 (54.5%) | 155 (58.7%) | 100 (48.8%) | 11 (57.9%) | 160 (49.8%) |
| Median Age at Diagnosis | 6 yrs | 6.5 yrs | 6 yrs | 6 yrs | 6 yrs |
| (IQR) | (4 to 8) | (4 to 7.5) | (4 to 7.5) | (3 to 7.5) | (4 to 7.4) |
| 1° Familial Hx (Valid %)[1] | 62 (14.9%) | 44 (19.4%) | 13 (7.6%) | 5 (26%) | 36 (13%) |
| Known Jewish Heritage[2] | 59 (12.6%) | 32 (12.8%) | 23 (11.5%) | 4 (21%) | 37 (11.7%) |

| CD Anatomic Location[3] | | UC Disease Extent[4] | |
|---|---|---|---|
| Isolated Small Bowel Disease (Valid %) | 18 (7.5%) | Extensive Disease (Valid %) | 113 (70%) |
| Isolated Colonic Disease (Valid %) | 97 (40.4%) | Left-Sided Disease (Valid %) | 47 (30%) |
| Small Bowel Colon Disease (Valid %) | 124 (51.7%) | | |
| Any Perianal Disease[5] (Valid %) | 56 (23.5%) | | |

| CD Disease Behaviour[6] | | | |
|---|---|---|---|
| Fibrostenotic | 27 (13.5%) | Internally Penetrating | 25 (12.5%) |

TABLE 12

Discovery cohort sizes and filtering

| | Kuthagasan et al(11) | | | Consortium | | | All | | | |
|---|---|---|---|---|---|---|---|---|---|---|
| | CD | UC | IBD | CD | UC | IBD | CD | UC | IBD | Controls |
| QC Filtered | 647 | 317 | 1011 | 1241 | 548 | 1677 | 1888 | 865 | 2688 | 7315 |
| Eigenmatched | 606 | 308 | 903 | 966 | 470 | 1510 | 1689 | 778 | 2413 | 6197 |

Genetic Matching

We performed eigen-matching to minimize population stratification arising from differing geographic origins between our Caucasian cases and controls. Eigen-matching uses singular value decomposition of genotypic data to match cases to their closest controls in the space of k principal components. This approach is a variant of a method recently published by Luca et al (15), however in contrast to the outlined method, we employ matching as a criterion to filter patients for subsequent case control analyses. Unlike EIGENSTRAT, a common approach to correct for the effects of stratification by adjusting genotype values, eigen-matching removes samples from both cases and controls that are responsible for stratification.

Our final discovery cohort following matching consisted of 2413 patients and 6197 controls, which included 1689 CD cases and 778 UC cases (each of which included 53 IBD-U cases). Contained in this cohort were 205 very early-onset UC and 251(16) very early-onset CD cases (each including 15 IBD-U cases). A summary of the number of recruited patients who met quality control and genetic matching criteria for study inclusion is shown Table 9.

Association Analysis

All tests of association were carried out using PLINK (17) with standard criteria for SNP quality control filtering yielding 500,606 SNPs. Given a conservative estimate of 500,606 independent hypotheses, we determined genome-wide significance with a Bonferroni-corrected P-value threshold of $1.0 \times 10^{-7}$. We also examined nominal signals below a P-value threshold of $1 \times 10^{-6}$. We excluded 73, 45, and 4 SNPs at or below the suggestive P-value threshold due to genotyping error in the IBD, CD, and UC analyses, respectively. We applied the same quality-control criterion to filter results obtained for very-early onset, familial, colon-only, and CD/UC without IBD-U analyses. All resulting loci with P<0.0001 for CD, UC, IBD and their sub-analyses are included as Supplementary Data.

Replication Experiments

We leveraged results from the previously reported CD meta-analysis (1), which combined data from three scans, totaling 3,230 cases and 4,829 controls, in order to attempt to replicate our observed signals from the association analyses. Since the replication cohort we had access to did not include a separate cohort of patients with UC, we have focused the replication analysis on the CD and IBD-combined signals. However, an independent cohort of 60 UC trios, recruited at the Boston Children's Hospital, was available for replication analysis of the UC signal observed in subjects with disease onset less than 8 years of age. Details regarding replication cohort genotyping are included in the supplementary methods.

Gene Expression Analysis

We examined allele specific effects on gene expression for significantly associating loci by assaying total RNA in genotyped lymphoblast cell lines. We also compared gene expression levels between colonic biopsy specimens obtained from pediatric IBD cases and normal controls to detect disease specific gene expression differences.

To evaluate allele specific effects on gene expression at the IL27 locus for the rs1968752 variant (A/A genotype: NA10835, NA10854, NA10860, NA12006, NA12056 and the C/C genotype: NA12144, NA12155, NA12760, NA06993, NA07029) RNA was isolated from HapMap-Ceu population samples using Trizol (Invitrogen). Real-time RT PCR was performed on a Bio-Rad iCycler System using SYBR Green detection (Bio-Rad). cDNA template was made from 2 µg of total RNA using the Invitrogen cDNA Synthesis kit. Primer sequences were designed using Integrated DNA Technologies (IDT). Beta-actin was used as the control gene. Primer sequences and GenBank accession numbers for the genes selected for PCR validation are as follows. IL27 (NM_145659, 149 bp)) Forward: 5-TGATGTTTCCCTGACCTTCCAGG-3 (SEQ ID NO: 1); Reverse: 5-ACAGCTGCATCCTCTCCATGTT-3 (SEQ ID NO: 2); Beta-actin (NM_001101, 138 bp). Forward: 5-TCAGAAGGATTCCT ATGTGGGCGA-3 (SEQ ID NO: 3); Reverse: 5-CACACGCAGCTCATTGTAGAAGGT-3 (SEQ ID NO: 4). Each reaction was carried out in triplicate wells on one plate. Fold change between A/A and C/C genotype was calculated with the comparative CT method. Results were normalized to beta-actin for cDNA quantification differences. Data were analyzed using ANOVA. We additionally examined allele-specific effects on expression of the TLR locus (TLR-1, TLR6, and TLRJO) in these same cell lines and in colonic biopsy specimens from pediatric patients with CD and UC in comparison with healthy controls. For the latter experiments, biotinylated cRNA was hybridized to the Affymetrix GeneChip HG-U133 Plus 2.0 arrays, containing probes for approximately 22,634 genes at the CCHMC Digestive Health Center Microarray Core. The images were captured using Affymetrix GeneChip Scanner 3000. Data were normalized to allow for array to array comparisons, and differences between groups were detected in GeneSpring™ with significance at the 0.05 level relative to healthy control samples using analysis of variance and Newman-Keuls multiple comparison test.

Risk Modeling

Cumulative risk models were constructed for CD, UC, and IBD in a similar fashion to those recently reported in non-insulin dependent diabetes (16, 18, 19). Each model was built using previously described loci that were significant in our analysis as well as for novel loci identified by our study. This corresponded to 30 loci in CD, 17 loci in UC, and 37 loci in IBD. For each locus, the risk allele was designated as the allele that yielded an OR>1. At each locus, each individual could thus have 0, 1 or 2 risk alleles. A genotype score representing risk allele burden for UC, CD, and IBD was computed for each individual in the study as the total number of risk alleles across all loci in the respective model.

Given a distribution of genotype scores in our case and control populations, we computed odds ratios for disease with respect to a reference group for each model. In this regard, we set a threshold score to yield a reference group comprising the lowest 7-10 percentile in the study population. This corresponded to thresholds of 23, 13, and 28 risk alleles for the CD, UC, and IBD models, respectively. Similarly, we defined a "high score" group as comprising the upper 7-10 percentile of the risk allele burden distribution for each diagnosis. This corresponded to thresholds of 34, 20, and 40 risk alleles for the CD, UC, and IBD models, respectively. For each model, we assigned the remaining patients into risk groups defined by each unique value of the genotype scale between the "low score" and "high score" group thresholds. For a given risk group (corresponding to a genotypic score), the odds ratio and its confidence interval was computed as a function of the number of cases/controls in that group and the number of cases/controls in the reference group. We also used logistic regression to quantify the degree of additional risk conferred by each genotypic score increment. We set up the regression employing the odds ratio as the dependent and the genotypic score as the independent variable. The slope of the resulting linear fit corresponds to an estimate of marginal risk conferred by each risk allele burden increment.

Results

Figure 4:
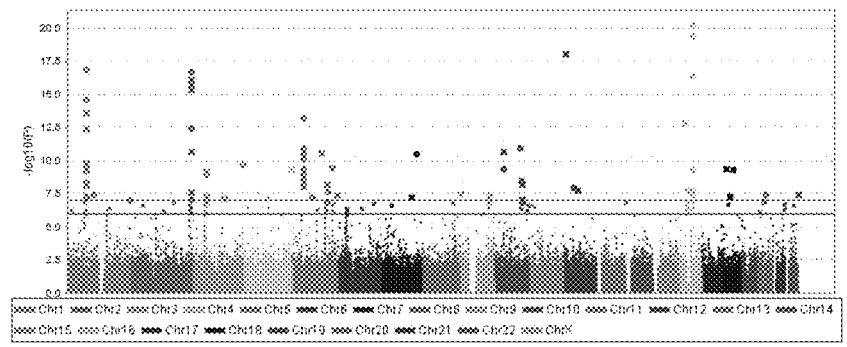
FIG. 4. Scatter plots of −log(P) against genomic location for our three main genome scans. Figures were generated using Haploview (49).
Figure 4:
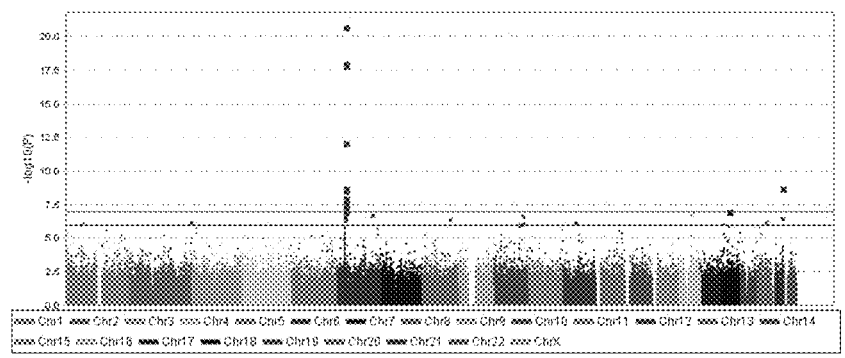
Figure 4:
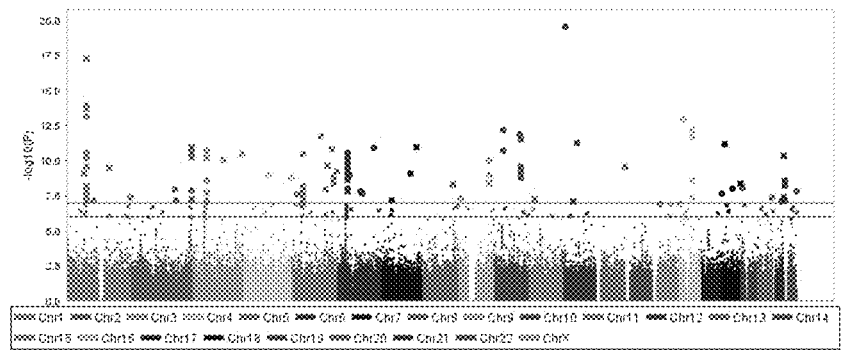

To detect significantly associated susceptibility alleles, we compared single-marker allele frequencies using $X^2$ statistics on SNPs with a minor allele frequency greater than 1% and with Hardy-Weinberg equilibrium $P<10^5$. Plots of association results are shown in FIG. 4.

Crohn's Disease

Our CD analysis yielded one novel locus at the genome-wide significant threshold ($P<1.0\times10^{-7}$) and three novel loci at the suggestive significant level ($P<1\times10^{-6}$; Table 13). Of these three signals, two were further corroborated by in silico analysis of the independent CD-meta analysis data set ($P<0.05$ after correcting for three independent tests). These replicating CD loci reside on 16p11 and 5q15, respectively (Table 13).

TABLE 13

Novel genome wide significant ($P < 1 \times 10^{-7}$) and suggestive ($P < 1 \times 10^{-6}$) putative CD loci identified in this GWA scan. Loci highlighted in bold italics were independently replicated in a large adult CD cohort. Z scores in the meta analysis cohort represent directions of effect of the minor allele, with positive (negative) Z-scores conferring risk (protection). Criteria for determining bounds of region of association are described in the Methods.

| | | | | CD Discovery (1689) | | | | CD meta analysis | | |
|---|---|---|---|---|---|---|---|---|---|---|
| Band | MB | Genes | SNP | P | Aff | Unaff | OR | SNP | P | Z |
| 16p11.2 | 28.45-28.54 | IL27 | rs1968752 | 1.27E-08 | 0.39 | 0.34 | 1.26 [1.16-1.36] | rs478804 | 3.50E-03 | 2.92 |
| 6p21.33 | 31.60-31.67 | BAT1, LST1, LTA, LTB, NCR3, NFKBIL1, TNF | rs2844480 | 3.71E-07 | 0.24 | 0.20 | 1.27 [1.16-1.39] | rs2844482 | 1.02E-01 | -1.63 |
| 5q15 | 96.23-96.40 | LNPEP, LRAP | rs10044354 | 4.4Ee-07 | 0.45 | 0.41 | 1.22 [1.13-1.31] | rs27302 | 2.78E-03 | 2.99 |

Figure 5A:
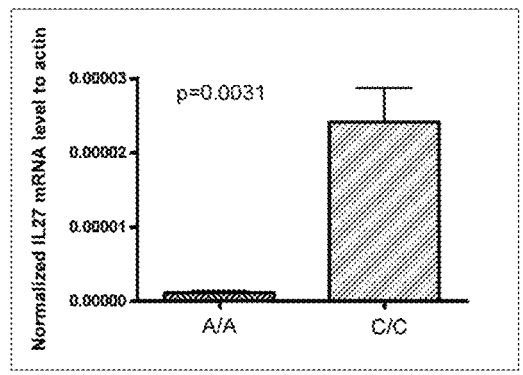
FIG. 5. Allelic effects of SNPs on lymphoblastoid cell line gene expression of IL27. The A allele of rs1968752 confers risk in our CD cohort (OR=1.23 [1.12-1.40]). rs1968752 lies in an LD-block containing the IL27 gene. Individuals with the A/A genotype at rs1968752 have 15 fold decrease in IL27 gene expression compared to those with the C/C genotype. Reduced IL27 expression is likely to promote inflammation through activation of the Th-17 lineage.
Figure 5B:
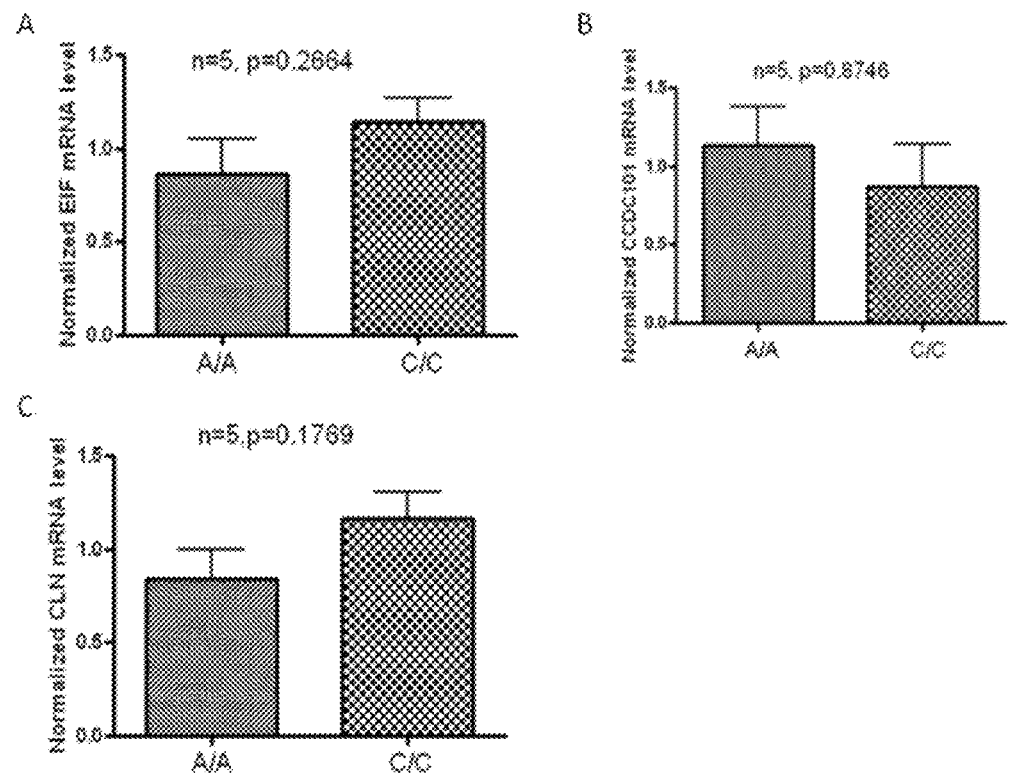
Figure 6:
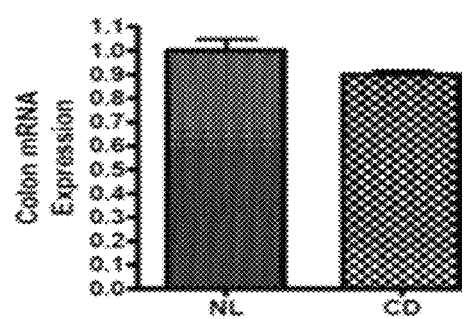
FIG. 6. Colonic expression of IL27 in CD cases vs controls. We compared colonic gene expression between 13 normal (NL) and 37 CD samples, using a students T-test with significance threshold of P<0.05. We found that IL-27 expression is significantly reduced in the CD cases in comparison with normal tissue, (P=0.028).

The most significant SNP in the LD block harboring the 16p11 signal, rs1968752, yielded a $P=1.27\times10^{-8}$, with its minor A allele conferring risk (OR=1.26 [1.16-1.36]). In the CD meta-analysis dataset, an LD proxy for this SNP, rs4788084 (r2=0.83), was found to associate with CD (P=0.0035 OR=1.13). This LD block contains multiple genes, including IL27, CCDC101, CLN3, EIF3C, NUPR1 and SULT1A1, of which the most plausible candidate for CD pathogenesis is IL27, an immunomodulatory cytokine that is posited to regulate adaptive immunity responses. To determine if IL27 expression varied according to genotype, we compared IL27, CCDC101, CLN3, and EIF3C expression levels in lymphoblastoid cell lines obtained from 10 homozygous individuals with either the AA or GG rs1968752 genotype. We detected a several fold decrease in IL27 gene expression in individuals with the AA genotype relative to those with GG (FIG. 5A), suggesting that this SNP may exerts a potent regulatory effect on IL27 gene expression (P=0.0031). Unlike IL27, expression effects were not observed for the other genes at this locus (FIG. 5B). Measuring IL27 colonic gene expression in 37 CD and 13 control samples, we detected significantly reduced expression in CD when compared to normal tissue (P=0.028) (FIG. 6).

With respect to the 5q15 association signal, it resides in an LD block harboring two genes: LNPEP and LRAP. The primary SNP in this region, rs10044354, associated with CD at a P-value of $4.5 \times 10^{-7}$ and OR=1.22 [1.13-1.31]. Since this SNP is not contained in the meta-analysis dataset, we corroborated this result with an LD proxy SNP (rs27302; r2=0.932), which associates with CD in the discovery dataset with P=$3.843 \times 10^{-6}$ and OR=1.19 and replicates in the meta-analysis (P=0.0028, OR=1.09). We did not observe allele specific changes in LNPEP/LRAP gene expression in lymphoblastoid cell lines based on the genotype of these SNPs. We also did not observe a difference in LNPEP/LRAP gene expression between normal and Crohn's Disease colonic biopsies (data not shown).

In addition to the discovery of IL27 and LNPEP/LRAP as novel CD loci, we also sought evidence of association with previously reported adult-onset CD signals (Table 14). Of the 32 CD loci implicated by meta-analysis, 28 showed nominal evidence of replication, 21 were significant to a Bonferroni adjusted P value of 0.05 (adjusting for 32 hypotheses). Eleven of these previously reported loci, including IL23R, NOD2, IL12B, and ATG16L1, were genome-wide significant (P<$1.0 \times 10^{-7}$) in our pediatric IBD cohort. Of the eight CD loci shown to be nominally significant in the previously reported CD meta-analysis, we observed association for three (P value<0.00625)(1). These were the IL18R1-IL18RAP locus on 2q12 (rs917997 P=$2.23 \times 10^{-6}$, OR=1.23 [1.13-1.34]), the C-C motif chemokine (CCL) gene cluster on 17q12 (rs991804, P=$1.05 \times 10^{-4}$, OR=0.84 [0.77-0.92]) and the CCDC139 locus on 2p16 (rs13003464, P=$2.81 \times 10^{-3}$, OR=1.12 [1.04-1.22]). In addition, when examining previously reported UC signals in our CD cohort, we detected association to the recently identified UC gene, IL10 on 1q32.1, suggesting that this locus may also play a role in CD susceptibility (rs3024505, P=$1.0 \times 10^{-4}$, OR=1.22 [1.11-1.36]) (Table 15).

TABLE 14

48 previously identified IBD loci examined by our study, including 8 loci having nominal evidence for association with IBD/CD/UC in previous studies and 2 loci published on a subset of the current cohort (asterisk). Filled circles in the first four columns of the table specify whether the given row represents a (1) known CD locus, (2) putative/nominal CD locus, (3) known UC locus, and/or (4) putative/nominal UC locus, respectively. We replicate 21 of 32 known CD loci, 8 of 15 known UC loci, and overall 26 of 38 known IBD loci. Loci replicating at a Bonferronni-corrected P < .05 are denoted in bold. Our data also implicate several previously described CD loci as having association with UC (bold italics). We also verify 3 nominally associating SNPs from the recent CD meta-analysis (bold italics).

| | | | | | | | | | CD | | | |
|---|---|---|---|---|---|---|---|---|---|---|---|---|
| | | | | | | | | | All (1689) | | Small Bowel (297) | Colonic (402) | Small Bowel + Colon (769) |
| (1) | (2) | (3) | (4) | band | MB | Genes | SNP | P | OR | OR | OR | OR |
| • | | | | 1p13.2 | 114.18 | PTPN22 | rs2476601 | 5.61E−06 | 0.71 [0.62-0.83] | 0.66 [0.47-0.92] | 0.80 [0.62-1.05] | 0.72 [0.58-0.88] |
| • | | | | 1p31.3 | 67.48 | IL23R | rs11465804 | 2.10E−14 | 0.45 [0.36-0.55] | 0.43 [0.26-0.70] | 0.47 [0.31-0.70] | 0.47 [0.35-0.63] |
| | | • | | 1q21.2 | 148.75 | | rs13294 | 7.20E−01 | 1.01 [0.94-1.10] | 0.89 [0.76-1.06] | 1.06 [0.92-1.23] | 1.07 [0.96-1.19] |
| • | | | | 1q23.3 | 159.12 | OR10J1 | rs2274910 | 3.87E−01 | 0.96 [0.89-1.05] | 1.09 [0.92-1.30] | 0.94 [0.80-1.10] | 0.95 [0.84-1.06] |
| • | | | | 1q24.3 | 171.13 | FMO4 | rs9286879 | 3.81E−05 | 1.20 [1.10-1.30] | 1.19 [0.99-1.43] | 1.20 [1.03-1.41] | 1.23 [1.10-1.39] |
| • | | | | 1q32.1 | 199.25 | | rs12122721 | 1.48E−01 | 0.94 [0.86-1.02] | 0.78 [0.64-0.95] | 1.02 [0.87-1.20] | 0.95 [0.84-1.07] |
| | • | | | 1q32.1 | 205.01 | RBBP5, RIPK5 | rs3024505 | *1.01E−04* | *1.22* [*1.11-1.36*] | 1.05 [0.83-1.32] | 1.36 [1.13-1.64] | 1.22 [1.06-1.40] |
| | • | | | 2p16.1 | 61.04 | AHSA2, CCDC139, PEX13, USP34, PUS10 | rs13003464 | *2.81E−03* | *1.12* [*1.04-1.22*] | 1.26 [1.06-1.48] | 1.08 [0.93-1.25] | 1.12 [1.01-1.25] |
| • | | | | 2p23.3 | 27.59 | GCKR | rs780094 | 2.56E−01 | 1.05 [0.97-1.13] | 1.22 [1.03-1.43] | 0.99 [0.86-1.15] | 1.06 [0.95-1.18] |
| • | | | | 2q12.1 | 102.44 | IL18R1, IL18RAP, | rs917997 | *2.23E−06* | *1.23* [*1.13-1.34*] | 1.23 [1.02-1.48] | 1.27 [1.08-1.49] | 1.19 [1.05-1.34] |
| | • | | | 2q35 | 218.77 | Multiple | rs6752254 | 7.43E−01 | 0.99 [0.91-1.07] | 1.04 [0.88-1.22] | 0.97 [0.84-1.12] | 0.95 [0.86-1.06] |
| • | | | | 2q37.1 | 233.85 | DGKD | rs2241880 | 1.57E−17 | 0.71 [0.66-0.77] | 0.59 [0.50-0.71] | 0.89 [0.77-1.03] | 0.69 [0.62-0.77] |
| | • | | | 3p12.1 | 85.84 | CADM2 | rs7611991 | 6.87E−01 | 0.98 [0.90-1.07] | 0.99 [0.82-1.20] | 0.98 [0.84-1.16] | 0.99 [0.87-1.11] |
| • | | | | 3p21.31 | 49.70 | MST1 | rs3197999 | 3.48E−08 | 1.26 [1.16-1.36] | 1.40 [1.17-1.67] | 1.28 [1.10-1.49] | 1.18 [1.05-1.32] |
| | • | • | | 5p13.1 | 40.43 | PTGER4 | rs4613763 | 1.68E−05 | 1.28 [1.14-1.43] | 1.42 [1.13-1.78] | 0.96 [0.77-1.21] | 1.34 [1.16-1.56] |
| | | • | | 5q13.3 | 76.18 | F2RL1, S100Z | rs7724915 | 3.74E−01 | 0.94 [0.81-1.08] | 0.98 [0.72-1.35] | 0.75 [0.55-1.01] | 1.04 [0.85-1.27] |

TABLE 14-continued 48 previously identified IBD loci examined by our study, including 8 loci having nominal evidence for association with IBD/CD/UC in previous studies and 2 loci published on a subset of the current cohort (asterisk). Filled circles in the first four columns of the table specify whether the given row represents a (1) known CD locus, (2) putative/nominal CD locus, (3) known UC locus, and/or (4) putative/nominal UC locus, respectively. We replicate 21 of 32 known CD loci, 8 of 15 known UC loci, and overall 26 of 38 known IBD loci. Loci replicating at a Bonferronni-corrected P < .05 are denoted in bold. Our data also implicate several previously described CD loci as having association with UC (bold italics). We also verify 3 nominally associating SNPs from the recent CD meta-analysis (bold italics).

| (1) | (2) | (3) | (4) | band | | | SNP | P | OR | | | |
|---|---|---|---|---|---|---|---|---|---|---|---|---|
| • | | | | 5q31.1 | 131.80 | Multiple | rs2188962 | 2.72E-06 | 1.20 [1.11-1.30] | 1.20 [1.01-1.41] | 1.16 [1.01-1.34] | 1.32 [1.19-1.47] |
| • | | | | 5q33.1 | 150.25 | ZNF300 | rs7714584 | 1.46E-03 | 1.22 [1.08-1.38] | 1.45 [1.14-1.85] | 1.09 [0.86-1.38] | 1.26 [1.06-1.48] |
| • | • | | | 5q33.3 | 158.75 | IL12B, RNF145, UBLCP1 | rs10045431 | 6.55E-07 | 0.80 [0.73-0.87] | 0.70 [0.58-0.86] | 0.87 [0.74-1.02] | 0.80 [0.71-0.90] |
| • | • | | | 6p21.32 | 32.54 | BTNL2, SLC26A3, HLA-DRB1, HLA-DQA1 | rs2395185 | 5.07E-02 | 0.92 [0.85-1.00] | 1.08 [0.91-1.29] | 0.85 [0.73-0.99] | 0.95 [0.84-1.06] |
| | • | | | 6p21.32 | 32.69 | HLA-DRA | rs660895 | 2.38E-04 | 0.83 [0.75-0.92] | 0.91 [0.74-1.13] | 0.78 [0.65-0.95] | 0.84 [0.73-0.97] |
| • | | | | 6p22.3 | 20.84 | CDKAL1 | rs6908425 | 2.40E-02 | 0.90 [0.81-0.99] | 0.84 [0.68-1.04] | 0.94 [0.79-1.13] | 0.87 [0.76-1.00] |
| | • | | | 6p25.1 | 5.10 | LYRMA | rs12529198 | 7.73E-01 | 0.98 [0.84-1.13] | 1.11 [0.82-1.51] | 0.99 [0.75-1.30] | 0.85 [0.68-1.06] |
| | • | | | 6p25.2 | 3.38 | C6orf85 | rs4959832 | 8.60E-01 | 0.99 [0.92-1.07] | 1.04 [0.88-1.24] | 1.03 [0.89-1.19] | 0.92 [0.83-1.03] |
| • | | | | 6q21 | 106.58 | | rs6938089 | 2.56E-02 | 1.10 [1.01-1.19] | 1.14 [0.96-1.36] | 1.17 [1.01-1.36] | 1.05 [0.94-1.18] |
| | • | | | 6q25.1 | 149.62 | | rs7758080 | 9.21E-01 | 1.00 [0.92-1.09] | 0.94 [0.78-1.13] | 0.98 [0.83-1.14] | 1.03 [0.92-1.16] |
| • | | | | 6q27 | 167.36 | CCR6, FGFR1OP, GPR31 RNASET2, | rs2301436 | 3.36E-02 | 1.09 [1.01-1.17] | 1.07 [0.91-1.27] | 1.18 [1.02-1.36] | 1.04 [0.94-1.16] |
| • | | | | 7p12.2 | 50.24 | ZPBP | rs1456893 | 5.10E-05 | 0.84 [0.77-0.91] | 0.86 [0.71-1.03] | 0.76 [0.64-0.89] | 0.85 [0.75-0.95] |
| • | | | | 8q24.13 | 126.61 | | rs1551398 | 1.26E-06 | 0.82 [0.76-0.89] | 0.83 [0.70-0.99] | 0.89 [0.76-1.03] | 0.76 [0.68-0.85] |
| • | • | | | 9p24.1 | 4.97 | INSL6, JAK2 | rs10758669 | 2.71E-04 | 1.16 [1.07-1.25] | 1.29 [1.09-1.52] | 1.26 [1.09-1.46] | 1.11 [1.00-1.24] |
| • | | | | 9q32 | 116.60 | SLC46A2 | rs6478108 | 8.43E-08 | 0.79 [0.73-0.86] | 0.88 [0.74-1.05] | 0.80 [0.68-0.94] | 0.74 [0.66-0.84] |
| | • | | | 10q21.2 | 64.07 | ZNF365 | rs10995250 | 1.16E-06 | 1.21 [1.12-1.31] | 1.02 [0.86-1.21] | 1.12 [0.97-1.29] | 1.34 [1.20-1.49] |
| • | • | | | 10q24.2 | 101.28 | NKX2-3 | rs11190140 | 4.43E-09 | 1.26 [1.16-1.36] | 1.31 [1.11-1.55] | 1.15 [1.00-1.33] | 1.28 [1.15-1.42] |
| • | | | | 11q13.5 | 75.95 | C11orf30 | rs7130588 | 4.90E-03 | 1.12 [1.03-1.21] | 1.16 [0.98-1.37] | 1.08 [0.93-1.25] | 1.15 [1.03-1.28] |
| • | | | | 12q12 | 38.67 | LRRK2, SLC2A13 | rs11174631 | 7.24E-05 | 1.43 [1.20-1.70] | 1.51 [1.05-2 17] | 1.20 [0.85-1.69] | 1.53 [1.21-1.93] |
| • | | | | 13q14.11 | 43.36 | C13orf31, CCDC122, ENOX1 | rs3764147 | 1.10E-04 | 1.18 [1.09-1.29] | 1.29 [1.08-1.54] | 1.07 [0.91-1.26] | 1.18 [1.05-1.33] |
| | • | | | 15q13.1 | 26.20 | HERC2, OCA2 | rs1667394 | 4.66E-01 | 0.97 [0.88-1.06] | 1.08 [0.88-1.32] | 0.95 [0.80-1.14] | 0.94 [0.82-1.07] |
| | • | | | 17q12 | 29.61 | CCL11, CCL2, CCL7 | rs991804 | 1.05E-04 | 0.84 [0.77-0.92] | 0.75 [0.61-0.91] | 0.94 [0.80-1.11] | 0.83 [0.73-0.94] |
| • | | | | 17q12 | 35.29 | ORMDL3 | rs2872507 | 2.32E-03 | 1.13 [1.04-1.21] | 1.08 [0.92-1.28] | 1.16 [1.01-1.34] | 1.12 [1.01-1.25] |
| • | • | | | 17q21.2 | 37.77 | STAT3 | rs744166 | 4.32E-02 | 0.92 [0.85-1.00] | 0.96 [0.81-1.13] | 0.91 [0.79-1.06] | 0.88 [0.79-0.96] |
| | • | | | 18p11.21 | 12.80 | PTPN2 | rs1893217 | 4.86E-04 | 1.20 [1.08-1.32] | 1.45 [1.18-1.78] | 1.09 [0.90-1.32] | 1.20 [1.04-1.38] |

| | | | | | | UC | | IBD | | |
|---|---|---|---|---|---|---|---|---|---|---|
| | | | | | | All (777) | | All (2413) | | Colonic (1178) |
| (1) | (2) | (3) | (4) | band | | P | OR | P | OR | OR |
| | | | • | 1p13.2 | | 6.44E-01 | 0.96 [0.60-1.15] | 1.82E-04 | 0.79 [0.70-0.90] | 0.90 [0.77-1.06] |
| | | • | • | 1p31.3 | | *5.30E-04* | *0.64 [0.49-0.82]* | 7.33E-15 | 0.51 [0.43-0.61] | 0.58 [0.46-0.72] |
| | | | • | 1q21.2 | | 9.27E-02 | 1.10 [0.98-1.22] | 3.02E-01 | 1.04 [0.97-1.11] | 1.08 [0.99-1.19] |

TABLE 14-continued 48 previously identified IBD loci examined by our study, including 8 loci having nominal evidence for association with IBD/CD/UC in previous studies and 2 loci published on a subset of the current cohort (asterisk). Filled circles in the first four columns of the table specify whether the given row represents a (1) known CD locus, (2) putative/nominal CD locus, (3) known UC locus, and/or (4) putative/nominal UC locus, respectively. We replicate 21 of 32 known CD loci, 8 of 15 known UC loci, and overall 26 of 38 known IBD loci. Loci replicating at a Bonferronni-corrected P < .05 are denoted in bold. Our data also implicate several previously described CD loci as having association with UC (bold italics). We also verify 3 nominally associating SNPs from the recent CD meta-analysis (bold italics).

| (1) | (2) | (3) | (4) | Locus | P | OR [CI] | P | OR [CI] | OR [CI] |
|---|---|---|---|---|---|---|---|---|---|
| • |   |   |   | 1q23.3 | 4.89E−01 | 0.96 [0.86-1.08] | 3.22E−01 | 0.96 [0.90-1.04] | 0.95 [0.87-1.05] |
| • |   |   |   | 1q24.3 | 9.81E−01 | 1.00 [0.89-1.13] | 5.84E−04 | 1.14 [1.06-1.23] | 1.07 [0.97-1.18] |
| • |   |   |   | 1q32.1 | 3.45E−02 | 0.88 [0.78-0.99] | 3.59E−02 | 0.92 [0.86-0.99] | 0.93 [0.84-1.02] |
| • |   |   | • | 1q32.1 | 1.12E−03 | 1.26 [1.10-1.45] | 2.57E−06 | 1.24 [1.13-1.35] | 1.29 [1.15-1.45] |
| • |   |   |   | 2p16.1 | 1.47E−01 | 1.08 [0.97-1.21] | 1.50E−03 | 1.12 [1.04-1.19] | 1.08 [0.99-1.18] |
| • |   |   |   | 2p23.3 | 1.09E−02 | 1.15 [1.03-1.28] | 2.15E−02 | 1.08 [1.01-1.16] | 1.09 [1.00-1.19] |
| • |   |   |   | 2q12.1 | 1.56E−01 | 1.09 [0.97-1.23] | 7.09E−06 | 1.19 [1.10-1.29] | 1.15 [1.04-1.27] |
| • |   |   |   | 2q35 | 2.93E−02 | 0.89 [0.80-0.99] | 1.54E−01 | 0.95 [0.89-1.02] | 0.92 [0.84-1.00] |
| • |   |   |   | 2q37.1 | 4.97E−01 | 0.96 [0.87-1.07] | 7.37E−12 | 0.79 [0.74-0.84] | 0.94 [0.86-1.03] |
| • |   |   |   | 3p12.1 | 2.32E−03 | 0.82 [0.72-0.93] | 7.97E−02 | 0.93 [0.86-1.01] | 0.88 [0.79-0.97] |
| • | • |   |   | 3p21.31 | 9.43E−04 | 1.21 [1.08-1.35] | 1.77E−09 | 1.25 [1.16-1.34] | 1.23 [1.12-1.35] |
|   |   | • |   | 5p13.1 | 2.14E−02 | 1.20 [1.03-1.40] | 1.46E−05 | 1.24 [1.13-1.37] | 1.12 [0.98-1.28] |
| • |   |   |   | 5q13.3 | 7.21E−02 | 1.19 [0.98-1.43] | 8.28E−01 | 1.01 [0.89-1.15] | 1.03 [0.88-1.22] |
|   |   | • |   | 5q31.1 | 8.94E−01 | 0.99 [0.89-1.10] | 3.36E−04 | 1.13 [1.06-1.21] | 1.05 [0.96-1.15] |
| • |   |   |   | 5q33.1 | 1.08E−01 | 1.15 [0.97-1.36] | 8.02E−04 | 1.20 [1.08-1.34] | 1.13 [0.98-1.31] |
| • | • |   |   | 5q33.3 | 2.67E−05 | 0.77 [0.68-0.87] | 2.93E−09 | 0.79 [0.73-0.86] | 0.80 [0.72-0.89] |
| • | • |   |   | 6p21.32 | 1.59E−21 | 0.57 [0.50-0.64] | 6.59E−09 | 0.81 [0.75-0.87] | 0.66 [0.59-0.73] |
| • |   |   |   | 6p21.32 | 7.21E−13 | 0.57 [0.48-0.66] | 2.60E−11 | 0.74 [0.67-0.81] | 0.64 [0.56-0.72] |
| • |   |   |   | 6p22.3 | 9.62E−02 | 0.89 [0.78-1.02] | 6.73E−03 | 0.89 [0.82-0.97] | 0.91 [0.82-1.02] |
|   |   | • |   | 6p25.1 | 7.29E−01 | 0.96 [0.78-1.19] | 6.35E−01 | 0.97 [0.85-1.10] | 0.97 [0.82-1.15] |
| • |   |   |   | 6p25.2 | 7.25E−01 | 0.98 [0.88-1.09] | 6.45E−01 | 0.98 [0.92-1.05] | 1.00 [0.91-1.09] |
| • |   |   |   | 6q21 | 8.19E−01 | 1.01 [0.91-1.13] | 5.76E−02 | 1.07 [1.00-1.15] | 1.06 [0.97-1.17] |
|   |   | • |   | 6q25.1 | 4.47E−01 | 1.05 [0.93-1.17] | 6.72E−01 | 1.02 [0.94-1.09] | 1.02 [0.93-1.13] |
| • |   |   |   | 6q27 | 6.49E−01 | 1.02 [0.92-1.14] | 5.30E−02 | 1.07 [1.00-1.14] | 1.08 [0.99-1.17] |
| • |   |   |   | 7p12.2 | 7.94E−01 | 1.02 [0.91-1.14] | 7.50E−04 | 0.88 [0.82-0.95] | 0.92 [0.84-1.02] |
| • |   |   |   | 8q24.13 | 8.77E−01 | 1.01 [0.91-1.12] | 1.84E−05 | 0.88 [0.82-0.84] | 0.97 [0.88-1.06] |
| • | • |   |   | 9p24.1 | 1.70E−02 | 1.14 [1.02-1.27] | 3.89E−05 | 1.16 [1.08-1.24] | 1.18 [1.08-1.29] |
| • |   |   |   | 9q32 | *2.67E−04* | *0.80 [0.71-0.90]* | 6.61E−10 | 0.79 [0.74-0.85] | 0.80 [0.73-0.88] |
|   |   | • |   | 10q21.2 | 1.71E−01 | 1.08 [0.97-1.20] | 3.61E−06 | 1.17 [1.10-1.26] | 1.09 [1.00-1.19] |
| • | • |   |   | 10q24.2 | 9.71E−07 | 1.30 [1.17-1.45] | 1.93E−12 | 1.27 [1.19-1.36] | 1.25 [1.14-1.36] |
| • |   |   |   | 11q13.5 | 4.07E−02 | 1.12 [1.00-1.25] | 1.33E−03 | 1.12 [1.04-1.20] | 1.11 [1.01-1.21] |
| • |   |   |   | 12q12 | 8.32E−01 | 0.97 [0.73-1.28] | 1.35E−03 | 1.30 [1.11-1.53] | 1.05 [0.83-1.31] |
| • |   |   |   | 13q14.11 | 8.40E−01 | 1.01 [0.90-1.14] | 1.27E−03 | 1.13 [1.05-1.22] | 1.03 [0.93-1.14] |
|   |   | • |   | 15q13.1 | 2.39E−01 | 1.08 [0.95-1.23] | 8.89E−01 | 1.01 [0.93-1.09] | 1.04 [0.93-1.15] |
|   | • |   |   | 17q12 | *6.18E−03* | 0.84 [0.75-0.95] | 8.11E−06 | 0.84 [0.78-0.91] | 0.88 [0.79-0.97] |
| • |   |   |   | 17q12 | *6.60E−04* | *1.20 [1.08-1.34]* | 5.01E−05 | 1.15 [1.07-1.23] | 1.19 [1.09-1.30] |

TABLE 14-continued 48 previously identified IBD loci examined by our study, including 8 loci having nominal evidence for association with IBD/CD/UC in previous studies and 2 loci published on a subset of the current cohort (asterisk). Filled circles in the first four columns of the table specify whether the given row represents a (1) known CD locus, (2) putative/nominal CD locus, (3) known UC locus, and/or (4) putative/nominal UC locus, respectively. We replicate 21 of 32 known CD loci, 8 of 15 known UC loci, and overall 26 of 38 known IBD loci. Loci replicating at a Bonferronni-corrected P < .05 are denoted in bold. Our data also implicate several previously described CD loci as having association with UC (bold italics). We also verify 3 nominally associating SNPs from the recent CD meta-analysis (bold italics).

| | | | | | | | | | | |
|---|---|---|---|---|---|---|---|---|---|---|
| • | | • | | 17q21.2 | 1.20E-01 | 0.92 [0.82-1.02] | 1.53E-02 | 0.92 [0.86-0.98] | 0.92 [0.84-1.00] | |
| | | • | | 18p11.21 | 3.12E-01 | 1.08 [0.93-1.24] | 1.69E-03 | 1.15 [1.06-1.26] | 1.08 [0.96-1.22] | |

TABLE 15

8 previously identified IBD loci examined by our study that were either (a) previously nominal signals that are verified by our data or (b) signals previously shown to have an effect on UC (CD) and found by our study to have an effect on CD (UC). Filled circles in the first four columns of the table specify whether the given row represents a (1) known CD locus, (2) putative/nominal CD locus, (3) known UC locus, and/or (4) putative/nominal UC locus, respectively. Overall, we replicate 21 of 32 known CD loci, 8 of 15 known UC loci, and 26 of 38 known IBD loci. Loci replicating at a Bonferronni-corrected P < .05 are denoted in bold, and novel significant effects are denoted in bold italics.

| | | | | | | | | CD All (1689) | | UC All (777) | | IBD All (2413) | |
|---|---|---|---|---|---|---|---|---|---|---|---|---|---|
| (1) | (2) | (3) | (4) | Band | MB | Genes | SNP | P | OR | P | OR | P | OR |
| • | | • | | 1p31.3 | 67.48 | IL23R | rs11465804 | 2.10E-14 | 0.45 [0.36-0.55] | 5.30E-04 | 0.64 [0.49-0.82] | 7.33E-15 | 0.51 [0.43-0.61] |
| | | • | | 1q32.1 | 205.01 | RBBP5, RIPK5 | rs3024505 | 1.01E-04 | 1.22 [1.11-1.36] | 1.12E-03 | 1.26 [1.10-1.45] | 2.57E-06 | 1.24 [1.13-1.35] |
| | • | | | 2p18.1 | 61.34 | AHSA2, CCDC139, PEX13, USP34, PUSA10 | rs13003464 | 2.81E-03 | 1.12 [1.04-1.22] | 1.47E-01 | 1.08 [0.97-1.21] | 1.50E-03 | 1.12 [1.04-1.19] |
| | • | | | 2q12.1 | 102.44 | IL16R1, IL18RAP | rs917997 | 2.23E-06 | 1.23 [1.13-1.34] | 1.56E-01 | 1.09 [0.97-1.23] | 7.09E-06 | 1.19 [1.10-1.29] |
| • | | | | 9q32 | 116.00 | SLC46A2 | rs6476108 | 8.43E-08 | 0.79 [0.73-0.86] | 2.67E-04 | 0.80 [0.71-0.90] | 6.61-e-10 | 0.79 [0.74-0.85] |
| | | • | | 17q12 | 29.61 | CCL11, CCL2, CCL7 | rs991804 | 1.05E-04 | 0.84 [0.77-0.92] | 6.18e-03 | 0.84 [0.75-0.95] | 8.11E-06 | 0.84 [0.78-0.91] |
| | • | | | 17q12 | 35.29 | ORMDL3 | rs2872507 | 2.32E-03 | 1.13 [1.04-1.21] | 6.60E-04 | 1.20 [1.08-1.34] | 5.91E-05 | 1.15 [1.07-1.23] |
| • | | | | 21q22.3 | 44.44 | ICOSLG1 | rs762421 | 1.78E-07 | 1.23 [1.14-1.33] | 7.29E-05 | 1.24 [1.12-1.38] | 1.83E-09 | 1.23 [1.15-1.32] |

Taken together, our results are in keeping with our hypothesis that genome wide analysis of early-onset cases is well suited to detect novel CD loci and the concordance of our results with published CD analyses indicates that there may be many commonalities in the genetic pathogenesis of adult and early onset CD.

Ulcerative Colitis

In the UC analysis, we uncovered three loci with genome-wide significant P-values (P<1.0×10$^{-7}$) and five additional loci attaining suggestive significance (P<1×10$^{-6}$) levels in the discovery cohort (Table 16). We detected association to the previously reported 1 Mb stretch of the MHC region on 6p21 encompassing multiple HLA genes (HLA-DOB, -DQA1, -DQA2, -DRA, -DRB1, -DRB5) as well as to the 10q24 locus containing the NKX2-3 gene. The third signal resides on 21q22 in an LD block containing the genes BWRD1 and PSMG1, which we previously reported in IBD and independently replicated in the publically available CD dataset from WTCCC (11). Here, we observe a robust association with UC alone (rs2836878, P=1.67×10$^{-9}$, OR=0.67 [0.59-0.76]) suggesting that this locus may have a more primary role in the pathogenesis of UC.

TABLE 16

Novel genome wide significant (P < 1 × 10$^{-7}$) and suggestive (P < 1 × 10$^{-6}$) putative UC loci identified in this GWA scan. Criteria for determining bounds of region of association are described in the Methods.

| | | | | UC Discovery (777) | | | |
|---|---|---|---|---|---|---|---|
| Band | Mb | Genes | SNP | P | Aff | Unaff | OR |
| 18q12.2 | 32.22-32.25 | FH0D3, MOCOS | rs7228236 | 9.72E-08 | 0.17 | 0.22 | 0.68 [0.59-0.79] |

TABLE 16-continued

Novel genome wide significant (P < 1 × 10$^{-7}$) and suggestive
(P < 1 × 10$^{-6}$) putative UC loci identified in this GWA scan.
Criteria for determining bounds of region of association are described in the Methods.

| Band | MB | Genes | SNP | P | Aff | Unaff | OR |
|---|---|---|---|---|---|---|---|
| 16q21 | 57.06-57.07 | NDRG4 | rs16960173 | 1.70E-07 | 0.34 | 0.28 | 1.35 [1.20-1.51] |
| 110q25.3 | 115.17-115.26 | HABP2, NRAP | rs12360212 | 2.15E-07 | 0.30 | 0.24 | 1.36 [1.21-1.53] |
| 6p21.33 | 31.43-31.68 | BAT1, LST1, LTA, LTB, NCR3, NFKBIL1, TNF | rs3749946 | 4.56E-07 | 0.14 | 0.09 | 1.50 [1.28-1.75] |
| 2q37.3 | 241.21-241.42 | AQP12A | rs4676410 | 5.60E-07 | 0.24 | .018 | 1.38 [1.22-1.56] |

| | CD meta analysis | | UC Replication (60 trios) | | | | |
|---|---|---|---|---|---|---|---|
| Band | SNP | P | Z | SNP | P | T | U | OR |
| 18q12.2 | Rs7228236 | 3.31E-01 | 0.97 | Rs2000662 | 8.69E-01 | 18 | 19 | 0.95 [0.69-1.86] |
| 16q21 | Rs16960173 | 6.18E-01 | 0.50 | Rs16960170 | 1.00E+00 | 2 | 2 | 1 [0.33-7.1] |
| 10q25.3 | Rs10885450 | 6.27E-01 | -0.49 | Rs12360212 | 1.17E-01 | 21 | 12 | 1.75 [0.74-2.59] |
| 6p21.33 | Rs3749946 | 2.07e-05 | -4.26 | Rs3749946 | 8.66E-01 | 17 | 18 | 0.94 [0.68-1.89] |
| 2q37.3 | Rs4676406 | 1.51E-01 | 1.44 | Rs4676410 | 2.28E-01 | 26 | 18 | 1.44 [0.76-2.14] |

We also sought to follow up on all previously reported adult-onset UC signals (Table 14). Of the 15 previously identified UC loci, 11 showed nominal evidence of replication and 8 were significant to a Bonferroni adjusted P value of 0.05 (adjusting for 15 hypotheses, nominal P<0.0033). These include loci already well established in UC, such as IL23R on 1p31, as well as more recently identified loci like IL10 on 1q32 and CADM2 on 3p12. Examining known CD signals in our UC cohort uncovered three loci that have not been previously associated with UC susceptibility: ICOSLG on 21q22, TNSF15 on 9q32, and ORMDL3 on 17q12 (Table 15).

Inflammatory Bowel Disease

We combined the CD and UC datasets to obtain a composite and more highly powered IBD cohort. Although we did not identify any new loci at the genome-wide significance threshold of P<1.0×10$^{-7}$, we uncovered 3 novel candidate loci at the suggestive P-value threshold of <1×10$^{-6}$. One of these signals corresponds to the 16p11 CD locus already discussed above. The second novel and replicating IBD locus resides on chromosome 22q12. The risk conferring minor allele for rs2412973 (P=9.99×10$^{-7}$; OR=1.18 [1.10-1.26]), replicated in the independent meta-analysis data (P=0.000953, OR=1.17). This SNP resides inside the HORMA domain containing 2 (HORMAD2) gene, an ORF with a Gene Ontology annotation for 'mitosis'; the HORMA domain is a common structural denominator in mitotic checkpoints, chromosome synapsis and DNA repair. Other neighboring genes in the LD block include myotubularin-related protein 3 (MTMR3), which is 50 kb upstream of rs2412973 and encodes a protein phosphatase. Downstream of the LD block is leukemia inhibitory factor (LIF), which resides 100 kb downstream and encodes a cytokine that stimulates differentiation in leukocytes. The third novel and replicating IBD locus at the suggestive significance level resides on 15q22. This locus is highlighted by the SNP rs16950687 (P=6.67×10$^{-7}$, OR=1.20 [1.12-1.29]), which replicates in the meta-analysis data set (P=0.0287, OR=1.10). This SNP lies in an LD block containing the genes SMAD3, a TGFβ activated transcriptional modulator, and IQCH, a protein thought to have a regulatory role in spermatogenesis. We did not observe allele specific changes in HORMAD2 or SMAD3 lymphoblastoid cell line gene expression based on the genotype of these respective SNPs. We also did not observe a difference in expression for these genes between normal and Crohn's disease colonic biopsies (data not shown). The remaining IBD loci did not replicate in the CD meta-analysis cohort. Our most significant IBD signals are summarized in Table 17.

TABLE 17

Novel genome wide significant (P < 1 × 10$^{-7}$) and suggestive (P < 1 × 10$^{-6}$) putative IBD
loci identified in this GWA scan. Loci highlighted in bold italics were independently replicated in a large adult
CD cohort. Z scores in the meta analysis cohort represent directions of effect of the minor allele, with positive
(negative) Z-scores conferring risk (protection). Criteria for determining bounds of region of association are described in the Methods.

| | | | | IBD Discovery (2413) | | | | CD meta analysis | | |
|---|---|---|---|---|---|---|---|---|---|---|
| Band | MB | Genes | SNP | P | Aff | Unaff | OR | SNP | P | Z |
| 8q24.21 | 128.25-128.28 | | rs2456449 | 1.86E-07 | 0.30 | 0.34 | 0.83 [0.77-0.89] | rs2456449 | 2.33E-01 | 1.19 |

TABLE 17-continued

Novel genome wide significant ($P < 1 \times 10^{-7}$) and suggestive ($P < 1 \times 10^{-6}$) putative IBD loci identified in this GWA scan. Loci highlighted in bold italics were independently replicated in a large adult CD cohort. Z scores in the meta analysis cohort represent directions of effect of the minor allele, with positive (negative) Z-scores conferring risk (protection). Criteria for determining bounds of region of association are described in the Methods.

| Band | MB | Genes | SNP | IBD Discovery (2413) | | | | CD meta analysis | | |
|---|---|---|---|---|---|---|---|---|---|---|
| | | | | P | Aff | Unaff | OR | SNP | P | Z |
| 16p11.2 | 28.74-28.81 | IL27 | rs8049439 | 2.37E-07 | 0.41 | 0.37 | 1.20 [1.12-1.28] | rs8049439 | 4.96E-03 | 2.81 |
| 6p21.33 | 31.38-31.67 | BAT1, LST1, LTA, LTB, NCR3, NFKBIL1, TNF | rs2844482 | 5.76E-07 | 0.19 | 0.16 | 1.25 [1.14-1.36] | rs2844482 | 1.02E-01 | 1.63 |
| 15q22.33 | 65.25-65.26 | SMAD3 | rs16950687 | 6.67E-07 | 0.31 | 0.27 | 1.20 [1.12-1.29] | rs16950687 | 2.87E-02 | 2.19 |
| 22q12.2 | 28.75-28.86 | HORMAD2 | rs2412973 | 9.95E-07 | 0.50 | 0.46 | 1.18 [1.10-1.26] | rs2412973 | 9.53E-04 | 3.30 |

Very Early Onset IBD

Given the potential for a genetic enrichment of very early-onset pediatric IBD cases (22), we re-analyzed the data including only cases with age of onset of IBD prior to 8 years of age. This analysis included 466 combined IBD, 266 CD only, and 205 UC only cases. In the UC analysis, we found a cluster of signals encompassing three genes in the toll-like receptor gene family (TLR1, TLR6, and TLR10) (Table 18). This interval contains two independent set of variants: SNPs with risk-conferring minor alleles that associate with OR's 1.49 to 1.59 and SNPs with protective minor alleles that associate with OR's between 0.56 and 0.62. There is one SNP in this region, rs4833103, below the Bonferonni-adjusted threshold for genome-wide significance ($P=1.805\times10^{-8}$, OR=0.56 [0.46-0.69]), with other SNP being supportive. A chart of minor allele frequencies demonstrates the age-dependence of the minor allele frequency of this SNP, which averages 0.35 for patients with onset between ages one and eight, and peaks at to 0.45 for older pediatric UC patients (Table 19). Among SNPs with risk conferring minor alleles, the most significant association was with rs10030125 ($P=2.76\times10^{-6}$, OR=1.589).

However, in order to replicate this result, we employed a small family based cohort of 60 pediatric UC trios with a normal age of onset distribution. We genotyped rs10030125 and an LD surrogate, rs4240248, ($r^2=0.58$) which in the discovery cohort had shown nominal association with a risk conferring effect ($P=1.7\times10^{-4}$, OR=1.45). While genotyping of rs10030125 failed, using the transmission disequilbrium test on this small replication cohort, we found rs4240248 to associate with UC (P=0.008 and OR=2.19) in this independent data set.

Figure 7:
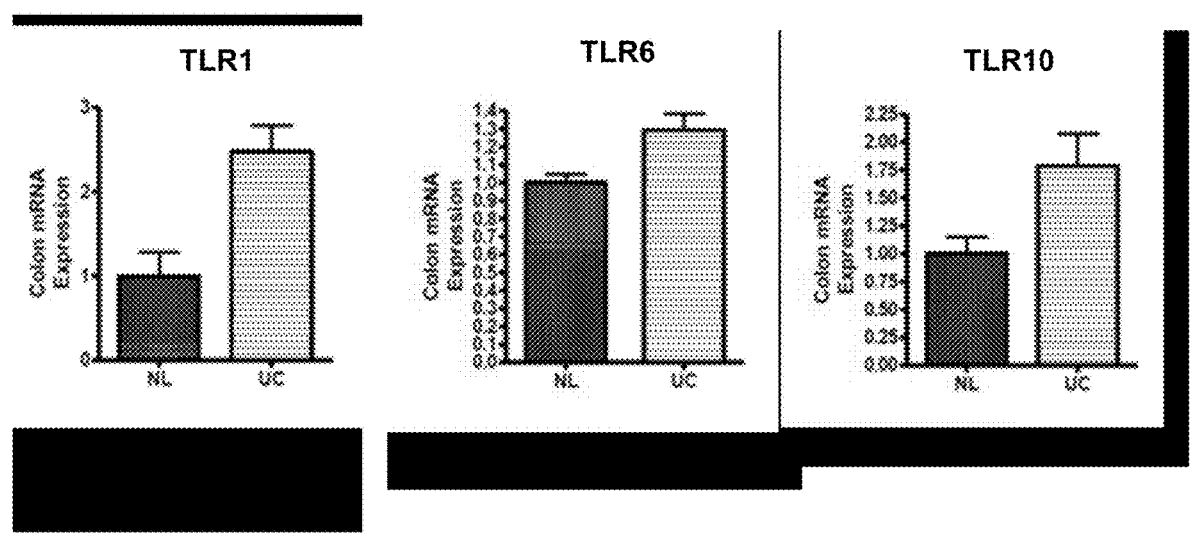
FIG. 7. Colonic expression of TLR genes Expression of the Toll Like Receptor genes, TLR1, TLR6 and TLR10, located in the LD block containing rs4833103, which associates with very early onset (age<=8) UC (P=1.81×10$^{-8}$, OR=0.56 [0.46-0.69]). Students t-test showed statistically significant difference in means for TLR1 (P=0.002), TLR6 (P=0.005) and TLR10 (P=0.02) gene expression between 13 normal (NL) and 10 UC samples.

To further address the potential biological role of the TLR locus in early onset UC, we examined the expression of the genes in this locus, TLR1, TLR6 and TLR10, in the same cell lines as for the IL27 locus as well as in colonic biopsy specimens obtained from normal subjects and patients with UC. Unlike the allele-specific effects observed on IL27 expression, we did not detect allele-specific effects on the TLR gene expression in lymphoblastoid cell lines (data not shown). However, gene expression analysis in colonic biopsies demonstrated that the transcription of TLR1, TLR6, and TLR10 genes is significantly enhanced in UC samples relative to normal (Students t-test P<0.05) (FIG. 7). Taken together, our association findings, when coupled with these expression data, suggest that functional differences in path-

TABLE 18

Early onset UC loci

| REGION | Band | MB | Genes | SNP | Early Onset UC (205 Cases, 6197 Controls) | | | |
|---|---|---|---|---|---|---|---|---|
| | | | | | TopP | Aff | Unaff | OR |
| 1 | 4p14 | 38.26-38.59 | TLR1, TLR6, TLR10 | rs4833103 | 1.81E-08 | 0.35 | 0.49 | 0.56 (0.46-0.68) |
| 2 | 6p21.32 | 32.54-32.94 | Multiple (MHC region) | rs9271568 | 1.12E-07 | 0.18 | 0.31 | 0.51 (0.39-0.65) |
| 3 | 13q22.1 | 73.80-73.82 | | rs10492494 | 2.21E-07 | 0.17 | 0.10 | 1.97 (1.52-2.55) |

TABLE 19 rs4833103 MAF in UC by age

| | 1-2 yo | 3-4 yo | 5-6 yo | 7-8 yo | 9-10 yo | 11-12 yo | 13-14 yo | 16-16 yo | 17-18 yo |
|---|---|---|---|---|---|---|---|---|---|
| rs4833103 MAF | 0.33 | 0.34 | 0.38 | 0.35 | 0.46 | 0.48 | 0.45 | 0.44 | 0.46 |
| n | 18 | 46 | 58 | 92 | 105 | 122 | 140 | 117 | 68 | ways associated with this cluster of Toll-like receptors may contribute to UC pathogenesis, in particular to the very-early onset disease. Extended analysis of very early-onset UC, CD, and IBD cohorts did not yield any further genome-wide significant loci.

Risk Modeling

Figure 8:
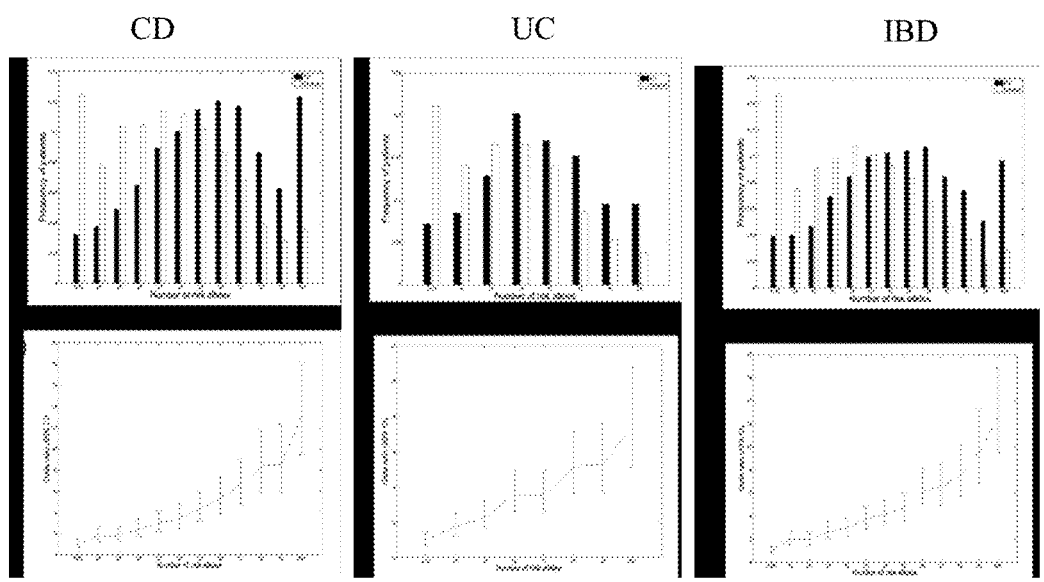
FIG. 8. Cumulative risk modeling of genetic variants associated with IBD. 54 genetic variants (including 6 novel loci discovered in this study) were analyzed in 2134 pediatric IBD cases and 6197 controls to determine their cumulative effects on CD, UC, and IBD risk. Panel's a-c represent distributions of genotypic scores for 30 CD loci, 17 UC loci, and 37 IBD loci, respectively. Panel's d-f represent estimates of cumulative risk as a function of genotypic score for CD, UC, and IBD, respectively.

We evaluated IBD risk in individuals carrying different numbers of risk variants. We conducted separate analyses for CD and UC and for IBD combined. For the CD analysis, we examined risk alleles from 30 replicating loci in our study. Individuals in this cohort carried between 14 and 41 (out of 60 possible) risk alleles, with a case/control frequency distribution as shown in FIG. 8a FIG. 8d demonstrates OR for disease as a function of genotypic score. Analysis of this plot revealed that the OR for CD increases on average by 28% with each increment in the genotypic score above 23. Furthermore, the group of children containing 34 or more risk alleles (comprising the top 3rd percentile of genotypic score) had more than 13 fold increased risk (OR=13.1 [9.4-18.2]) of developing CD. We performed a similar analysis on the UC subcohort, using risk alleles from 17 replicating loci in our study. Individuals in our cohort carried between 7 and 24 (out of 34 possible) risk alleles, with a frequency distribution as shown in FIG. 8b, yielded estimates of cumulative risk as shown in FIG. 8e. In this model, each increment in the genotypic score above 14 increased cumulative UC risk by 36% (on average) to a maximum odds ratio of 7.4 [5.1-10.8]. Finally, we combined CD and UC risk variants to build a IBD cumulative risk model employing 37 total loci and 74 total risk alleles. FIG. 8c shows the frequency distribution of genotypic score among our 2413 IBD patients relative to the cohort of controls. According to this risk model, plotted in FIG. 8f, each additional risk allele increases the odds ratio of IBD by an average of 46%, with the top 3rd percentile of individuals having over 12 fold risk of IBD (OR=12.6 [9.5-16.8]) with respect to the reference group. These results demonstrate that common variants that individually provide relatively small alteration of disease susceptibility can combine to have a dramatic influence on disease risk. This suggests that SNPs discovered in this study and in previous studies have future potential to be incorporated into high-dimensional molecular panels that can be used in clinical diagnosis and management.

Extended CD and UC Analyses

We performed a separate analysis on CD cases excluding patients with the IBD-U diagnosis, yielding 1637 total cases. This analysis uncovered one additional CD signal on 1q22. This signal, highlighted by rs3180018 showed suggestive significance in our discovery cohort (P=6×10$^{-7}$, OR=1.24 [1.14-1.36]). An LD surrogate for rs3180018, rs1052176, nominally replicated in the CD meta analysis (P=0.02, OR=1.11). This SNP lies in the gene SCAMP-3, a carrier protein that participates in post-Golgi recycling pathways.

We also note that a comparable analysis of UC cases excluding patients with the IBD-U diagnosis, yielding 723 total cases, did not reveal any novel associations apart from those listed in the manuscript.

Familial IBD

Given the significant environmental component of IBD, enrichment of the cohort for individuals that have at least one affected first-degree relative has the potential to reveal novel genetic factors mediating IBD susceptibility. Alternatively, IBD cases that cluster in families may represent a specific genetic subtype characterized by a unique set of markers. Of the 2413 cases in our discovery cohort, 289 (14%) have at least one first degree relative (sibling or parent) with IBD. A genome wide analysis on this subset of the cohort revealed only a single locus near genome-wide significance on 16q21 (rs5743289, P=3.31×10$^{-7}$, OR=1.64 [1.35-1.98]), corresponding to the well characterized IBD gene NOD2. The evidence for NOD2, one of the earliest identified IBD susceptibility loci, was initially obtained from the study of families with at least two affected siblings (51). It is noteworthy that our analysis of rs5743289 revealed a weaker association with IBD in the portion of our cohort with sporadic (i.e. non-familial) disease (P=9.06×10$^{-7}$, OR=1.24 [1.14-1.35]). Furthermore, comparison of rs5743289 minor allele frequencies between familial and sporadic IBD cases revealed a significant difference between the two groups (P=0.006), suggesting that NOD2 may be a marker for familial disease.

Colonic IBD Analysis

A separate analysis was performed employing 1178 Colonic IBD cases (including 723 UC, 402 Crohn's, and 53 IBD-U cases) against our control dataset. This analysis revealed several previously identified UC loci at the genome-wide level of significance but did not reveal any novel loci: an 800 KB region of association in the MHC locus on 6p21, 21q22 (near the PSMG1 gene), and the IL23R locus on 1p31. In addition, known IBD loci on 10q24 (NKX2-3) and 5q33 (IL12B) were found at the nominal significance level. We observed several previously uncharacterized loci at the nominal level of significance, including rs12360212 (P=3.7×10$^{-7}$, OR=1.29 [1.17-1.42]) on 18q12 near FHOD and MOCOS, rs7228236 (P=4.5×10$^{-7}$, OR=0.75 [0.67-0.84]) on 10q25 near HABP, NRAP and rs4676410 (P=6.6×10$^{-7}$, OR=1.31 [1.18-1.46]) on 2q37 in the GPR35 gene. These loci were also detected in our UC-only analysis, which contains a subset of these patients. Replication in independent cohorts is difficult due to the uniqueness of this phenotypes in pediatric cases.

Discussion

We have assembled a unique cohort of patients with early-onset IBD from centers in Europe and North America for genome-wide association. In this population, we have identified 5 novel susceptibility loci for pediatric IBD on chromosomes 4p14, 5q15, 6p21, 16p11, and 22q12, and replicated 26 of 38 previously reported IBD loci. For two of these loci, IL27 and the TLR1/TLR6/TLR10 cluster, we provide additional expression data demonstrating significantly altered gene expression that lend further support to the role of these genes in pediatric onset IBD.

The results of our current study add new insight into the pathogenic mechanisms mediating early onset IBD and the interface between early-onset and adult-onset disease. Our findings suggest that molecular events in early-onset disease closely parallel molecular mechanisms in adult IBD. Our discovery of the TLR locus in very-early onset UC suggests that there may also be pathways specific to childhood IBD. Multiple genes involved in innate immunity have already been implicated in IBD, including NOD2, IRGM, and ATG16L1. Loci discovered by our study further crystallize the link between inflammation and the innate/adaptive immune system in the pathogenesis of IBD. Examination of the immune physiology underlying these loci provides intriguing links to genes discovered by previous IBD genome scans and compelling directions for further investigation.

Our discovery of IL27 on 16p11 as a CD susceptibility gene strengthens connections between CD pathogenesis and the dysregulation of the Th-17 cell lineage. Genetic variants within IL-23R, IL-12B, STAT3, and JAK2 loci all affect the same lineage, and have been associated with susceptibility to both CD and UC. TH-17 cells are a recently characterized pro-inflammatory lineage of effector T-cells that are implicated in the pathogenesis of multiple auto-immune/inflammatory diseases, including rheumatoid arthritis, multiple sclerosis, lupus, and asthma (23, 24) The IL27 gene has been the subject of several recent studies examining its role as an in vivo inhibitor of innate and adaptive immunity. Mice deficient in the IL27 receptor have heightened immune responses that are associated with upregulation of multiple T-cell lineages. Furthermore, IL27ra−/− mice demonstrate increased inflammation in response to inoculation with helminthic and intracellular pathogens and are more susceptible to experimental induction of auto-immune colitis, hepatitis, encephalitis, and allergic asthma (25-32). A recent study linked anti-inflammatory effects of IL27 in mice to suppression of the T-helper (TH-17) cell response, mediated through STAT-1 activation and antagonism of IL-6 (26, 33). IL27 mediated immune suppression has also been linked to the modulation of regulatory T-cells. In a recent study, Awasthi et al demonstrated that IL27 mediates differentiation of CD4+ T-cells into Tr1 regulatory T-cells (34). It serves to note that our study is not the first to link IL27 to auto-immune disease susceptibility; variants at this locus have been linked to asthma susceptibility in a recent study performed on a Korean population (35). Our data, demonstrate a profound effect of genotypic variation at the IL27 locus on IL27 gene expression in lymphoblastoid cell lines thereby implicating a role for this gene in CD pathogenesis.

Our study revealed an interval on 5q15 to associate with both early and adult onset CD—the data in our discovery cohort achieving genome-wide significance. Of the two genes in the LD block containing this interval, LRAP presents a more obvious candidate for CD immunopathogenesis: it encodes a leukocyte-derived arginine aminopeptidase that cleaves MHC class I presented antigen peptides and is upregulated by interferon gamma (36, 37).

The IBD susceptibility locus we have identified on 15q22 resides in the LD neighborhood ($r^2 > 0.2$) of SMAD3, another gene providing a link between T-cell dysregulation and CD susceptibility. SMAD3 (along with other SMADs) mediates the signal transduction of TGFβ, a cytokine that pleiotropically affects proliferation, differentiation, and survival in multiple cell types (38). In the intestinal mucosa, TGFβ mediates epithelial wound closure and cellular migration, a pathway that is inhibited in both CD and UC. Smad3 null mice show impaired restitutive epithelial cell migration and slowed mucosal healing in an intestinal ulcer model (39). In the immune system, TGFβ prevents T-cell hyper-reactivity through direct suppression of cytotoxic T-cell and TH1 differentiation and maintenance of regulatory CD4+ T-cells ($T_{reg}$) (38). Of note, TGFβ also has a pro-inflammatory role by stimulating the differentiation of Tx-17 cells. Tx-17 differentiation is impacted not only by IL27 signaling (as discussed above), but is also a downstream target of IL-23R and STAT-3, two CD susceptibility loci that have been replicated by multiple studies (including ours) (2).

We have also discovered a cluster of toll-like receptor (TLR1, TLR6, TLR10) genes whose genetic variation modulates very-early onset UC risk. Ours is the first GWAS to study patients with this rare phenotype. For all three genes in this cluster (TLR1, TLR6, and TLR10), we show significantly increased gene expression in colonic specimens from UC patients indicating that they are active players in the pathogenesis of UC (FIG. 7). TLR's are pattern recognition receptors that recognize antigenic structures broadly-expressed across various species of microorganisms. TLR's are known to synergize with another IBD-susceptibility gene, NOD2, in pathways that trigger and regulate innate immune responses to bacterial pathogens (2, 40). Functionally, TLR1 and TLR6 are known to heterodimerize with another TLR family member, TLR2, to mediate downstream signaling events in innate immunity pathways, while TLR10 is a less well studied "orphan" member of the TLR family. There are numerous existing links suggesting an important role for TLR dysregulation in IBD pathogenesis. Mice deficient in G-protein α inhibitory subunit 2, which mediates intracellular TLR signaling, develop a fatal auto-immune colitis (41). Though TLR1, TLR6 and TLR10 have never been associated with IBD, other toll-like receptors genes (TLR2 and TLR4) have been previously implicated in IBD pathogenesis (42, 43). One study examining the role of TLR gene variation in IBD suggested that variation in TLR1 and TLR6 may modulate the risk of pancolitis and proctitis in UC patients; however, no significant association was detected with UC (44). Variation in the TLR1, TLR6, TLR10 gene cluster have been found by multiple previous studies to modulate prostate-cancer and asthma susceptibility (45-48). UC developing during early childhood differs substantially from adult onset disease, where the colitis is often very limited in extent. The identification of altered TLR gene expression as a risk factor will need to be replicated in additional patients with this phenotypic subtype of IBD.

The additive IBD risk in individuals carrying increasing numbers of variants provides an opportunity to identify high-risk individuals that may be more informative for future studies. The fact that common variants that individually provide relatively small alteration of disease susceptibility can combine to have a dramatic influence on disease risk provides new insight and strategies in pursuing functional studies, molecular diagnostic development and targeted drug design, thereby laying the foundation for the development of personalized treatment algorithms. Thus, the molecular markers discovered in this and previous studies may have future potential to be incorporated into high-dimensional molecular panels that can be used in clinical diagnosis and management.

Though we have identified and replicated a number of novel and previously reported loci in this study, there are likely many more genetic loci to be discovered that modulate both early and adult onset IBD risk. Our genotyping platform captures only a subset of the common Caucasians genetic variation; therefore, it is quite plausible that numerous other common variants may be discovered using a platform with more complete coverage of Caucasian genetic diversity. Application of appropriate genotyping platforms to examine genetic variation in non-Caucasian IBD patients may also reveal novel loci not addressed by this or recent genome-scans. Similarly, replication of early-onset IBD susceptibility loci in non-Caucasian populations is warranted to determine the ethnic heterogeneity of their effect. Loci discovered by our study likely represent surrogates of causal variants. Fine-mapping and resequencing of these regions may reveal haplotypes that confer more profound risk or protection from IBD.

Taken together, our results substantially advance the current understanding of pediatric-onset IBD by highlighting key pathogenetic mechanisms, most notably including Th17 signaling and innate immunity based on the discovery of the IL27 and TLR loci in CD and UC, respectively, quantifying the cumulative IBD risk conferred by multiple risk alleles in pediatric-onset disease, and allowing for the first time a comparison between genetic susceptibility in an exclusively pediatric cohort and the previously described populations with predominantly adult-onset disease.

REFERENCES FOR EXAMPLE III

1. Barrett J C, Hansoul S, Nicolae D L, Cho J H, Duerr R H, Rioux J D, et al. Genome-wide association defines more than 30 distinct susceptibility loci for Crohn's disease. Nat Genet. 2008 Jun. 29; 40(8):955-62.
2. Cho J H. The genetics and immunopathogenesis of inflammatory bowel disease. Nat Rev Immunol. 2008 Jun. 1; 8(6):458-66.
3. Podolsky D K. Inflammatory bowel disease. N Engl J Med. 2002 Aug. 8; 347(6):417-29.
4. Binder V. Genetic epidemiology in inflammatory bowel disease. Digestive diseases (Basel, Switzerland). 1998 Jan. 1; 16(6):351-5.
5. Duerr R H, Taylor K D, Brant S R, Rioux J D, Silverberg M S, Daly M, et al. A genome-wide association study identifies IL23R as an inflammatory bowel disease gene. Science. 2006 Dec. 1; 314(5804):1461-3.
6. Consortium WTCC. Genome-wide association study of 14,000 cases of seven common diseases and 3,000 shared controls. Nature. 2007 Jun. 7; 447(7145):661-78.
7. Fisher S, Tremelling M, Anderson C A, Gwilliam R, Bumpstead S, Prescott N, et al. Genetic determinants of ulcerative colitis include the ECM1 locus and five loci implicated in Crohn's disease. Nat Genet. 2008 Jun. 1; 40(6):710-2.
8. Franke A, Balschun T, Karlsen T H, Hedderich J, May S, Lu T, et al. Replication of signals from recent studies of Crohn's disease identifies previously unknown disease loci for ulcerative colitis. Nat Genet. 2008 Jun. 1; 40(6): 713-5.
9. Vernier-Massouille G, Mamadou B, Julia S, Dominique T, Jean Louis D, Olivier M, et al. Natural History of Pediatric Crohn's Disease: A Population-Based Cohort Study. Gastroenterology. 2008; 135(4):1106-13.
10. Van Limbergen J, Russell R K, Drummond H E, Aldhous M C, Round N K, Nimmo E R, et al. Definition of phenotypic characteristics of childhood-onset inflammatory bowel disease. Gastroenterology. 2008 October; 135 (4):1114-22.
11. Kugathasan S, Baldassano R N, Bradfield J P, Sleiman P M, Imielinski M, Guthery S L, et al. Loci on 20q13 and 21q22 are associated with pediatric-onset inflammatory bowel disease. Nature genetics. 2008 October; 40(10): 1211-5.
12. Kugathasan S, Baldassano R N, Bradfield J P, Sleiman PMA, Imielinski M, Guthery S L, et al. A Genome Wide Association Study Identifies Novel Inflammatory Bowel Disease Susceptibility Loci on 20q13 and 21q22 in Patients with Pediatric Onset IBD. Nat Genet. 2008; 40(10):1211-5.
13. Hakonarson H, Grant S, Bradfield J P, Marchand L, Kim C E, Glessner J T, et al. A genome-wide association study identifies KIAA0350 as a type 1 diabetes gene. Nature. 2007 Aug. 2; 448(7153):591-4.
14. Pritchard J K, Stephens M, Donnelly P. Inference of population structure using multilocus genotype data. Genetics. 2000 Jun. 1; 155(2):945-59.
15. Luca D, Ringquist S, Klei L, Lee A B, Gieger C, Wichmann H E, et al. On the use of general control samples for genome-wide association studies: genetic matching highlights causal variants. Am J Hum Genet. 2008 February; 82(2):453-63.
16. Lyssenko V, Jonsson A, Almgren P, Pulizzi N, Isomaa B, Tuomi T, et al. Clinical risk factors, DNA variants, and the development of type 2 diabetes. N Engl J Med. 2008 Nov. 20; 359(21):2220-32.
17. Purcell S, Neale B, Todd-Brown K, Thomas L, Ferreira M A, Bender D, et al. PLINK: a tool set for whole-genome association and population-based linkage analyses. Am J Hum Genet. 2007 Sep. 1; 81(3):559-75.
18. Stranger B E, Nica A C, Forrest M S, Dimas A, Bird C P, Beazley C, et al. Population genomics of human gene expression. Nat Genet. 2007 October; 39(10):1217-24.
19. Stranger B E, Forrest M S, Dunning M, Ingle C E, Beazley C, Thorne N, et al. Relative impact of nucleotide and copy number variation on gene expression phenotypes. Science. 2007 Feb. 9; 315(5813):848-53.
20. Cauchi S, Meyre D, Durand E, Proenca C, Marre M, Hadjadj S, et al. Post genome-wide association studies of novel genes associated with type 2 diabetes show gene-gene interaction and high predictive value. PLoS ONE. 2008; 3(5):e2031.
21. Meigs J B, Shrader P, Sullivan L M, McAteer J B, Fox C S, Dupuis J, et al. Genotype score in addition to common risk factors for prediction of type 2 diabetes. N Engl J Med. 2008 Nov. 20; 359(21):2208-19.
22. Heyman M B, Kirschner B S, Gold B D, Ferry G, Baldassano R, Cohen S A, et al. Children with early-onset inflammatory bowel disease (IBD): analysis of a pediatric IBD consortium registry. J Pediatr. 2005 January; 146(1):35-40.
23. Steinman L. A brief history of T(H)17, the first major revision in the T(H)1/T(H)2 hypothesis of T cell-mediated tissue damage. Nat Med. 2007 February; 13(2):139-45.
24. Bettelli E, Oukka M, Kuchroo V K. T(H)-17 cells in the circle of immunity and autoimmunity. Nat Immunol. 2007 April; 8(4):345-50.
25. Miyazaki Y, Inoue H, Matsumura M, Matsumoto K, Nakano T, Tsuda M, et al. Exacerbation of experimental allergic asthma by augmented Th2 responses in WSX-1-deficient mice. J Immunol. 2005 Aug. 15; 175(4):2401-7.
26. Batten M, Li J, Yi S, Kljavin N M, Danilenko D M, Lucas S, et al. Interleukin 27 limits autoimmune encephalomyelitis by suppressing the development of interleukin 17-producing T cells. Nat Immunol. 2006 September; 7(9):929-36.
27. Honda K, Nakamura K, Matsui N, Takahashi M, Kitamura Y, Mizutani T, et al. T helper 1-inducing property of IL-27/WSX-1 signaling is required for the induction of experimental colitis. Inflamm Bowel Dis. 2005 December; 11(12):1044-52.
28. Yamanaka A, Hamano S, Miyazaki Y, Ishii K, Takeda A, Mak T W, et al. Hyperproduction of proinflammatory cytokines by WSX-1-deficient NKT cells in concanavalin A-induced hepatitis. J Immunol. 2004 Mar. 15; 172(6): 3590-6.
29. Artis D, Villarino A, Silverman M, He W, Thornton E M, Mu S, et al. The IL-27 receptor (WSX-1) is an inhibitor of innate and adaptive elements of type 2 immunity. J Immunol. 2004 Nov. 1; 173(9):5626-34.
30. Holscher C, Holscher A, Ruckerl D, Yoshimoto T, Yoshida H, Mak T, et al. The IL-27 receptor chain WSX-1 differentially regulates antibacterial immunity and survival during experimental tuberculosis. J Immunol. 2005 Mar. 15; 174(6):3534-44.
31. Pearl J E, Khader S A, Solache A, Gilmartin L, Ghilardi N, deSauvage F, et al. IL-27 signaling compromises control of bacterial growth in mycobacteria-infected mice. J Immunol. 2004 Dec. 15; 173(12):7490-6.
32. Villarino A, Hibbert L, Lieberman L, Wilson E, Mak T, Yoshida H, et al. The IL-27R (WSX-1) is required to suppress T cell hyperactivity during infection. Immunity. 2003 November; 19(5):645-55.

33. Dong C. TH17 cells in development: an updated view of their molecular identity and genetic programming. Nat Rev Immunol. 2008 May; 8(5):337-48.
34. Awasthi A, Carrier Y, Peron J P, Bettelli E, Kamanaka M, Flavell R A, et al. A dominant function for interleukin 27 in generating interleukin 10-producing anti-inflammatory T cells. Nat Immunol. 2007 December; 8(12):1380-9.
35. Chae S C, Li C S, Kim K M, Yang J Y, Zhang Q, Lee Y C, et al. Identification of polymorphisms in human interleukin-27 and their association with asthma in a Korean population. J Hum Genet. 2007; 52(4):355-61.
36. Tanioka T, Hattori A, Masuda S, Nomura Y, Nakayama H, Mizutani S, et al. Human leukocyte-derived arginine aminopeptidase. The third member of the oxytocinase subfamily of aminopeptidases. J Biol Chem. 2003 Aug. 22; 278(34):32275-83.
37. Tanioka T, Hattori A, Mizutani S, Tsujimoto M. Regulation of the human leukocyte-derived arginine aminopeptidase/endoplasmic reticulum-aminopeptidase 2 gene by interferon-gamma. FEBS J. 2005 February; 272(4): 916-28.
38. Rubtsov Y P, Rudensky A Y. TGFbeta signalling in control of T-cell-mediated self-reactivity. Nat Rev Immunol. 2007 June; 7(6):443-53.
39. Owen C R, Yuan L, Basson M D. Smad3 knockout mice exhibit impaired intestinal mucosal healing. Lab Invest. 2008 October; 88(10):1101-9.
40. Trinchieri G, Sher A. Cooperation of Toll-like receptor signals in innate immune defence. Nat Rev Immunol. 2007 March; 7(3):179-90.
41. Rudolph U, Finegold M J, Rich S S, Harriman G R, Srinivasan Y, Brabet P, et al. Ulcerative colitis and adenocarcinoma of the colon in G alpha i2-deficient mice. Nat Genet. 1995 June; 10(2): 143-50.
42. Le Bourhis L, Benko S, Girardin S E. Nod1 and Nod2 in innate immunity and human inflammatory disorders. Biochem Soc Trans. 2007 December; 35(Pt 6):1479-84.
43. De Jager P L, Franchimont D, Waliszewska A, Bitton A, Cohen A, Langelier D, et al. The role of the Toll receptor pathway in susceptibility to inflammatory bowel diseases. Genes Immun. 2007 July; 8(5):387-97.
44. Pierik M, Joossens S, Van Steen K, Van Schuerbeek N, Vlietinck R, Rutgeerts P, et al. Toll-like receptor-1, -2, and -6 polymorphisms influence disease extension in inflammatory bowel diseases. Inflamm Bowel Dis. 2006 January; 12(1):1-8.
45. Lazarus R, Raby B A, Lange C, Silverman E K, Kwiatkowski D J, Vercelli D, et al. TOLL-like receptor 10 genetic variation is associated with asthma in two independent samples. Am J Respir Crit Care Med. 2004 Sep. 15; 170(6):594-600.
46. Tantisira K, Klimecki W T, Lazarus R, Palmer L J, Raby B A, Kwiatkowski D J, et al. Toll-like receptor 6 gene (TLR6): single-nucleotide polymorphism frequencies and preliminary association with the diagnosis of asthma. Genes Immun. 2004 August; 5(5):343-6.
47. Sun J, Wiklund F, Zheng S L, Chang B, Balter K, Li L, et al. Sequence variants in Toll-like receptor gene cluster (TLR6-TLR1-TLR10) and prostate cancer risk. J Natl Cancer Inst. 2005 Apr. 6; 97(7):525-32.
48. Kormann M S, Depner M, Hartl D, Klopp N, Illig T, Adamski J, et al. Toll-like receptor heterodimer variants protect from childhood asthma. J Allergy Clin Immunol. 2008 July; 122(1):86-92, el-8.
49. Barrett J C, Fry B, Maller J, Daly M J. Haploview: analysis and visualization of L D and haplotype maps. Bioinformatics. 2005 Jan. 15; 21(2):263-5.
50. Patterson N, Price A L, Reich D. Population structure and eigenanalysis. PLoS Genet. 2006 December; 2(12): e190.
51. Hugot J P, Laurent-Puig P, Gower-Rousseau C, Olson J M, Lee J C, Beaugerie L, et al. Mapping of a susceptibility locus for Crohn's disease on chromosome 16. Nature. 1996 Feb. 29; 379(6568):821-3.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for treating inflammatory bowel disease (IBD) comprising detecting the presence of at least one IBD-associated single nucleotide polymorphism (SNP) in a target polynucleotide comprising:
   (a) isolating nucleic acids from a biological sample from a subject;
   (b) detecting in the nucleic acids the presence of at least one IBD-associated-SNP selected from a T at rs2315008 in the TNFRSF6B gene, an A at rs4809330 on chromosome 20 in the TNFRSF6B gene, and an A at rs2836878 on chromosome 21; and diagnosing the subject as having IBD or an increased risk of IBD based on the presence of the detected IBD-associated-SNP; and
   (c) administering to the subject a therapeutically effective amount of a therapy useful for treating IBD.

2. The method of claim 1, further comprising, detecting in the sample the presence of an IBD-associated SNP of an A at rs1968752.

3. The method of claim 1, wherein the target nucleic acid is amplified prior to detection.

4. The method of claim 1, wherein the target nucleic acid is DNA.

5. The method of claim 1, wherein nucleic acids comprising said polymorphism are obtained from an isolated cell of a human subject.

6. The method of claim 2, wherein the target nucleic acid is amplified prior to detection.

7. The method of claim 2, wherein detecting the presence of said single nucleotide polymorphism further comprises the step of analyzing a polynucleotide sample to determine the presence of said single nucleotide polymorphism by performing a process selected from the group consisting of detection of specific hybridization, measurement of allele size, restriction fragment length polymorphism analysis, allele-specific hybridization analysis, single base primer extension reaction, and sequencing of an amplified polynucleotide.

8. The method of claim 2, wherein the target nucleic acid is DNA.

9. The method of claim 2, wherein nucleic acids comprising said polymorphism are obtained from an isolated cell of a human subject.

10. The method of claim 1 further comprising, detecting in the sample the presence of at least one IBD-associated SNP selected from a G at rs4625, a T at rs11190140, a T at rs10488959, a C at rs1108458, a G at rs7720838, a T at rs16991082, an A at rs11671391, an A at rs762421, a C at rs17809115, a T at rs2137424, an A at rs2056153, an A at rs2412973, a C at rs3742704, a C at rs1159502, a C at rs11585347, a G at rs17370612, a C at rs511973, a G at rs2548993, a G at rs4811050, a C at rs13219796, a T at rs4529739, an A at rs17170842, a C at rs13232099, a C at rs11585347, an A at rs6722598, an A at rs10759736, an A at rs474816, an A at rs1597317, a T at rs7676830, a G at rs13098182, a C at rs17475446, an A at rs12671457, a T at rs10044354, an A at rs2476601, a T at rs11465804, a T at rs2274910, a G at rs9286879, a G at rs12122721, an A at rs3024505, a G at rs13003464, a C at rs780094, a C at rs6752254, an A at rs2241880, a G at rs7611991, an A at rs3197999, a C at rs4613763, an A at rs7724915, a T at rs2188962, a G at rs7714584, an A at rs10045431, a G at rs2395185, an A at rs660895, a T at rs6908425, an A at rs12529198, an A at rs4959832, an A at rs6938089, a T at rs2301436, a G at rs1456893, a C at rs6478108, a G at rs7130588, a T at rs11174631, a G at rs3764147, a C at rs1667394, a C at rs991804, an A at rs744166, a G at rs1893217, an A at rs7228236, a T at rs16960173, an A at rs3749946, a T at rs2000662, an A at rs2456449, an A at rs4833103, a G at rs9271568, a G at rs1551398, a T at rs2844482, a T at rs2844480, and an A at rs10492494.

11. The method of claim 1 further comprising, detecting in the sample the presence of at least one IBD-associated SNP selected from rs12261843, rs4077515, rs10758669, rs11713694, rs8049439, rs1052176, rs2872507, rs13294, rs917997, rs12360212, rs4676410, rs4676406, and rs16950687, wherein each SNP has an OR value and wherein an OR greater than 1 indicates that the minor allele is the risk allele.

12. The method of claim 1, wherein detecting the presence of said single nucleotide polymorphism further comprises the step of analyzing a polynucleotide sample to determine the presence of said single nucleotide polymorphism by performing a process selected from the group consisting of detection of specific hybridization, measurement of allele size, restriction fragment length polymorphism analysis, allele-specific hybridization analysis, single base primer extension reaction, and sequencing of an amplified polynucleotide.

* * * * *

SEQUENCE LISTING

<160> NUMBER OF SEQ ID NOS: 4

<210> SEQ ID NO 1
<211> LENGTH: 23
<212> TYPE: DNA
<213> ORGANISM: Artificial Sequence
<220> FEATURE:
<223> OTHER INFORMATION: IL27 Primer Sequence Forward

<400> SEQUENCE: 1
tgatgtttcc ctgaccttcc agg            23

<210> SEQ ID NO 2
<211> LENGTH: 22
<212> TYPE: DNA
<213> ORGANISM: Artificial Sequence
<220> FEATURE:
<223> OTHER INFORMATION: IL27 Primer Sequence Reverse

<400> SEQUENCE: 2
acagctgcat cctctccatg tt            22

<210> SEQ ID NO 3

```
<211> LENGTH: 24
<212> TYPE: DNA
<213> ORGANISM: Artificial Sequence
<220> FEATURE:
<223> OTHER INFORMATION: Beta-actin Primer Sequence Forward

<400> SEQUENCE: 3
tcagaaggat tcctatgtgg gcga                                          24

<210> SEQ ID NO 4
<211> LENGTH: 24
<212> TYPE: DNA
<213> ORGANISM: Artificial Sequence
<220> FEATURE:
<223> OTHER INFORMATION: Beta-actin Primer Sequence Reverse

<400> SEQUENCE: 4
cacacgcagc tcattgtaga aggt                                          24
```